(12) United States Patent
Heiter et al.

(10) Patent No.: US 7,081,358 B2
(45) Date of Patent: Jul. 25, 2006

(54) METHOD FOR ENGINEERING STRAND-SPECIFIC, SEQUENCE-SPECIFIC, DNA-NICKING ENZYMES

(75) Inventors: Daniel Heiter, Groveland, MA (US); Keith Lunnen, Essex, MA (US); Geoffrey G. Wilson, Boxford, MA (US)

(73) Assignee: New England Biolabs, Inc., Ipswich, MA (US)

( * ) Notice: Subject to any disclaimer, the term of this patent is extended or adjusted under 35 U.S.C. 154(b) by 143 days.

(21) Appl. No.: 10/223,074

(22) Filed: Aug. 16, 2002

(65) Prior Publication Data

US 2003/0100094 A1 May 29, 2003

Related U.S. Application Data

(60) Provisional application No. 60/314,386, filed on Aug. 23, 2001.

(51) Int. Cl.
C12N 15/55 (2006.01)
C12N 9/22 (2006.01)

(52) U.S. Cl. ............................ 435/199; 435/252.3

(58) Field of Classification Search ................ 435/199, 435/252, 253
See application file for complete search history.

(56) References Cited

U.S. PATENT DOCUMENTS

| 5,246,845 A | 9/1993 | Wilson | 435/112.3 |
|---|---|---|---|
| 5,320,957 A | 6/1994 | Brooks | 435/112.3 |
| 6,395,523 B1 | 5/2002 | Kong | 435/183 |
| 6,867,028 B1 * | 3/2005 | Janulaitis et al. | 436/194 |
| 2003/0148275 A1 * | 8/2003 | Janulaitis et al. | 435/6 |

FOREIGN PATENT DOCUMENTS

WO  WO 99/11821  3/1999

OTHER PUBLICATIONS

Zhu, Z, et al. (2004) J. Mol. Biol. 337, 573-583.*
Samuelson, J.C., et al. (2004) Nucl. Acids Res. 32, 3661-3671.*
U.S. Appl. No. 60/314,386, filed Aug. 2001, Heiter.
Roberts and Macelis, Nucleic Acids Res. 28:306-307 (2000).
Humbelin, et al. J. Mol. Biol. 200:23-29 (1988).
Meisel, et al. Nature 355:467-469 (1992).
Kessler and Holtke, Gene 47:1-153 (1986).
Degtyarev, et al. Nucleic Acids Res. 18:5807-5810 (1990).
Stankevicius, et al. Nucleic Acids Res. 26:1084-1091 (1998).
Degtyarev, et al., Nucleic Acids Res. 28:e56 (2000).
Coligan, et al., Current Protocols in Protein Science, Current Protocols in Protein Analysis (sections 8.3, 10.1 and 11.10) (1997) John Wiley and Sons.
Wilson, Methods in Enzymology 216:259-279 (1992).
Malone, et al., J. Mol. Biol. 253:618-632 (1995).
Howard, et al., Nucleic Acids Res. 14:7939-7951 (1986).
Brooks, et al., Gene 74:13 (1988).
Lunnen, et al., Gene 74:25-32 (1988).
Looney, et al., Gene 80:193-208 (1989).
Sugisaki, et al., J. Bio. Chem. 264:5757-5761 (1989).
Sambrook, A Laboratory Manual, pp. 8.81-8.95 (2001) Cold Spring Harbor Laboratory Press.
Sambrook, A Laboratory Manual, pp. 1.42-1.46 (1989) Cold Spring Harbor Laboratory Press.
Sznyter, et al., Nucleic Acids Res. 15:8249-8266 (1987).
Higgins, et al., Nucleic Acids Res. 29:2492-2501 (2001).
Takami, et al., Nucleic Acids Res. 28:4317-4331 (2000).
Wah, et al., Nature 388:97-100 (1997).
Wah, et al., Proc. Natl. Acad. Sci. USA 95:10564-10569 (1998).
Bitinaite, et al., Proc. Natl. Acad. Sci. USA 95:10570-10575 (1998).
Waugh and Sauer, Proc. Natl. Acad. Sci. USA 90:9596-9600 (1993).
Janulaitis, et al., Nucleic Acids Res. 20:6043-6049 (1992).
Janulaitis, et al., Nucleic Acids Res. 20:6051-6056 (1992).
Kong, et al., J. Biol. Chem. 269:683-690 (1994).
Sears, et al., Nucleic Acids Res. 24:3590-3592 (1996).
Piekarowicz, et al., J. Mol. Biol. 293:1055-1065 (1999).
Kong, et al., J. Mol. Biol., 279:823-832 (1998).
Kong, et al., Nucleic Acids Res. 25:3687-3692 (1997).

* cited by examiner

Primary Examiner—Charles L. Patterson, Jr.
(74) Attorney, Agent, or Firm—Harriet M. Strimpel

(57) ABSTRACT

Methods are provided for converting into a sequence specific strand specific and location specific DNA nicking endonuclease, a restriction endonuclease that recognizes an asymmetric DNA sequence, the endonuclease having two catalytic sites and one or more single sequence specific DNA-binding domains. In one embodiment the method requires inactivating one of the catalytic sites of the restriction endonuclease. In another embodiment, the restriction endonuclease is a dimer having a first and second subunit each comprising a sequence specific DNA binding domain, a catalytic site and a dimerization domain. The nicking endonuclease is formed from combining one subunit having an inactivated catalytic site and a second subunit having an inactivated DNA binding domain. The nicking endonuclease may be converted into a restriction endonuclease by the addition of manganese cations in the digestion buffer.

18 Claims, 20 Drawing Sheets

FIGURE 2

M1-BbvCI 423 aa (nt 97-1368) MW: 48.7 Kda
(SEQ ID NO:2)

```
  1 MESETRQNIQ KQLTAIDLFA GAGGFSLGFS MAGFRVTHAI EVDKWAAETF
 51 EVNFPRTKVV TRDIQISDE EIKDIIDERP LVVIGGPPCQ GFSHSNVNNK
101 DPKDPRNSLF QEYMRFVAQL RPKVCMIENV KGLLITKTAK GELVIDIILR
151 EFESLGYNAD FRVLNAANFG VPQFRERLII AAVCKSEANN FFWPEPTHEL
201 GNSNITSLFE ELMPTQPPLT LWEAIGDIQQ ITHESYTGKE GYECSPLNEF
251 QSIMRRNAPE FLLNHEPMKH TKRVVERYAT IGFGSEGDV SEKHLPRKRS
301 ESSTISKAYD QNGRRQRPDR PCSTIVASSH SNFTIHPFLHR NFTVRELARI
351 QSFDDYEFR GKRAVLSKKL SIRKGLLDEI YLDQRMQVGN AVPPLFAKAL
401 AESVRSTLSL TNSRGGKNEI CST*
```

M2-BbvCI 396 aa (nt 1349-2539) MW: 44.1 Kda
(SEQ ID NO:3)

```
  1 MKFVALDIFA GCGGFSSGLI QAGHEVTSAL EIDSWAAETY QFNHRNVNLL
 51 TEDITKVDST YFKVNFKDRV NLVVGGPPCQ GFSVSGPRQY GVYKKENALV
101 AEYIRVIKAV EPEYFILENV RGFTTATIEG RIKALNFLLA ELREIGYHVY
151 HDVLQAADYG VPQLRSGRLFV VGSRHPIANP FPNKTHSLNG TQHLRPYLSI
201 MEAIGDLPII NACEGTDNLV QYSLEPQNDF QQAMRNGSLG VYNHEAMKHS
251 ARIVERFATI QPGGSGVKLG TVKGKDAPET VYKSNNQRLI SDQPALCITA
301 NWQSSYIHPL LNRNLTVREA ARIQTFPDSY VFKGKRAVPS ASLLRKLGRD
351 DENFLSQCHQ VGNAVPPLLA KQIFERLSVA VEGVDEESSE QLQLWG*
```

R1-BbvCI 275 aa (nt 2542-3369) MW: 31.4 Kda
(SEQ ID NO:4)

```
  1 MINEDFFIYE QLSHKKNLEQ KGKNAFDEET EELVRQAKSG YHAFIEGINY
 51 DEVTRKLDLNS SVAALEDYIS IAKEIEKKHK MFNWRSDYAG SIIPEFLYRI
101 VHVATVKAGL KPIFSTRNTI IEISGAAHRE GLQIRRKNED FALGFHEVDV
151 KIASSSHRVI SLAVACEVKT NIDKNKLNGL DFSAERMKRT YPGSAYPLIT
201 ETLDFSPDEN HSSGLIDEIY VLRKQVRTKN RVQKAPLCPS VFAELLEDIL
251 EISYRASNVK GHVYDRLEGG KLIRV*
```

R2-BbvCI 285 aa (nt 3369-4219) MW: 32.6 Kda
(SEQ ID NO:5)

```
  1 MFNQFNPLVY THGGKLERKS KKDKTASKVF EEFGVMRAYN CWKEASLCIQ
 51 QRDKDSVLKI VAALNTYKDA VEPIFDSRLN SAQEVLQPSI LEEFFEYLFS
101 RIDSTVGVNI PIRHPAKGYL SLSFNPHNIE TLIQSPEYTV RAKDHDFIIG
151 GSAKLTIQGH GGEGETNIV VPAVAIECKR YLERNMLDEC AGTAERLKFA
201 TPYCLYFVVA EYLKLDDGAP ELTEIDEIYI LRHQRNSERN KPGFKPNPID
251 GELIWDLYQE VMNHLGKIWW DENSALQRGK VFNRP*
```

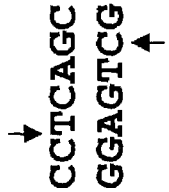

CCTCAGC
GGAGTCG

- Two m5C-methylases (one for modifying each strand)
- Two endonuclease subunits (one for cleaving each strand)

- Bacillus lentus
- Typical type II system: one M gene and one R gene

FIGURE 4

M-BlpI 391 aa (nt 179-1354) 44.3 Kda
(SEQ ID NO:7)
  1 MKVLDLFAGA GGFSLGFEMA DYEVIGGVEI DKWAGETLAH NHPGIILINK
 51 NITNVTNEEL LEKFKDNFPD VIIGGPPCQG FSISNRKAGD PKDPRNSLFK
101 EFIRIASVFK PQYLVMENVP NLLKAKTENK ELVIDIIRKE MENLGYNVYV
151 DVLSATDFGV PQIRKRLFVI GSKTKLDKPF PSPTHYVLGE NDSLFNEKLE
201 ITPTLWDAIS DLPTIEAREG AEEMEYTMEP QTDYQRYLRE GSAKVYNHKA
251 MNHTKRMVER FASMTFGNSI SDVPEHLRPY KRNQVGVISD KLYDQNNRRM
301 FPDRPCHTIA ASFYANFVHP FLNRNFTARE GARIQSFPDS YVFKGKPTVV
351 SKKLLASEGR TDESYLCQYN QIGNAVPPML AKAIADNLKK N*

R-BlpI 289 aa (nt 1373-2242) MW: 33.6 Kda
(SEQ ID NO:8)
  1 MFVHGDNLTQ KENHRTKYTD GLSKQYLTEI REKYNEWKKA NEELIGPFAE
 51 ATPEDEAIVK KRVELLNDYK DFVDQQHYAE KFDSRSNLHS SILEEFVYYL
101 FKDIAKSFND EAIVGKSHAF KDLFINPSSY KDMVTQPNVK VEIKDHDFII
151 GVGIEAKMIV KGSTEIENHT LEVAAVAIEC KTYLDKTMLE GSSVAAEQLK
201 SRNPNAKYIV VSEWLKLSEQ VNLQKYKVDQ IYVLRKQKNT DREFRYADTY
251 VKNAIHEDVV LHLFHTIRLH LTTEWDGSIS HGIDRGYLL*

GCTNAGC ↓
CGANTCG ↑

• One m5C-methylase
• One endonuclease subunit

- Bacillus subtilis 36
- Typical type II system: one M gene and one R gene
- Flanked by 194-bp direct repeats

FIGURE 6

CCTNAGG
GGANTCC

- One m4C-methylase
- One endonuclease subunit

M-Bsu36I 417 aa (nt 2102-3355) 48.2 KDa
(SEQ ID NO:10)
1 MKELFIMKYT PQKIFKTIDD FPYDRTSVSQ SELDLDIKER KSLFPWRGQF
51 SPCLIELFLD RYSKPDDVIF DPFAGSGTTL FESARKNIKC YGAEINPSAI
101 TMSKTVEFIN MSTEDREKLC NAAIIILKKY IRESNYDLFN MDLYEEKSAP
151 FEIAFKKMLN ESPNSQVINI LTNALIRFKS YRGKKALEDY YKALHEHIKI
201 IKNLPYSENI CEVFHTDARS IPLANDSVDL IITSPPYINV FNYHQNNREA
251 MEFVGWNVLE VAKSEMGSNR KHRQNRFLTV IQYSMDILEA LIEMRRLLTP
301 SGRVIVVGR ESKIRGVPLK NGRLVAALAY GGAGFKIENM QERKFTNKFG
351 ELIYEDITHL TPSNTSVLDE SYAKNMANEL LKEALIMEKD ENIRIEILNA
401 INKSDSVKKS PIFEMDF*

R-Bsu36I 310 aa (nt 1373-2242) MW: 35.9 Kda
(SEQ ID NO:11)
1 MTTYIYPTPH KDKLVALLLN DKLPVEDKPR VEEAIVYTN WIKNLNIITS
51 AGLPPQQTLN KMIELLNEYK FYTDINIVFD SPRDFLYRQK GQLKIDNTII
101 EEFLPRLAHP SVIPEIIDMD VTVGFKKCFS SVYFESSLDA PAIGGGLRVR
151 SKDQDFAISK KLFLKASHTQ DYKESLETET FLSYVSAECK TNLDKTMFQE
201 GCATAHDTKV AVPGSKYFLL CEWIDMTPLS TAPTDIDEIL LLRKAKRLNS
251 NIRKKFSSYS GRQEKRDYFI NYLKSHPFRV EVFERFIEHI RKLIQNEVPV
301 EHNVMELGYF *

FIGURE 7

```
R1-BbvCI    mgvvMINEDFFIYEQL.SHKKN.LEQKGKNAFDEETEELVRQAKSGYHAFIE.GINYDEVTKLD...LNSSVAALEDYTSIAKEIEKKHKMFN......WRSDYA
R-bsu36I    MTTYIYPTPHKDKLVALLINDKLPVEDKPRVEEAIVVYTNMIKNLNIITSAGLPPQQTLNKMIELLNEXKFYIDLNLVFDSPRDFLYRQKGQLKID
R-BlpI      MFVHGDNLTQKENHRTKYTDGLSKQYLTEIREKYNEWKKANEELIGPFAEATPEDEAIVKKRVELLNDYKDFVDQQH.YAEKFD......SRSNLH
R2-BbvCI    mFNQFNPLVYTHGGKLERKSK.KDKTASKVFEEF..GVMRAYNCWKEASLCI......QQRDKDSVLKLVAALNTYKDAVEPIF.DSRLNS......AQEVLQ
DdeI        MKAATDQELRKLIVLYNNVMEVMEHDAAKSMRDDNRAYGGFVRAAKGKIQELITERLVRTVWDV R1-BbvCI    GSIIPEFLYRIVHVATVKAGLKP........IFSTRNTIIE.  ISGAAHREG.LQIRRKNEDFALG......FHEVDVKIASESHRVISLAVACEVKTNIDKNKLNGLDF
R-bsu36I    NTIIEEFLPRLAH..PSVIPRIIDMDVTVGPKKCPSSVYFE.SSLDAPAIGGGLRVRSKDQDFAISKKLFLHASHTQDYKESLETETFLSYVSAECKTNIDKTMFQEGQA
R-BlpI      SSILEEFVYYLFKDIAK....SFNDEAIVGKSHAFKDLFINPSSYKDMVTQPNVKVEIKDHDFIIGVGIEAAKMIVGSTEIENHT.LEVAAVALECKTYIDKTMLEGSSV
R2-BbvCI    PSILEEFFEYLFSRIDSIVGVNIP...IRIIPAKGYLSLSFNPHNIETLIQSPEYTVRAKDHDFIIGGSSAKLTI..QGHGGEGETTNIVPAVALECKRYIERMLDECAG
R-DdeI      EMGENPERLSINSKKIKIPILRSYVDSINDENLKKYISSNILKYSYGLSVDKHVFIDN                           KFVLGIECKAVTENAMLKRILV R1-BbvCI    SAERMKRTYPGSAYFLITETLDFSPD.ENHSSGLIDETYLRKQVRTKNRVQKA.PLCP..SVFAELLEDILE.ISYRASNVKGHVYD...RLEGGKLIRV
R-bsu36I    TAHDTKVAVPGSKYFLLCEWLDMTPLSTAP..TDIDEILLLRKAKRLNSNIRKKFSSYSGRQEKRDYFINYLKSHPFRVEVFERFIEHIRKLIQNEVPVEHNVMELGYF
R-BlpI      AAEQLKSRNPNAKYIVVSEWLKLS.EQVNLQKYKVDQIVLRKQKNTDREFRYA.DTYVKNAIHEDVVLHFHTIRLHLTTEWD..GSISHGIDRGYLL
R2-BbvCI    TAERLKRATPYCLYFVVAEYLKL..DDGAPELTEIDEIYILRHQRNSER...NK.PGFKPNPIDGELIWDLYQEVMNHLGKIW...WDPNSALQRGKVFNRP
R-DdeI      DFYLLKTKFPKLNCFLFQLESQLGGDYSECNKFPIGSYPTRTIMSYFKNVDLNIVTLLEGERKVDRPINKPQFFKPLKVEHLEVAIGYLQESLSEI
```

- Sequential, complementary, nicking results in BbvCI-specific, double-strand, cleavage

Figure 15

| Representative enzyme | Recognition sequence & hydrolysis positions | Isoschizomers |
|---|---|---|
| AciI | C^C G C<br>G G C^G | None known |
| BbvCI | C C^T C A G C<br>G G A G T^C G | AbeI |
| Bpu10I | C C^T N A G C<br>G G A N T^C G | BpuDI |
| BsrBI | G A G^C G G<br>C T C^G C C | AccBSI, BstD102I, Bst31NI, MbiI, |
| BssSI | C^T C G T G<br>G A G C A^C | BsiI, Bst2BI |
| BtrI | C A C^G T C<br>G T G^C A G | None known |
| GdiII | C^G G C C R<br>G C C G G^Y | None known |

| BsmI | G A A T G C N^<br>C T T A C^G N | Asp26HI, Asp27HI, Asp35HI, Asp36HI, Asp40HI, Asp50HI, BsaMI, BscCI, Mva1269I, PctI |
|---|---|---|
| BsrI | A C T G G N^<br>T G A C^C N | BscHI, Bse1I, BseNI, BsoHI, BsrSI, Bst11I, Tsp1I, |
| SimI | G G^G T C N<br>C C C A G^N | None known |

| BsrDI | G C A A T G N N^<br>C G T T A C^N N | Bse3DI, BseMI |
|---|---|---|
| BstF5I | G G A T G N N^<br>C C T A C^N N | BseGI, BstF5I |
| BtsI | G C A G T G N N^<br>C G T C A C^N N | None known |

| BstNBI | G A G T C NNNN^<br>C T C A G NNNN | Bst9I, BstSEI |
|---|---|---|
| BbvI | G C A G C NNNNNNNN^NNN<br>C G T C G NNNNNNNNNNNN^ | AlwXI, BchI, BsaUI, BseKI, BseXI, Bsp423I, BsrVI, Bst12I, Bst71I, LfeI, Lsp1109I |

Figure 16

| Enzyme prep | Subunit composition | Enzyme yield | Specific activity (u/mg) | Specific activity (u/nmole) |
|---|---|---|---|---|
| R.BbvCI wt | $R_1^+:R_2^+$ | 40 ml @ $5 \times 10^6$ u/ml | $1 \times 10^5$ | $6 \times 10^3$ |
| N.BbvCI 1-37 | $R_1E167G:R_2^+$ | 18 ml @ $3 \times 10^5$ u/ml | $1 \times 10^4$ | $6 \times 10^2$ |
| N.BbvCI 2-12 | $R_1^+:R_2E177G$ | 38 ml @ $1.5 \times 10^6$ u/ml | $5 \times 10^4$ | $3 \times 10^3$ |

Figure 17-1

| Isolate | Nucleotide sequence (R₁ subunit) | Amino acid sequence | | Crude Enzyme activity | | |
|---|---|---|---|---|---|---|
| | | R₁ subunit | R₂ subunit | Cut | Nick | Dead |
| WT | TGT GAAGTTAAA ACA (SEQ ID NO:13) | EVK | ECK | √ | | |
| 1-4 | TGT gagatcacg ACA (SEQ ID NO:14) | EIT | + | | √ | |
| 1-5 | TGT gagttgaag ACA (SEQ ID NO:15) | ELK | + | √ | | |
| 1-14 | TGT gagggcaag ACA (SEQ ID NO:16) | EGK | + | | | √ |
| 1-19 | TGT gtggacaag ACA (SEQ ID NO:17) | VDK | + | | | √ |
| 1-27 | TGT ggggtccag ACA (SEQ ID NO:18) | GVQ | + | | √ | |
| 1-29 | TGT gacgtcaag ACA (SEQ ID NO:19) | DVK | + | Mn | √ | |
| 1-32 | TGT taggtcaag ACA (SEQ ID NO:20) | *VK | + | | | √ |
| 1-34 | TGT ggcgtgcag ACA (SEQ ID NO:21) | GVQ | + | | √ | |
| 1-35 | TGT gaggtggag ACA (SEQ ID NO:22) | EVE | + | | √ | |
| 1-36 | TGT tacgtcaac ACA (SEQ ID NO:23) | YVN | + | | | √ |
| 1-37 | TGT ggggtgaag ACA (SEQ ID NO:24) | GVK | + | Mn | √ | |
| 1-39 | TGT gggatgaac ACA (SEQ ID NO:25) | GMN | + | | √ | |
| 1-40 | TGT gacgtcgag ACA (SEQ ID NO:26) | DVE | + | | √ | |
| 1-42 | TGT gtggagaag ACA (SEQ ID NO:27) | VEK | + | | | √ |
| 1-45 | TGT gacttcatg ACA (SEQ ID NO:28) | DFM | + | | (√) | |
| 1-48 | TGT gagctcaac ACA (SEQ ID NO:29) | ELN | + | | (√) | |

FIGURE 17-2

| Isolate | Nucleotide sequence (R₁ subunit) | Amino acid sequence | | Crude Enzyme activity | | |
|---|---|---|---|---|---|---|
| | | R₁ subunit | R₂ subunit | Cut | Nick | Dead |
| 1-52 | TGT gaggtcagg ACA (SEQ ID NO:30) | EVR | + | | (√) | |
| 1-53 | TGT gacgtctac ACA (SEQ ID NO:31) | DVY | + | | (√) | |
| 1-58 | TGT gacgtcgac ACA (SEQ ID NO:32) | DVD | + | | | √ |
| 1-59 | TGT gagatcagg ACA (SEQ ID NO:33) | EIR | + | | (√) | |
| 1-79 | TGT gtgggctag ACA (SEQ ID NO:34) | VG* | + | | | √ |
| 1-80 | TGT ggcacggac ACA (SEQ ID NO:35) | GTD | + | | | √ |

Figure 18-1

| Isolate | Nucleotide sequence (R₂ subunit) | Amino acid sequence | | Crude Enzyme activity | | |
|---|---|---|---|---|---|---|
| | | R₁ subunit | R₂ subunit | Cut | Nick | Dead |
| wt | ATT GAATGCAAG CGG (SEQ ID NO:36) | EVK | ECK | √ | | |
| 2-2 | ATT gagggccag CGG (SEQ ID NO:37) | + | EGQ | | √ | |
| 2-5 | ATT ttgtggaag CGG (SEQ ID NO:38) | + | LWK | | | √ |
| 2-7, 29 | ATT gagtggaag CGG (SEQ ID NO:39) | + | EWK | | | √ |
| 2-10 | ATT ggctgcaag CGG (SEQ ID NO:40) | + | GCK | | √ | |
| 2-12, 51 | ATT gggtgcaag CGG (SEQ ID NO:41) | + | GCK | | √ | |
| 2-15 | ATT gagaggcag CGG (SEQ ID NO:42) | + | ERQ | | | √ |
| 2-16 | ATT gagtgcatg CGG (SEQ ID NO:43) | + | ECM | | √ | |
| 2-18 | ATT gggtgcgag CGG (SEQ ID NO:44) | + | GCE | | | √ |
| 2-21 | ATT cagtacaag CGG (SEQ ID NO:45) | + | QYK | | √ | |
| 2-24 | ATT gggtggaag CGG (SEQ ID NO:46) | + | GWK | | | √ |
| 2-25 | ATT gagtgggag CGG (SEQ ID NO:47) | + | EWE | | | √ |
| 2-27 | ATT gacgacaag CGG (SEQ ID NO:48) | + | DDK | | | √ |
| 2-31 | ATT gagttcaac CGG (SEQ ID NO:49) | + | EFN | | √ | |
| 2-34 | ATT gactgcgag CGG (SEQ ID NO:50) | + | DCE | | | √ |
| 2-35 | ATT gcctggaag CGG (SEQ ID NO:51) | + | AWK | | | √ |
| 2-36 | ATT ccgtgcaac CGG (SEQ ID NO:52) | + | PCN | | | √ |
| 2-37 | ATT aagtgcagc CGG (SEQ ID NO:53) | + | KCS | | √ | |
| 2-39 | ATT gagaccaag CGG (SEQ ID NO:54) | + | ETK | √ | | |

Figure 18-2

| Isolate | Nucleotide sequence (R₂ subunit) | Amino acid sequence | | Crude Enzyme activity | | |
|---|---|---|---|---|---|---|
| | | R₁ subunit | R₂ subunit | Cut | Nick | Dead |
| 2-40 | ATT gagagggag CGG (SEQ ID NO:55) | + | ERE | | | √ |
| 2-45 | ATT gtctgcaag CGG (SEQ ID NO:56) | + | VCK | | √ | |
| 2-47 | ATT gagtacagg CGG (SEQ ID NO:57) | + | EYR | | | √ |
| 2-48 | ATT gactacgag CGG (SEQ ID NO:58) | + | DYE | | | √ |
| 2-49 | ATT gacggctgg CGG (SEQ ID NO:59) | + | DGW | | (√) | |
| 2-52 | ATT ttgtgcaag CGG (SEQ ID NO:60) | + | LCK | | (√) | |
| 2-54 | ATT tagtgcaag CGG (SEQ ID NO:61) | + | *CK | | | √ |
| 2-56 | ATT gactgcaag CGG (SEQ ID NO:62) | + | DCK | Mn | √ | |
| 2-59 | ATT gagagcaag CGG (SEQ ID NO:63) | + | ESK | √ | | |

METHOD FOR ENGINEERING STRAND-SPECIFIC, SEQUENCE-SPECIFIC, DNA-NICKING ENZYMES

RELATED APPLICATIONS

This is a Non-Provisional Application of Provisional Application Ser. No. 60/314,386 filed on Aug. 23, 2001 herein incorporated by reference.

BACKGROUND OF THE INVENTION

Enzymes are fundamental components of all living cells. Encoded by genes, and comprising proteins for the most part, enzymes orchestrate the multitude of chemical processes upon which life depends. Simple living organisms, such as bacteria, synthesize around 1000 enzymes, the minimum repertoire for independent existence, while complex organisms such as ourselves synthesize far more, perhaps as many as 30,000. Enzymes are profoundly powerful; the biochemical nuances of a single enzyme among thousands can spell the difference between health or disease; survival or death.

There is considerable interest in enzymes, both as objects for study, and as molecular tools for experimentation and analysis in the laboratory. Chief among the latter are restriction endonucleases, enzymes synthesized by bacteria and archae that catalyze the cleavage of double-stranded DNA molecules. Over two hundred and fifty distinct restriction endonucleases have been discovered, each differing in the specifics of the sites within DNA at which they induce cleavage (Roberts and Macelis, *Nucleic Acids Res.* 28:306–307 (2000)). Two hundred of these are manufactured commercially, and many have become tools of the trade for molecular biologists in scientific and medical institutions around the world.

Restriction endonucleases bind to duplex DNA at particular sequences of nucleotides termed 'recognition sequences'. Once bound, they hydrolyze the two sugar-phosphate strands that make up the paired, helical backbones of the DNA molecule. Following hydrolysis, the endonucleases generally detach from the DNA, and the two fragments of the severed DNA molecule are released. As a rule, the two strand-hydrolysis reactions proceed in parallel in a double reaction that requires the presence of two catalytic sites within each enzyme, one for hydrolyzing each strand. In most cases, these two catalytic sites are identical because, in their catalytically active forms at the moment of DNA cleavage, most restriction endonucleases are homodimeric; that is to say, they are composed of two identical protein subunits, or assemblages of subunits, bound to each other in symmetrical, if fleeting, opposition. Each subunit or assemblage possesses a single catalytic site, and so the active homodimer possesses two.

For certain laboratory applications it would be useful if variant restriction endonucleases were available that hydrolyzed only one strand of duplex DNA rather than hydrolyzing both strands. Because such enzymes—'DNA-nicking' endonucleases as opposed to 'DNA-cleaving' endonucleases—are uncommon in nature, we have developed a method for producing them in the laboratory. This method, and the nicking endonucleases we have made, or anticipate making, by application of the method form the basis for this patent application. The method relies on identifying a restriction endonuclease that possesses two different catalytic sites for strand hydrolysis, rather than two identical sites, and then inactivating one site or the other by mutation to form an altered enzyme in which only one of the two sites retains catalytic ability. Provided the inactivating mutation (s) do not interfere with the functioning of the other catalytic site, or with the ability of the protein to fold properly and bind to its recognition sequence in DNA, the mutated enzyme should hydrolyze only one strand of DNA. Nicking enzymes created in this way will be sequence-specific, in that nicking will occur only at the recognition sequence. They will be strand-specific, in that which of the two DNA strands becomes nicked will depend upon which of the two catalytic sites in the enzyme retains function. And they will be position-specific in that the position of the nick with respect to the recognition sequence, determined by the geometry of the enzyme, will be predictable and constant.

SUMMARY OF THE INVENTION

A method is provided whereby certain restriction endonucleases that hydrolyze both strands of duplex DNA ('cleave') can be converted into enzymes that hydrolyze only one strand of duplex DNA ('nick'), instead. The method involves identifying a restriction endonuclease that possesses two different catalytic sites for strand-hydrolysis, and then discretely inactivating one site or the other by mutation to create a variant enzyme that possesses only one catalytic site. Nicking enzymes created in this way hydrolyze only one strand of DNA, and they do so in a sequence-specific, strand-specific, and location-specific manner. The nicks introduced into DNA by the actions of these enzymes can serve as initiation points for further enzymatic reactions including strand-specific DNA amplification, degradation, mutagenesis, polymerization, and recombination. The restriction endonucleases to which this method is applicable are primarily those that recognize continuous asymmetric nucleotide sequences, and cleave within or close to one side of these sequences; enzymes, that is to say, belonging to the Type IIs, IIt, and IIf classes. (New England Biolabs nomenclature, 2000) We applied the method to R.BbvCI, a Type IIt restriction endonuclease that cleaves DNA within the asymmetric seven-base pair recognition sequence 5'-CCTCAGC-3'. The method generated a novel pair of complimentary nicking enzymes, $N_t$.BbvCI, that nicked DNA two bases inside the 'top' strand of the sequence, thus: 5'-CC^TCAGC-3'; and $N_b$.BbvCI, that nicked DNA two bases inside the 'bottom' strand, thus: 5'-GC^TGAGG-3' (see Example 1).

The method described here is applicable to the Type IIs endonucleases including R.BbvI and N.BstNBI, and provides a means to generate additional novel endonucleases that nick either DNA strand several bases downstream of the sequences 5'-GCAGC-3' and 5'-GAGTC-3', respectively (Example 2). A variation of the method is applicable to other Type II endonucleases such as R.FokI (Type IIs), and to certain Type IIf endonuclease-methyltransferases, such as Eco57I, that do not normally use two different catalytic sites to accomplish DNA cleavage, but might be made to do so by genetic manipulation (Example 3).

BRIEF DESCRIPTION OF THE DRAWINGS

FIG. 2. Amino acid sequences of the BbvCI methyltransferases, and endonuclease subunits (SEQ ID NO:2, SEQ ID NO:3, SEQ ID NO:4 and SEQ ID NO:5).

FIG. 4. Amino acid sequence of the BlpI methyltransferase and endonuclease (SEQ ID NO:7 and SEQ ID NO:8).

FIG. 6. Amino acid sequence of the BSu36I methyltransferase and endonuclease (SEQ ID NO:10 and SEQ ID NO:11).

FIG. 7. Amino acid sequence alignment between the BlpI (SEQ ID NO:8), Bsu36I (SEQ ID NO:11), and DdeI (SEQ ID NO:12) restriction endonucleases and the two endonuclease subunits of BbvCI (SEQ ID NO:4 and SEQ ID NO:5). DdeI differs so radically from the other four proteins beyond the catalytic site regions (boxes) that alignment has only been attempted with DdeI in these regions. Within regions of marked similarity, identical amino acids are indicated by vertical lines and similar amino acids by colons. Entirely conserved residues likely to be involved in catalysis are shown in bold.

FIG. 15. Restriction endonucleases likely to possess two different catalytic sites for DNA strand-hydrolysis. These enzymes, and others like them, are candidates for conversion to DNA-nicking enzymes by the present invention. These enzymes recognize continuous asymmetric DNA sequences and catalyze strand-hydrolysis within those sequences or just outside. Many of the enzymes come from bacteria of the genus *Bacillus*, suggesting that this genus could be a productive source of further enzymes of this category.

FIG. 16. Endonuclease yields and activities from 100 gm wet pastes of cells expressing wild type BbvCI, and the nicking derivatives 1-37 and 2-12. 1 unit of R.BbvCI activity is defined here as the least amount of enzyme that completely converts 1 microgram of supercoiled pUB DNA (2 recognition sites) into two fragments in 1 h at 37° C. in 50 microL of NEBuffer 4 (50 mM potassium acetate, 20 mM Tris acetate, 10 mM magnesium acetate, 1 mM dithiothreitol, pH 7.9) plus 100 microgram/ml BSA. 1 unit of N.BbvCI activity is the least amount of enzyme that completely converts 1 microgram of supercoiled pUB DNA into the open-circular form in 1 h at 37° C. in 50 microL in the same buffer. These enzymes were homogeneous by SDS-PAGE, and had a final protein concentration of approximately 40 mg/ml.

FIG. 17. Properties of enzymes with mutated $R_1$-subunit catalytic sites. The mutant isolate number is given in column 1. The nt. sequence of the section of the $R_1$ gene coding for the subunit-1 catalytic site in each isolate is given in column 2 (SEQ ID NO:13 through SEQ ID NO:35), and the amino acid sequence is given in column 3. In all of the isolates, subunit 1 was mutated at the active site, and subunit 2 was normal ('+' in column 4). The catalytic activities of crude cell extracts of these enzymes are shown in column 5–7. A '√' in column 5 signifies that the enzyme cleaves DNA (e.g. 1–5); a '√' in column 6 signifies that it nicks DNA (e.g. 1–4); and a '√' in column 7 signifies that it is inactive and neither cleaves DNA nor nicks it (e.g. 1–14). A '(√)' in column 6 indicates that the enzyme displays very weak nicking activity (e.g. 1–45). The symbol 'Mn' in column 5 signifies that the enzyme cleaves DNA in the presence of 10 mM manganese chloride (e.g. 1–29).

Figure 1:
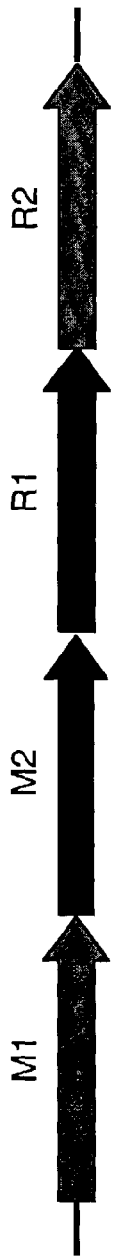
FIG. 1. Nucleotide sequence of the BbvCI restriction and modification genes (SEQ ID NO:1).

FIG. 18. Properties of enzymes with mutated $R_2$-subunit catalytic sites. The mutant isolate no. is given in column 1. The nt. sequence of the section of the $R_2$ gene coding for the subunit-2 catalytic site in each isolate is given in column 2 (SEQ ID NO:36 through SEQ ID NO:63), and the amino acid sequence is given in column 4. In all of the isolates, subunit 2 was mutated at the active site, and subunit 1 was normal ('+' in column 3). The catalytic activities of crude cell extracts of these enzymes are shown in column 5–7. A '√' in column 5 signifies that the enzyme cleaves DNA (e.g. 2–39); a '√' in column 6 signifies that it nicks DNA (e.g. 2–2); and a '√' in column 7 signifies that it is inactive and neither cleaves DNA nor nicks it (e.g. 2–5). A '(√)' in column 6 indicates that the enzyme displays very weak nicking activity (e.g. 2–49). The symbol 'Mn' in column 5 signifies that the enzyme cleaves DNA in the presence of 10 mM manganese chloride (e.g. 2–56).

DETAILED DESCRIPTION OF INVENTION

In its preferred embodiment, the method involves the following steps. 1) Identifying a restriction endonuclease that possesses two different catalytic sites. 2) Cloning and sequencing the gene(s) for that endonuclease, together, if necessary, with the gene(s) for protective modification enzyme(s). 3) Identifying the amino acid residues within the endonuclease that form at least one of the catalytic sites for DNA strand-hydrolysis. 4) Altering one or more of the catalytic site residues by changing the nucleotides that code for them in the endonuclease gene(s). 5) Isolating clones that express altered restriction endonucleases, and identifying those that remain active, but now nick DNA at the recognition sequence rather than cleave it. These steps are described in detail below.

1. Identifying Endonucleases with Two Different Catalytic Sites

Over three thousand restriction endonucleases have been discovered and characterized from a wide variety of bacteria and archae. Comprehensive lists of their recognition sequences and cleavage sites can be found at REBASE (http://rebase.neb.com). In the majority of restriction enzymes, the two catalytic sites are likely to be identical, because the enzymes either bind to DNA as homodimers, or they bind with some other organization but form homodimers transiently to accomplish DNA cleavage. Certain enzymes however possess two different catalytic sites and do not homodimerize.

The kinds of nucleotide sequences to which proteins bind reflects their organizations. Proteins that bind to symmetric ('palindromic') sequences do so because they, themselves, are symmetric (e.g. EcoRI: GAATTC). Proteins that bind to asymmetric nucleotide sequences, conversely, do so because they are asymmetric (e.g. FokI: GGATG). Since restriction enzymes that possess two different catalytic sites are generally asymmetric, it follows that the sequences to which they will bind will be asymmetric to match. The first step in identifying endonucleases likely to possess two different catalytic sites, then, is to eliminate from the list of all enzymes those that recognize symmetric nucleotide sequences. The next step is to eliminate enzymes that probably homodimerize to accomplish DNA cleavage. This includes the Type I endonuclease-methyltransferases (e.g. EcoKI: AACNNNNNNGTGC), and the Type IIf endonuclease-methyltransferases (also referred to as Type IV; e.g. BcgI: CGANNNNNNTGC) that recognize discontinuous asymmetric sequences. Eliminated, too, are the Type III endonucleases (e.g. EcoP1I: AGACC) that recognize continuous asymmetric sequences but cleave only when two such, opposed, sequences are present in the DNA (Humbelin et al., *J. Mol. Biol.* 200:23–29 (1988); Meisel et al., *Nature.* 355:467–469 (1992)). However Type IIs endonucleases for which experimental evidence of homodimerization exists may be modified to provide nicking endonucleases (Example 3).

When endonucleases bind to DNA asymmetrically but cleave by homodimerization, only one component of the homodimer binds to the local recognition sequence. The other component contributes the second catalytic site and some non-specific binding energy, but it is thought to perform no nucleotide sequence-discrimination. The greater the separation between the recognition sequence and the hydrolysis sites on the DNA molecule, the easier it is to envisage this happening. When the hydrolysis sites are within the recognition sequence, or just outside, it seems unlikely that the enzyme would be symmetric, overall, but rather that it would be asymmetric, and would thus possess two different catalytic sites. We consider restriction endonucleases that recognize continuous, asymmetric sequences, and cleave within those sequences or very close to them, to be the ones most likely to possess two different catalytic sites. These enzymes are variously referred to as Type IIt or Type IIq endonucleases, or as atypical Type IIs endonucleases (Kessler and Holtke, *Gene*. 47:1–153 (1986); Degtyarev et al., *Nucleic Acids Res*. 18:5807–5810 (1990); Stankevicius et al., *Nucleic Acids Res*. 26:1084–1091 (1998); Degtyarev et al., *Nucleic Acids Res*. 28:e56 (2000)).

Thirteen kinds of restriction endonucleases currently fall into this category (FIG. 15). Seven—represented by AciI, BbvCI, Bpu10I, BsrBI, BssSI, BtrI, and GdiII—hydrolyze both strands of DNA within their recognition sequences, and these seem to us to be the most promising candidates of all for conversion to nicking enzymes by the present invention. Three more—represented by BsmI, BsrI, and SimI—hydrolyze one strand within the recognition sequence and one strand just outside, and the remaining three—represented by BsrDI, BstF5I, and BtsI—hydrolyze both strands just outside the recognition sequence. These last six kinds of endonucleases are also promising candidates for conversion to nicking enzymes. Among endonucleases for which the separation between the recognition sequence and hydrolysis sites is substantial are two, BbvI and BstNBI, that possibly act as heterodimers (see Example 2). If they indeed act this way, then they and other Type IIs endonucleases like them are also candidates for conversion to nicking enzymes.

Enzymes are composed of functional parts: one part binds a substrate, for example, another binds a co-factor, and a third catalyzes a chemical transformation. These parts associate with one another in the final enzyme but whether they do so as separate subunits or as interconnected domains of a larger, composite, protein does not, in principal, affect the outcome. In the course of evolution, genes encoding proteins that interact often migrate to adjacent loci in the genome. Sometimes, these neighboring genes then fuse, head-to-tail, to form one continuous gene that incorporates the ancestral proteins into a single polypeptide chain. When this happens, what was originally a multimeric protein of different subunits becomes a monomeric protein of several domains.

Restriction endonucleases that are catalytically asymmetric are likely to act either as heterodimers, comprising two different protein chains, or monomers, comprising a single protein chain. Bpu10I (FIG. 15) is reported to be a heterodimer (Stankevicius et al., *Biologija*. 2:51–53 (1996)). BbvCI, we show here, is also a heterodimer (see Example 1). BstNBI and BbvI might be heterodimers, too. In contrast, AciI, BsrI, BsrBI, and BssSI, are monomers. In the compact, Type IIt, variety of heterodimer, both subunits will likely perform nucleotide sequence recognition as well as catalysis, and so the subunits of this kind of enzyme will likely be of similar size, approximately 200–350 amino acids (aa) apiece. In contrast, in the extended, Type IIs, variety of heterodimer, both subunits will likely perform catalysis, but only one will perform sequence recognition, and consequently the subunits will differ in size, the small subunit being approximately 150–250 aa, the other being 2–3 times larger, or approximately 400–650 aa. Although the true subunit stoichiometry in heterodimers is 1:1, subunit dissociation can occur during enzyme purification resulting in a different apparent subunit stoichiometry in purified enzyme preparations.

The genes for the two subunits of heterodimeric restriction endonucleases will likely lie next to each other in the genomes, and in the same orientation. For Type IIt enzymes, the two genes will be similar in length. For Type IIs enzymes they will be different, one being 2–3 times longer than the other. Gene fusion could join the genes for the two subunits together, and so these endonucleases could also exist as monomers. The molecular masses of such monomers would be roughly the sum of the masses of the ancestral subunits, that is to say between approximately 450 and 900 aa. The specific activity of such monomers would be in the range typical for Type II and Type IIs enzymes, and considerably higher than those of partially dissociated heterodimers.

Heterodimeric restriction endonucleases may be recognized (i) by analysis of endonuclease purified from the original organism or from a recombinant host containing the cloned restriction system, or (ii) by sequence analysis of the cloned restriction system. In the former case, the purified endonuclease may be characterized by electrophoresis on SDS-PAGE, which will usually reveal the presence of two protein components migrating at different positions. It may be the case that the two subunits, although distinct in sequence and the products of different genes, will migrate at the same mobility on SDS-PAGE. This situation can be recognized because the apparent molecular weight derived from SDS-PAGE analysis will be one-half of the apparent molecular weight derived from gel-filtration analysis. Further, N-terminal amino acid sequence analysis of the purified endonuclease will reveal the presence of two different amino acids at each sequencing cycle, in the apparently single band. Procedures for determining these properties are well known in the art, and are disclosed for example in Current Protocols in Protein Analysis (sections 8.3, 10.1, and 11.10; Coligan, F. E., Dunn, B. M., Ploegh, H. L., Speicher, D. W., and Wingfield, P. T. *Current Protocols in Protein Science*, John Wiley and Sons, (1997)).

In the latter case, the restriction systems amenable to this invention will contain up to four open reading frames (ORFs), two encoding methyltransferases, and two encoding the subunits of the restriction endonuclease. The methyltransferase ORFs may be recognized by amino acid sequence comparisons according to (Wilson, *Methods Enzymol*. 216:259–279 (1992) and Malone, et al., *J. Mol. Biol*. 253:618–632 (1995)). Additional ORFs may also be present including those encoding proteins involved in the regulation of gene expression (such as C proteins), and in the repair of base-mismatches resulting from the deamination of 5-methylcytosine (such as Vsr proteins).

Genes encoding subunits of the endonuclease may be verified by creating expression clones in which the methyltransferase genes are carried on one plasmid, and the candidate endonuclease genes are carried on one or more additional plasmid(s), as disclosed in Brooks, et al. (U.S. Pat. No. 5,320,957). The presence of just the methyltransferase plasmid will cause the DNA within the cell to become resistant to action of the endonuclease, but the cells will express no endonuclease activity. Addition of the endonuclease genes on the additional plasmid(s) will cause the cells to express endonuclease activity. In some situations it may be possible to express the endonuclease genes in the absence of the methyltransferase genes, as disclosed in International Publication No. WO 99/11821.

The requirement for both ORFs for endonuclease activity of heterodimeric enzymes may be verified by creating expression clones in which each of the ORFs can be expressed separately, e.g. by placing each ORF on a separate compatible plasmid, or by placing each ORF under the control of a promoter that can be induced separately (e.g. inducible by lactose or by arabinose), and then testing for expression of the endonuclease when only one ORF is present or only one ORF is expressed. Endonuclease activity will be obtained only when both ORFs are expressed. It may also be possible to reconstitute activity by mixing extracts from two recombinant hosts expressing each ORF separately. The requirement for both ORFs may alternatively be verified by creating deletion or insertion mutations in each of the candidate ORFs separately, and then assessing the endonuclease activity of the resulting recombinant host. For heterodimeric enzymes, both wild-type ORFs will be required for expression of the active endonuclease.

2. Cloning the Restriction Endonuclease Gene(s)

Methods for cloning genes encoding restriction endonucleases are well-established, and are described in numerous publications and patents (Howard et al., *Nucleic Acids Res*. 14:7939–7951 (1986); Brooks et al., *Gene*. 74:13 (1988); Lunnen et al., *Gene*. 74:25–32 (1988); Brooks and Howard, U.S. Pat. No. 5,320,957). These methods will not be repeated here.

Restriction genes have the capacity to harm cells because the endonucleases they encode can cleave the cell's own DNA. A degree of DNA cleavage can be repaired, but an excess leads to chromosome disintegration and cell death. In order to clone a restriction gene, then, precautions must generally be taken to avoid excessive DNA cleavage. These precautions include maintaining the restriction gene in a non-functional condition; maintaining it in a functional but unexpressed condition; and, protecting the DNA from cleavage by site-specific modification. The latter measure, achieved by cloning into the cell contemporaneously the genes for appropriate modification methyltransferase enzymes, is the preferred one, although under-expression of the endonuclease gene(s), by the use of vectors such as that described in International Publication No. WO 99/11821 can be a useful supplement in cases where complete DNA modification proves difficult to achieve.

Since the restriction enzymes with which we are concerned, here, recognize asymmetric DNA sequences, two methyltransferases will usually be required to protect the DNA of the host from cleavage, one for modifying each strand of the recognition sequence. Preferably, these methyltransferases will be the 'cognate' enzymes that accompany the restriction endonuclease naturally, in the cell from which it derives, but hetero-specific methyltransferases might be used as an alternative (Wilson and Meda, U.S. Pat. No. 5,246,845). The genes for pairs of cognate methyltransferases usually lie next to each other in the genome. In some instances they occur as separate proteins (e.g. the BbvCI system; see Example 1), and in other instances they are fused together (e.g. FokI (Looney et al., *Gene*. 80:193–208 (1989); Sugisaki et al., *J. Biol. Chem*. 264:5757–5761 (1989)). The gene(s) for the endonuclease usually lies alongside the genes for its cognate methyltransferases, and the entire set can usually be cloned on one continuous section of DNA. Methyltransferases range in length between 350 aa to 700 aa, and so two methyltransferases will require approximately 2–4 kb of genetic coding capacity. The endonuclease gene(s) requires 1.5–3 kb of coding capacity more, and so the total amount of DNA that needs to be cloned to isolate the complete restriction-modification system is expected to be 3.5–7 kb. Of course, larger and smaller values are also possible.

Cloning the gene(s) for the cognate methyltransferases is preferred for two reasons: once cloned, they can serve to protect the new host cell from harm when the endonuclease is present; and, because the genes for endonucleases and methyltransferases usually lie next to each other, and the latter can be recognized and selected-for rather easily, methyltransferases 'flag' the locations of endonuclease genes within genomes, simplifying their subsequent cloning. Cloning the gene(s) for the methyltransferases, although preferred, might not be essential, however. If the endonuclease is a heterodimer, and neither subunit alone manifests catalytic activity, the genes for the subunits could be cloned individually in the complete absence of DNA modification. In such cases, the active enzyme could be assembled subsequently, in vitro, by mixing together preparations of the individual subunits.

Nicks in DNA are repaired more readily in cells than are double-strand breaks, and so DNA-nicking enzymes are likely to be less harmful to unmodified cells than are DNA-cleaving enzymes. Consequently, it might be possible to maintain a nicking endonuclease in a functional, expressed, state within an under-modified host cell, and especially if the cell overexpressed a DNA ligase enzyme to repair the nicks. In this event, engineered nicking endonucleases might be maintained and expressed in cells in the complete absence of methyltransferases.

3. Identifying the CATALYTIC Sites

Most restriction endonucleases bind a divalent cation—manganese or magnesium—at each of their catalytic sites. The cation plays an essential role in activating the water molecule which then hydrolyses the phosphodiester section of the DNA backbone to cause its rupture. The structures of the catalytic sites of several restriction endonucleases, determined by x-ray crystallography, establish that these cations are held in place in the enzyme by coordination to the side-chains of two acidic amino acids, either aspartate (D) or glutamate (E). Usually, the coordinating acidic residues are separated in the protein by a loop of variable length—10 to 30 amino acids—and sequence. Proline (P) sometimes precedes the first acidic residue, and lysine (K) usually follows the second acidic residue, 2 or more residues later in the sequence (FIG. 1). The acidic residues, and the lysine are essential for catalysis; substitution of either by uncharged amino acids renders the catalytic sites inert. Based on a few examples, a loose catalytic site motif for restriction endonucleases has been defined as PD . . . 10-25 . . . EXK . . . , where X is hydrophobic.

Inspection of the amino acid sequences of restriction endonucleases reveals a PD-EXK motif to be present in some of them, hinting that these amino acids might form the catalytic sites in these enzymes. The amino acid sequences of restriction endonucleases vary greatly, however, and because of this variability, it often not possible to identify this motif with any degree of certainty by mere inspection of the sequence. In these cases, a combination of computer programs that predict protein structure, and that 'thread' unknown sequences through known structures, can be used to narrow the range of possibilities (on-line ref.). Since amino acids critical to enzyme function are those most resistant to change during evolutionary divergence, global amino acid sequence alignments between related endonucleases can be used to identify conserved regions within which the catalytic site residues are likely to lie. Experimental approaches, based on Fenton chemistry for example, can also be used to roughly locate the catalytic site residues within an endonuclease.

If the restriction endonuclease is a heterodimer, one set of catalytic site residues will likely be present in one subunit, and a second set will likely be present in the other subunit. If the endonuclease is a monomer, one set of catalytic site residues will likely be present in the amino-terminal half of the protein, and a second set will likely be present in the carboxy-terminal half. It is not necessary to identify both sets of catalytic site residues in order to practice the present invention; one set is sufficient if the strand-specificity of the resulting nicking enzyme is immaterial.

4. Catalytic Site Mutagenesis.

If the likely catalytic site residues within the endonuclease can be identified, one or more of them is targeted for site-specific mutagenesis. Site-specific mutagenesis may be performed using a defined oligonucleotide to create a specific substitution—alanine, for example—or a degenerate oligonucleotide to create a variety of different substitutions. The D, E, and K residues are primary targets for mutagenesis; the neighboring residues are secondary targets. Changes in the former are expected to abolish catalytic activity because these residues are critical to the catalytic mechanism. Changes in the latter are likely to have less predictable, and possibly intermediate effects, because these residues affect the spatial relationships between the catalytic residues rather than the catalytic residues, themselves.

The goal of the mutagenesis is to inactivate the catalytic site without perturbing the rest of the enzyme. The mutated subunit, or domain, must fold and associate with the other properly; the assembled enzyme must bind to the recognition sequence properly; and the unaltered catalytic site must continue to function properly. Our preferred approach is to perform site-directed mutagenesis using degenerate oligonucleotides that create an array of different mutants, and then to screen among these individually to identify those that behave as we wish.

Once synthesized, the mutagenic oligonucleotide can be used on its own using the Kunkel mutagenesis procedure, for example, or it can be used together with a reverse primer in a PCR amplification procedure. If the amino acid residues comprising the catalytic sites of the endonuclease cannot be identified unambiguously, but can be narrowed down to a number of possibilities, then mutagenic oligonucleotides can be synthesized to alter each of these possible sites in turn with the expectation that one or other of them will prove to be correct.

In the event that the catalytic site residues cannot be identified with any confidence, a strategy of non-targeted mutagenesis of the endonuclease gene(s) can be adopted. Alanine scanning of the acidic residues in the protein(s) can be performed in vitro, or 'dirty' PCR could be used to create mutations at random. Random mutagenesis could also be performed in vivo by propagating the cloned endonuclease gene in a mutator host such as mutD, or in the presence of chemical mutagens such as 2-aminopurine, or nitrosoguanidine, or during exposure to ultraviolet radiation, or ionizing radiation. Random mutagenesis can be also performed in vitro by reacting the DNA with hydroxylamine, or by amplifying it under conditions that favor base mis-incorporation. Other procedures, such as transposon-mediated insertion mutagenesis, may also be used although they might be less successful because the changes they induce are liable to alter the protein structure, and render the enzyme inactive.

5. Screening for Nicking Activity.

Following mutagenesis, individuals are examined to establish the catalytic activities of the endonucleases they encode. Three outcomes are expected: some enzymes will continue to catalyze DNA cleavage; others will be entirely inactive; and yet others will display the desired nicking activity. The preferred method for distinguishing between these three types is to assay crude preparations of the enzymes on a supercoiled plasmid DNA substrate that contains two or more recognition sites for the enzyme. Plasmid DNA molecules migrate at different rates during electrophoresis depending upon their topologies. The naturally occurring, negatively supercoiled, form migrates more rapidly than the full-length, linear, form, which in turn migrates more rapidly than the nicked, 'open-circular' form. These three topological forms separate during high-resolution gel electrophoresis, and the proportion of each in a sample can be assessed from the relative intensities of the corresponding bands.

Clones expressing mutant enzymes are cultured individually, harvested by centrifugation, and resuspended in a small volume of buffer. The resuspended cultures are sonicated to disrupt the cells, and the insoluble material is removed by centrifugation. Aliquots of the cell extracts are then incubated with supercoiled plasmid DNA in digestion buffer. If the endonuclease is heterodimeric, it is feasible to clone and mutagenize the subunits separately, and to reconstitute the mutant enzymes in vitro, by mixing together the subunits at the time that the assay is performed, or beforehand. Following incubation, the digested plasmid DNA is de-proteinized, and then electrophoresed through an agarose slab gel in the presence of ethidium bromide. Control preparations of undigested, nicked, linear, and cleaved plasmid DNA are electrophoresed in separate lanes alongside the samples to facilitate interpretation of the results. Following electrophoresis, the gel is illuminated with ultraviolet light and photographed.

Nicking endonucleases are identified by their ability to convert supercoiled DNA to the open-circular form, without the formation of linear molecules or fragments. Once such enzymes are identified, the nicking activity is characterized. The continued sequence-specificity of the enzyme is checked on a supercoiled plasmid DNA substrate that contains no recognition sites. No nicking should be seen; incubation with the enzyme should not alter the relative amounts of the supercoiled, linear, and open-circular forms present naturally in the DNA sample.

The sequence-specificity and the strand-specificity of the endonuclease is then characterized by analysis of its nicked DNA products. The enzyme is incubated with a DNA molecule containing one or more recognition sites. The DNA is purified and sequenced in both directions across the nick site. When a nick is present in the template strand, the sequencing ladder stops abruptly at the nick. When a nick is present in the complimentary, non-template strand, the sequencing ladder is unaffected. Sequencing across a nick, then, produces a continuous ladder in one direction and a discontinuous ladder in the other direction. The ladder that is discontinuous reveals which strand of the DNA contains the nick, and the position of the discontinuity within the ladder reveals the position of the nick within the sequence. Nicking should occur only at the recognition sequence, and only once per occurrence of the recognition sequence. Only one strand should become nicked, and the position of that nick should be the same as one or other of those catalyzed by parental, cleaving enzyme.

If only a small number of mutants need to be screened, as would occur if mutagenesis were targeted to just the catalytic site residues, then individual clones can be selected at random and examined in turn. If a large number of clones need to be screened, however, as would occur if mutagenesis were non-targeted, then an initial round of screening in vivo is preferred to identify the rare individuals likely to synthesize a nicking enzyme. In vivo screening might be achieved using an unmodified bacterial host that induced the expression of a reporter gene in response to DNA damage. Provided the endonuclease is well-expressed, cells receiving a normal enzyme will likely die due to excessive DNA cleavage. Cells that receive a nicking enzyme, or an inactive enzyme will likely survive, but only the former will express the reporter gene. The reporter gene can be chosen to render the cells resistant to an antibiotic, or independent of some nutritional requirement, in which cases cells carrying a nicking endonuclease can be isolated selectively. Or, the reporter gene can be chosen to give a chromogenic or fluorescent signal upon expression, in which case cells carrying a candidate nicking endonuclease can be recognized by their coloration. Once potential nicking mutants have been identified in vivo, the catalytic properties of their endonucleases can be examined in vitro.

The present invention is further illustrated by the following Examples. These Examples are provided to aid in the understanding of the invention and are not construed as a limitation thereof.

The references cited above and below are herein incorporated by reference.

EXAMPLE 1

Engineered Nicking Derivatives of BbvCI 1.0 Overview

Figure 13:
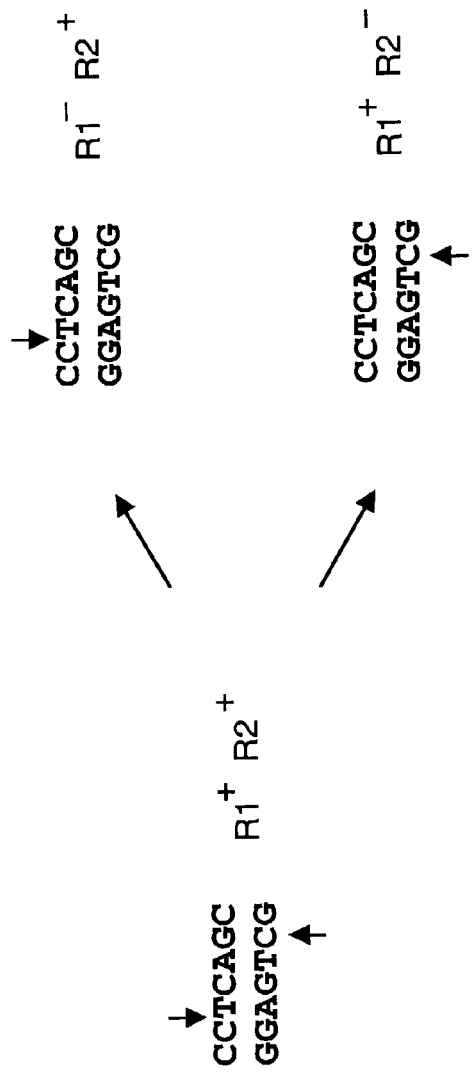
FIG. 13. Application of method for conversion to nicking endonucleases of the restriction endonuclease R.BbvCI. R.BbvCI is composed of two different subunits, R1 and R2, each of which contains one catalytic site for DNA strand-hydrolysis. R.BbvCI (composition: $R_1^+:R_2^+$) cleaves duplex DNA at its recognition site by hydrolyzing the two strands of the duplex simultaneously, one catalytic site inducing cleavage of each strand. In turn, each catalytic site in R.BbvCI was inactivated to produce two novel nicking endonuclease of composition $R_1^-:R_2^+$ and $R_1^+:R_2^-$.

The method for forming a nicking endonuclease starting with restriction endonuclease R.BbvCI is summarized in FIG. 13. Nicking enzyme derivatives of R.BbvCI are obtained by inactivating the active site for cleavage in either subunit of this heterodimeric endonuclease without interfering with the proper subsequent assembly of the enzyme. Appropriate mutations in the enzyme can be created by making mutational changes in amino acids, individually or in combination, that comprise the active site, or that influence its chemistry or organization; and then assessing the nicking activity of enzyme produced by each mutant. The magnitude of this effort may be reduced by focusing on regions conserved in several different but related enzymes. In one preferred embodiment, changes are introduced by the steps of:

1.0.1 Identifying a conserved region by alignment of several members of this class of enzymes. Conceptual translations of five genes were employed: the two subunits of BbvCI, termed BbvCI-$R_1$, BbvCI-$R_2$, and three conventional homodimeric Type II endonucleases that recognize related, palindromic, sites: Bsu36I, BlpI, and DdeI. These genes exhibit limited homology in discrete, conserved, blocks. One conserved block contained the sequence EXK. This motif was judged to be the likely active site for cleavage, in which changes may be expected to abolish cleavage but still enable assembly of a conformationally native complex in which the other subunit would still be able to cleave. These were judged favorable sites for mutagenesis.

1.0.2 Generating mutations within the favorable region by cassette mutagenesis. This process comprised the steps of:

a) designing two mutagenic primers for inverse PCR, one for each gene, bbvCIR$_1$ and bbvCIR$_2$. These mutagenic primers were designed such that the nucleotides encoding the EXK motive included 20% random nucleotides, and 80% the correct nucleotide at each of the nine positions. In each mutagenic primer, the region encoding the EXK motif was flanked by the unique sequence of the respective gene;

b) conducting mutagenic PCR (as disclosed in *Molecular Cloning, A Laboratory Manual*, Sambrook, J. and Russel D. W., Cold Spring Harbor Laboratory, pp 8.81–8.95 (2001)) employing in separate reactions i) one mutagenic primer for bbvCIR$_1$ and a unique primer directed in the opposite direction from the mutagenic primer and immediately to its 5' side; and ii) one mutagenic primer for bbvCIR$_2$ and a unique primer directed in the opposite direction from the mutagenic primer and immediately to its 5' side, such that the entire plasmid vector was amplified;

c) ligating the PCR products to form a population circular molecules;

d) transforming an appropriate host (expressing both methyltransferases) separately with the two mutagenized populations targeting bbvCIR$_1$ and bbvCIR$_2$ to obtain colonies on selective plates; and e) for isolated members of each population, testing for cleavage activity in crude extracts, by the steps of:
  i) growing cultures of the candidate colonies;
  ii) centrifuging the cultures to obtain cell pellets;
  iii) resuspending the cultures in lysis buffer;
  iv) lysing the resuspended cultures and clarifying them by centrifugation;
  v) withdrawing aliquots of the clarified extracts to assay tubes containing substrate plasmid DNA and digestion buffer;
  vi) incubating the assay tubes to allow enzyme-induced cleavage to occur; and
  vii) separating the plasmid DNA products by high-resolution gel electrophoresis and assessing whether no cleavage, single-strand cleavage, or double-strand cleavage, has occurred.

Ideally, the substrate DNA is a plasmid that contains two or more well separated sites for cleavage. Under such circumstances, extracts containing inactive enzyme do not substantially alter the mobility of the various forms of the plasmid. Extracts containing wild-type enzyme abolish the supercoiled, linear, and open-circular forms of the plasmid and produce two (or more) linear fragments in their place. And extracts containing nicking enzyme abolish the supercoiled plasmid form, converting it to open-circular form, without affecting the linear form 1.0.3 Testing mutants that appear to nick by alternative procedures to confirm that they have this activity. Such procedures include, but are not limited to, sequencing through nicked sites and sequential nicking with complementary mutants, each defective in the activity of one of the two subunits. Most preferably, candidate enzymes are tested by the first procedure, comprising the steps of:

a) incubating DNA containing at least one site for cleavage with purified or semi-purified enzyme;

b) purifying this DNA; and c) using it as a substrate for DNA sequencing across the site in both directions.

Nicking is indicated when the sequence in one direction continues across the site (i.e., the template strand is continuous) while the sequence in the other direction terminates abruptly at the site (i.e., the other strand is interrupted by a nick).

In the second procedure, extracts of mutants thought to nick different strands are mixed together and the mixture is assayed for double-strand cleavage activity. While neither enzyme alone should catalyze double-strand cleavage, the mixture should be able to do so, either as a result of double-nicking, first on one strand by one enzyme, then on the complementary strand by the other, or by reassociation of the unmutated subunit of each enzyme to produce a fully-wild-type enzyme.

In this manner mutations in BbvCI-R$_1$ and BbvCI-R$_2$ are identified that enable cleavage of one strand but not the other at BbvCI sites. Two such representative nicking mutants are designated BbvCI #1-37 and BbvCI #2-12.

1.1 The Choice of BbvCI

BbvCI is a Type IIt restriction endonuclease synthesized by the bacterium *Bacillus brevis* C. It recognizes an asymmetric, seven base-pair nucleotide sequence in DNA, and cleaves symmetrically within this sequence two bases in from each of the 5' ends:

5'-C C^T C A G C-3'
3'-G G A G T^C G-5'

The unusual ability of BbvCI to cleave within a sequence that is asymmetric suggested to us that the subunits, or domains, of this enzyme might differ. Hence BbvCI is a candidate for conversion to a nicking enzyme by the present invention.

1.2 Cloning the BbvCI Restriction Endonuclease Genes 1.2.1 Vector preparation: To permit the BbvCI genes to be cloned by the 'methylase-selection' method, plasmid vector pUC19 was modified prior to library construction by insertion of two BbvCI sites. The first site was inserted between the AatII and EcoO109I sites in the vector, and the second between the two TfiI sites. 1.6 microgram of pUC19 DNA was digested with 20 units each of AatII (NEB Product # R0117, New England Biolabs, Inc., Beverly, Mass.) and EcoO109I (NEB Product # R0503, New England Biolabs, Inc., Beverly, Mass.) in 50 microL of NEBuffer 4 (50 mM potassium acetate, 20 mM Tris acetate, pH 7.9, 10 mM magnesium acetate, 1 mM dithiothreitol) plus 100 microgram/ml BSA for 1 h at 37° C. The following pair of complimentary oligonucleotide linkers were synthesized:

```
bvcpuc-1 (NEB #193-44)
5'-GGCCTCAGC-3' bvcpuc-2 (NEB #193-44)
5'-GGCGCTGAGGCCACGT-3'        (SEQ ID NO:64)
```

The oligonucleotides were suspended in MQ water (autoclave-sterilized, Millipore Q UV-plus, water) to 40 micromolar, and 10 microL of each was added to the restriction enzyme digestion, together with 8 microL of 10×T4 DNA ligase buffer (500 mM Tris-HCl, pH 7.5, 100 mM magnesium chloride, 100 mM dithiothreitol, 10 mM ATP, 250 microgram/ml BSA) and 800 u (2 microL) of T4 DNA ligase (NEB Product # M0202; New England Biolabs, Inc., Beverly, Mass.). After 1 h at room temperature, 1 microL of the reaction was used to transform competent *E. coli* ER2502. The transformed cells were plated onto L-Broth agar plates containing Ampicillin, and incubated overnight at 37° C. Individual colonies were inoculated into 10 ml L-Broth+ Ampicillin, grown overnight, and plasmid DNA was mini-prepped from each. The plasmids were digested with BbvCI (NEB Product # R0601, New England Biolabs, Inc., Beverly, Mass.) to identify those containing the inserted BbvCI site. One of these, PUB-AE, was used as the substrate for inserting the second BbvCI site. PUB-AE was digested with 8 u TfiI (NEB Product # R0546, New England Biolabs, Inc., Beverly, Mass.) for 1 h at 65° C., and the following pair of complimentary oligonucleotide linkers were added, as before, together with 8 microL of T4 DNA ligase buffer and 3 microL of T4 DNA ligase:

```
bvcpuc-3 (NEB #193-63)
5'-AATGGCCCTCAGCC-3'        (SEQ ID NO:65)

bvcpuc-4 (NEB #193-64)
5'-ATTGGCTGAGGGCC-3'        (SEQ ID NO:66)
```

After incubation at room temperature and subsequent transformation, plasmids containing two BbvCI sites were identified. One of these, designated pUB, was purified by the cesium chloride-ethidium bromide gradient method (Sambrook, Fritsch, and Maniatis, *Molecular Cloning*, Cold Spring Harbor Laboratory Press, 1989, pp. 1.42–1.46.) and used as the vector for the *B. brevis* DNA libraries.

1.2.2 *B. brevis* DNA Preparation: 5 g of *B. brevis* NEB 1030 cell paste was resuspended in 20 ml of 25% sucrose, 50 mM Tris, pH 8.0. 10 ml of 0.25 M EDTA, pH 8.0, was added followed by 60 mg of lysozyme in 6 ml of 0.25 M Tris, pH 8.0. The cells were incubated on ice for 1 hr and then lysed by the addition of 24 ml of 1% Triton X-100, 50 mM Tris pH 8.0, 62.5 mM EDTA, followed by 5 ml of 10% SDS. 70 ml of phenol (equilibrated to pH 8.0) and 60 ml of chloroform was added, and the lyzate was gently emulsified. The emulsion was centrifuged to to separate the phases, and the viscous upper layer containing the DNA was withdrawn and extracted a second time with phenol and chloroform. The centrifuged upper layer was withdrawn and dialyzed for 24 hr at 4° C. against several changes of 10 mM Tris, 1 mM EDTA, pH 8.0. The dialyzed DNA was digested at 37 ° C. for 1 hour with RNase A at a final concentration of 100 microgram/ml, and then the DNA was precipitated by the addition of NaCl to a final concentration of 0.4 M, and 0.55 vol of 100% isopropanol. The precipitated DNA was spooled out of solution on a glass rod, air-dried, and then re-dissolved in 10 mM Tris, 1 mM EDTA, pH 8.0. This procedure yielded 4 ml of high-molecular-weight DNA at a concentration of 200 microgram/ml.

1.2.3 *B. brevis* library preparation: Purified *B. brevis* DNA was separately digested with AciI (NEB Product # R0551, New England Biolabs, Inc., Beverly, Mass.), BstYI (NEB Product # R0523, New England Biolabs, Inc., Beverly, Mass.), ClaI (NEB Product # R0197 New England Biolabs, Inc., Beverly, Mass.), HpaII (NEB Product # R0171, New England Biolabs, Inc., Beverly, Mass.), and Sau3AI (NEB Product # R0169, New England Biolabs, Inc., Beverly, Mass.). The digested DNAs were ligated with appropriately cleaved pUB vector DNA and used to transform *E. coli*. Populations of transformants were cultured in L-broth plus ampicillin, and the plasmids they harbored were purified by CsCI-ethidium bromide gradient centrifugation.

1.2.4 Selective digestion: 2 microgram of each purified plasmid library was digested with 10 u of BbvCI for 4 h at 37° C. The digestions were transformed into *E. coli* and plated on LB agar plates containing Ampicillin. Transformant colonies were picked individually and cultured, and their plasmids were mini-prepped for analysis.

1.2.5 Clone isolation and analysis: The plasmid minipreps were digested with BbvCI to ascertain their modification status, and with other restriction enzymes to check for common fragments among the inserts. One BbvCI-modified isolate, containing a 3.0 kb ClaI-fragment, was sequenced and found to contain two complete open reading frames, and the beginning of a third. Amino acid sequence analysis of the complete ORFs showed each to code for a 5-cytosine methyltransferase, indicating that these ORFs were the two BbvCI methyltransferase genes. Analysis of the genomic DNA downstream of the incomplete ORF was performed by inverse PCR. Genomic DNA was digested with BsrGI (NEB Product # R0575, New England Biolabs, Inc., Beverly, Mass.), BstYI, HindIII (NEB Product # R0104, New England Biolabs, Inc., Beverly, Mass.), and NciI (NEB Product # R0196, New England Biolabs, Inc., Beverly, Mass.), self-ligated, and then amplified using oligonucleotide primers complementary to DNA sequence within the known region. The PCR products were sequenced directly. 1.6 kb of additional sequence was obtained in this way, completing the first ORF and revealing the presence of a second complete ORF downstream from the first and bearing substantial amino acid sequences homology to it. This suggested that the BbvCI endonuclease was a heterodimer, and that the ORFs were the genes for its two subunits. The nucleotide sequence determined for the BbvCI endonuclease and methyltransferase genes is shown in FIG. 1. The predicted amino acid sequences of the endonuclease and methyltransferase proteins are shown in FIG. 2.

Figure 14:
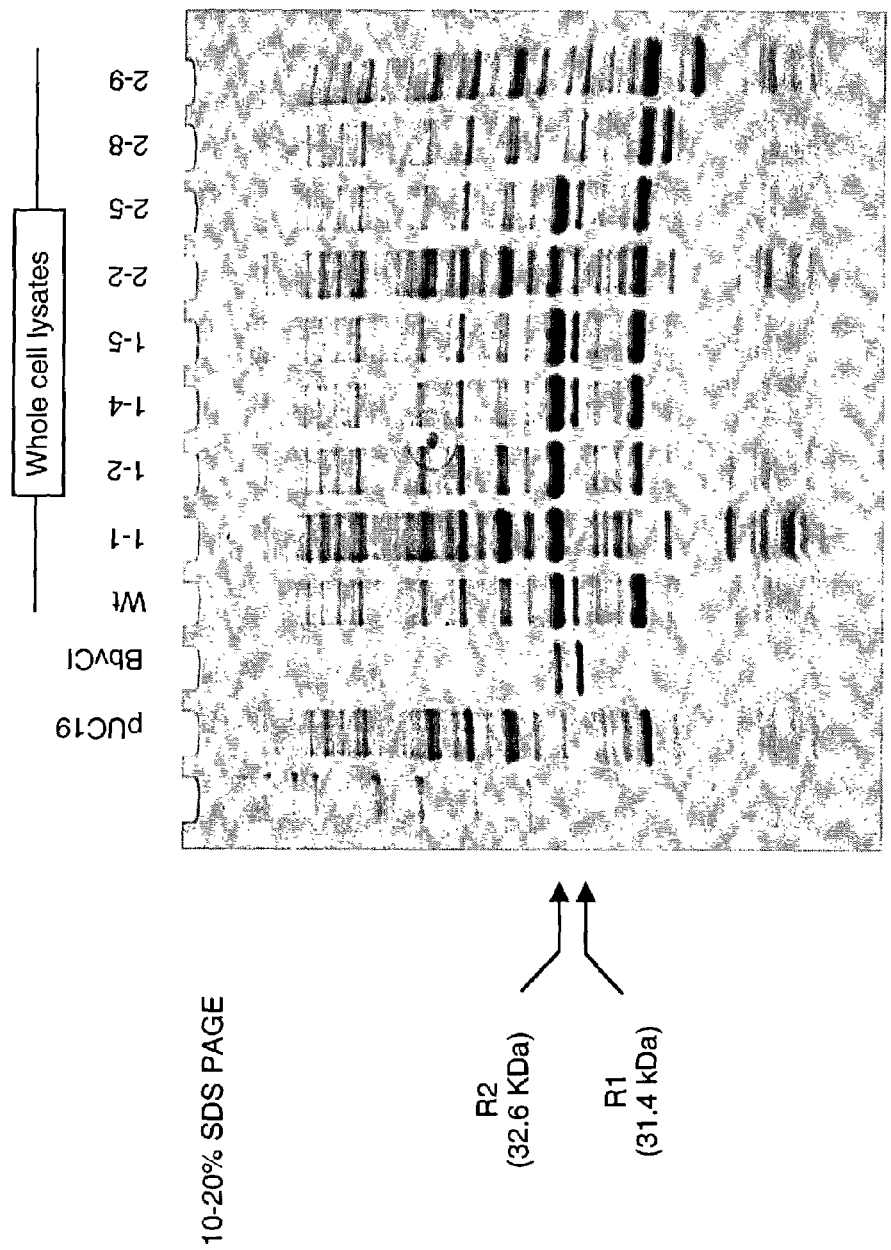
FIG. 14. SDS-PAGE analysis of whole-cell proteins of isolates synthesizing mutant BbvCI enzymes. The two subunits of the enzyme can be easily distinguished. Cells that exhibit R.BbvCI endonuclease activity in crude extracts synthesize both subunits (e.g. Wt; 1–5). Mutant cells that exhibit no endonuclease activity in crude extracts either lack one of the subunits (e.g. 1–2; 2–8), or synthesize subunits that contain incapacitating mutations.

Purified BbvCI endonuclease, analyzed by SDS-PAGE, was found to migrate as two distinct bands of approximately 31 kDa and 32 kDa, the sizes predicted for the products of the ORFs. Deletion analysis demonstrated that the 31 kDa band was the 275-aa subunit encoded by the first, $R_1$, ORF, and that the 32 kDa band was the 285-aa subunit encoded by the second, $R_2$, ORF (FIG. 14). Both ORFs were found to be essential for the expression of endonuclease activity. The amino acid sequences of first few residues of the two subunits were found to match those predicted from the nucleotide sequences of the two ORFs, confirming their identities. The N-terminal sequence of the 31-kDa band was found to be MINEDFFIY . . . , corresponding to the first 9 codons (SEQ ID NO:4) of the $R_1$ gene, and that of the upper, 32-kDa band was found to be MFNQFNPLVY . . . , corresponding to the first 10 codons (SEQ ID NO:5) of the $R_2$ gene.

1.2.6 Expression of the BbvCI endonuclease: To construct a stable expression system for the BbvCI endonuclease, the genes for the BbvCI methyltransferases were first PCR-amplified using the following primers, and ligated into the SacI (NEB Product # R0156, New England Biolabs, Inc., Beverly, Mass.) and SphI (NEB Product # R0182, New England Biolabs, Inc., Beverly, Mass.) sites in the polylinker of the plasmid vector pIH919. pIH919 consists of the LacZ region and polylinker from pUC18, excised with PvuII (NEB Product # R0151, New England Biolabs, Inc., Beverly, Mass.) and HindIII, and ligated into pACYC184 digested with NruI (NEB Product # R0192, New England Biolabs, Inc., Beverly, Mass.) and HindIII.

```
M₁-BbvCI fwd (NEB #205-68)
5'-GGGGCGAGCTCAGGAGGTTAAAATATGGAATCT (SEQ ID NO:67)
GAAACACGTCAAAATATA-3'

M₂-BbvCI rev (NEB #205-69)
5'-GCAATAGCATGCTTACTACCCCCATAATTGTAG (SEQ ID NO:68)
TTGTTCC-3'
```

The resulting plasmid was transformed into *E. coli* ER2688 to create a host cell protectively modified against digestion by the BbvCI endonuclease. The genes for the two BbvCI endonuclease subunits were then PCR-amplified using the following primers, ligated into the SacI and SphI sites of pUC19, and transformed into the protected host.

```
R₁-BbvCI fwd (NEB #205-72)
5'-GGGGGCATGCTAAGGAGGTTTAAAATATGATTA (SEQ ID NO:69)
ACGAGGACTTTTTTATTTAT-3'

R₂-BbvCI fwd (NEB #205-71)
5'-GCAATAGAGCTCTTATTATGGTCGATTAAACAC (SEQ ID NO:70)
TTTACCGCG-3'
```

The resulting strain, E. coli ER2688 containing the bbvCIM₁ and M₂ genes in pACYC184, and the bbvCIR₁ and R₂ genes in pUC19, produced approximately 5 million units of R.BbvCI endonuclease per gram of cells.

1.3 Identifying the CATALYTIC Sites in BbvCI 1.3.1 Analysis of related endonuclease, BlpI and Bsu36I: To assist us in identify the catalytic site residues in the BbvCI endonuclease subunits, two additional restriction endonucleases were cloned and sequenced. Bsu36I and BlpI, homodimeric Type II endonucleases, recognize the symmetric sequences CC^TNAGG, and GC^TNAGC, respectively. The Bsu36I half-site (CC^Tn) resembles the left half-site of BbvCI (CC^Tc), and the BlpI half-site (GC^Tn) resembles the right half-site of BbvCI (GC^Tg). These similarities suggested that all three enzymes might be evolutionarily related, and if this were the case their catalytic site residues were expected to reside within regions common to all of them.

Figure 3:
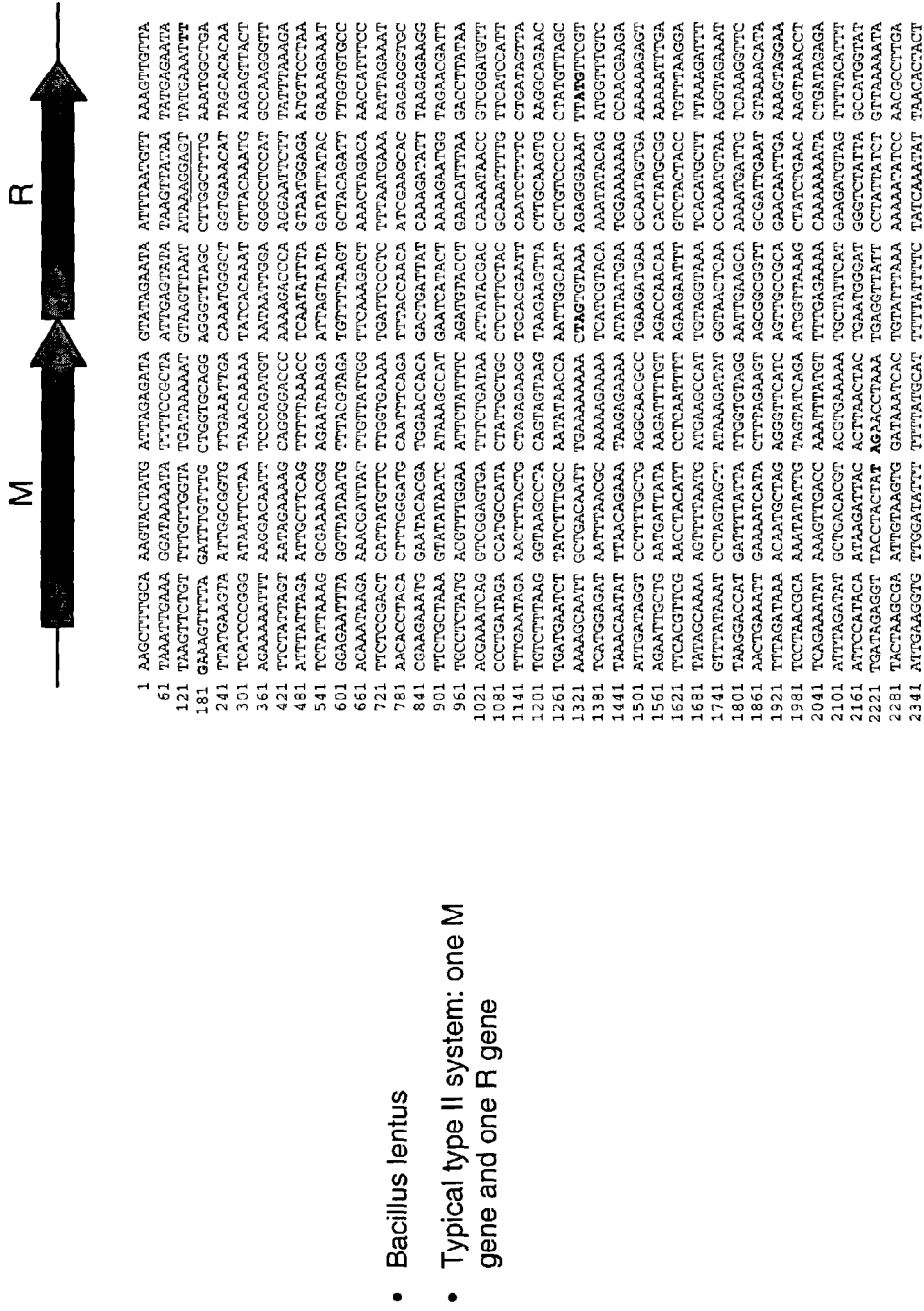
FIG. 3. Nucleotide sequence of the BlpI restriction and modification genes (SEQ ID NO:6).

Bacillus lentus (NEB #819) DNA was purified in the manner described for B. brevis (see section 1.2.2, above), and digested to completion with HindIII. The HindIII-digested DNA was ligated at 17° C. overnight into a HindIII-cleaved, CIP-treated, pUC19 plasmid vector derivative into which a single BlpI site had been introduced beforehand in the manner described for BbvCI (see section 1.2.1, above). The ligated DNA was used to transform competent E. coli ER2426 cells, and the transformed cells were propagated in culture in the presence of ampicillin. Plasmid DNA was prepared from the culture and digested at 37° C. for 2 hr with BlpI (NEB Product # R0585, New England Biolabs, Inc., Beverly, Mass.) in NEBuffer 4, and then dephosphorylated at 37° C. for 1 hr with calf intestinal phosphatase (NEB Product # M0290, New England Biolabs, Inc., Beverly, Mass.). The DNA was transformed back into competent ER2426 cells, and plasmid DNA was isolated from individual transformants and checked for resistance to digestion by BlpI. One resistant plasmid, isolate #20, expressed BlpI endonuclease activity and contained a single 3.6-kb HindIII-fragment insert. This fragment was sequenced and found to contain the complete BlpI endonuclease gene and the complete BlpI methyltransferase gene. The nucleotide sequence of the BlpI genes is shown in FIG. 3, and the predicted amino acid sequences of the proteins, in FIG. 4.

Figure 5:
FIG. 5. Nucleotide sequence of the Bsu36I restriction and modification genes (SEQ ID NO:9).

Bacillus subtilis 36 (NEB #440) DNA was purified in the manner described for B. brevis, and digested partially with HindIII. The HindIII-digested DNA was ligated at 17° C. overnight into a HindIII-cleaved, CIP-treated, pUC19 plasmid vector derivative into which two Bsu36I sites had been introduced beforehand in the manner described for BbvCI. The ligated DNA was used to transform competent E. coli ER2683 cells, and the transformed cells were propagated in culture in the presence of ampicillin. Plasmid DNA was prepared from the culture and digested at 37° C. overnight with Bsu36I (NEB Product # R0524, New England Biolabs, Inc., Beverly, Mass.) in NEBuffer 3 (100 mM NaCl, 50 mM Tris-HCl, pH 7.9, 10 mM magnesium chloride, 1 mM dithiothreitol) supplemented with 100 microgram/ml BSA. The digested DNA was treated with exonucleases III (NEB Product # M0206, New England Biolabs, Inc., Beverly, Mass.) at 37° C. for 30 min, and then it was transformed back into competent ER2683 cells. Plasmid DNA was isolated from individual transformants and checked for resistance to digestion by Bsu36I. One resistant plasmid, isolate #15, expressed Bsu36I endonuclease activity, and contained 3 HindIII-fragments totaling 4.6 kb. These fragments were sequenced and one, also 3.6-kb in length, was found to contain the complete Bsu36I endonuclease gene and the complete Bsu36I methyltransferase gene. The nucleotide sequence of the Bsu36I genes is shown in FIG. 5, and the predicted amino acid sequences of the proteins, in FIG. 6.

1.3.2 Multiple sequence alignment: The amino acid sequences of the BbvCI endonuclease subunits were aligned with those of BlpI, Bsu36I and a third related Type II endonuclease sequenced earlier, DdeI (Sznyter et al., Nucleic Acids Res. 15: 8249–8266 (1987)). Initial alignment was performed using the GCG programs 'Gap', and then 'Pretty'. Final alignment was performed by eye (FIG. 7). Several blocks of sequence conservation were revealed by the alignment. The fourth block contained the tri-peptide sequence EXK (X=C or V). This motif commonly forms part of the catalytic site of restriction endonucleases, and it was judged likely to form part of the catalytic sites in the BbvCI subunits, too.

1.4 Mutagenesis of the BbvCI Catalytic Sites 1.4.1 Mutagenic PCR primers: The nucleotide sequences of the sections of the BbvCI genes coding for the putative catalytic site EXK residues was consulted. Based on these sequences, the following four 5'-phosphorylated PCR oligonucleotide primers were synthesized.

```
R₁'mutagenic' (NEB #249-180)
5'-pTTATTAGTTTAGCCGTCGCATGTgaggtcaag (SEQ ID NO:71)
ACAAATATCGATAAAAACAAACTTAATGGGTTAGAC
-3'

R₁ reverse (NEB #249-181)
5'-pCTCTATGACTCTCACTTGCAATTTTAACGTCT (SEQ ID NO:72)
ACC-3'

R₂'mutagenic' (NEB #249-174)
5'-pTGGTTCCTGCTGTAGCGATTgagtgcaagCGG (SEQ ID NO:73)
TACCTTGAACGAAACATGCTAGATGAATGTGCTGG-
3'

R₂ reverse (NEB #249-175)
5'-pCAATGTTGGTTGTTTCTCCTTCCCCGCCATGT (SEQ ID NO:74)
CC-3'
```

The two mutagenic, forward, primers overlapped the codons for the putative catalytic site residues, and matched the sense-strand of the BbvCI R genes. The two non-mutagenic, reverse, primers matched the anti-sense strand immediately preceding the mutagenic primers. The 5'-ends of the forward and reverse primer pairs butted up flush with one another, one priming in one direction, the other priming in the opposite direction.

In the reverse primers, the bases were homogeneous at each position. In the mutagenic primers, the bases at the ends were homogeneous, but the middle 9 bases comprising the 3 codons of the putative catalytic site EVK and ECK (shown in lowercase, above) were heterogeneous. The first and second positions in these three codons were mixtures of all four bases, 80% being the wild-type base shown in lower case, and the remaining 20% being an equal mix of the other three bases. The third position in these codons was a mixture of only two bases, G and C, 80% being the wild-type base, and 20% being the other base. The 80:20 ratio was chosen to generate mutants approximately 40% of which would incorporate one amino acid change, 40% would incorporate two changes, and 10% would incorporate three. The following binomial equation describes approximately how the likelihood, P, of r mutations occurring within N codons varies with the proportion, p, of mutagenic bases in the mixtures:

$$P(r)=(N!/(N-r)!r!) \times ((1-p)^3)^{N-r} \times (1-(1-p)^3)^r$$

1.4.2 PCR mutagenesis: Two sets of PCR reactions were prepared, one to mutagenize each subunit. Each reaction was set up as follows:

| | |
|---|---|
| 10X ThermoPol Buffer: | 150 microL |
| 20X mutagenic primer: | 75 microL |
| 20X reverse primer: | 75 microL |
| 25X stock dNTP mix: | 100 microL |
| 400 ng template DNA: | 2 microL |
| MQ water: | 1058 microL |
| (Vent ® DNA polymerase: | 20 microL) |
| (Deep Vent ® DNA polymerase: | 20 microL) |

Notes: 10× ThermoPol buffer is: 200 mM Tris-HCl, pH 8.8, 100 mM KCl, 100 mM ammonium sulfate, 20 mM magnesium sulfate, 1% Triton X-100.

20× primer is 6 micromolar.

25× stock dNTP mix is 5 mM each of dATP, dCTP, dGTP, and dTTP.

Template DNA was purified plasmid pUC19(bbvCI R1,R2) at 200 microgram/ml.

The reactions were prepared on ice. The two DNA polymerases were added last, and immediately after wards the reactions were dispensed 100 microL at a time into 15 microtubes pre-warmed to 95° C. The reactions were cycled as follows: 95° C., 45 sec (denature); 4° C., 1 min (anneal); 72° C., 4 min (polymerize)×30 cycles. 72° C., 8 min (completion); 40° C. (hold).

1.4.3 Mutant isolation: The two sets of PCR reactions were separately pooled and electrophoresed in 1% agarose gels. The prominent band corresponding to the full-length PCR product from each reaction was sliced from the gel and the fragment was recovered, phenol-chloroform extracted, precipitated, and resuspended in MQ water to a concentration of approximately 100 microgram/ml. The purified fragments were separately self-ligated as follows:

| | |
|---|---|
| PCR fragment @ 100 microgram/ml: | 20 microL |
| 10X ligation buffer: | 6 microL |
| MQ water: | 32 microL |
| conc. T4 DNA ligase (2G u/ml) | 2 microL |

The ligations proceeded at room temperature for 3.5 hr., and then they were terminated by the addition of chloroform. An aliquot of each was analyzed by agarose gel electrophoresis and ligation was found to be extensive in both reactions. 1 microL aliquots of the ligations were used to transform competent *E. coli* ER2502. The transformations were plated onto LB+Ampicillin plates and incubated overnight at 37° C. 60 colonies from each set were inoculated into 10 ml L-Broth plus Ampicillin and grown overnight. 1.5 ml of each culture was used for plasmid minipreparation, and 1.7 ml was used to prepare extracts for enzyme assay.

1.4.4 Sequence analysis of the mutants: Four oligonucleotide primers were synthesized to sequence in both directions across the mutated regions in the two BbvCI subunit genes:

```
R₁(+) (NEB #249-176)
5'-GGTTAAAACCTATTTTCTCTACGAG-3'   (SEQ ID NO:75)

R₁(-) (NEB #249-177)
5'-CTTGTTTTCGAAGAACATAAATTTC-3'  (SEQ ID NO:76)

R₂(+) (NEB #249-178)
5'-ATTTAAGTCTCAGCTTTAATCCAC-3'   (SEQ ID NO:77)

R₂(-) (NEB #249-179)
5'-GAGTTCCGCTGGTGCCGAAGTATG-3'   (SEQ ID NO:78)
```

Isolates from the PCR reaction using the $R_1$ mutagenic primer were sequenced with the $R_1(+)$ and $R_1(-)$ sequencing primers. Isolates from the reaction using the $R_2$ mutagenic primer were sequenced with the $R_2(+)$ and $R_2(-)$ primers. The resulting sequences were examined to identify isolates that contained changes other than those affecting the three catalytic site amino acids. Erroneous isolates so-identified, containing mutations elsewhere, were discarded. The sequences of the remaining, genetically intact, isolates were then examined to determine the amino acids present at their catalytic sites. Representative results are shown in FIGS. 17 and 18.

1.5 Nicking Activity Assays 1.5.1 Crude extract assays: 1.7 ml of overnight cell culture of each mutant was microcentrifuged, the supernatant was discarded, and the pellet was frozen at −20° C. for up to one week. When convenient, the pellet was thawed on ice and resuspended in sonication buffer (100 mM NaCl, 20 mM Tris, pH 8.0, 1 mM EDTA, 5% glycerol) plus 10 mg/ml lysozyme. After 30 min on ice the suspension was sonicated with a micro tip for 10 sec at 60% duty using a Heat Systems-Ultrasonics Sonicator at power setting 5. After microcentrifugation to remove cell debris, 1 microL of the supernatant was incubated with 1 microgram of substrate DNA in 50 microL of NEBuffer 4 for 1 h at 37° C. The reactions were de-proteinized by the addition of 10 microL 10× stop dye containing 0.5% SDS, or 10 microL 10× stop dye followed by 5 microL phenol and 5 microL chloroform. The reactions were emulsified, microcentrifuged to clarify, and then the DNA digests were electrophoresed through 1% agarose gels for analysis.

Figure 8:
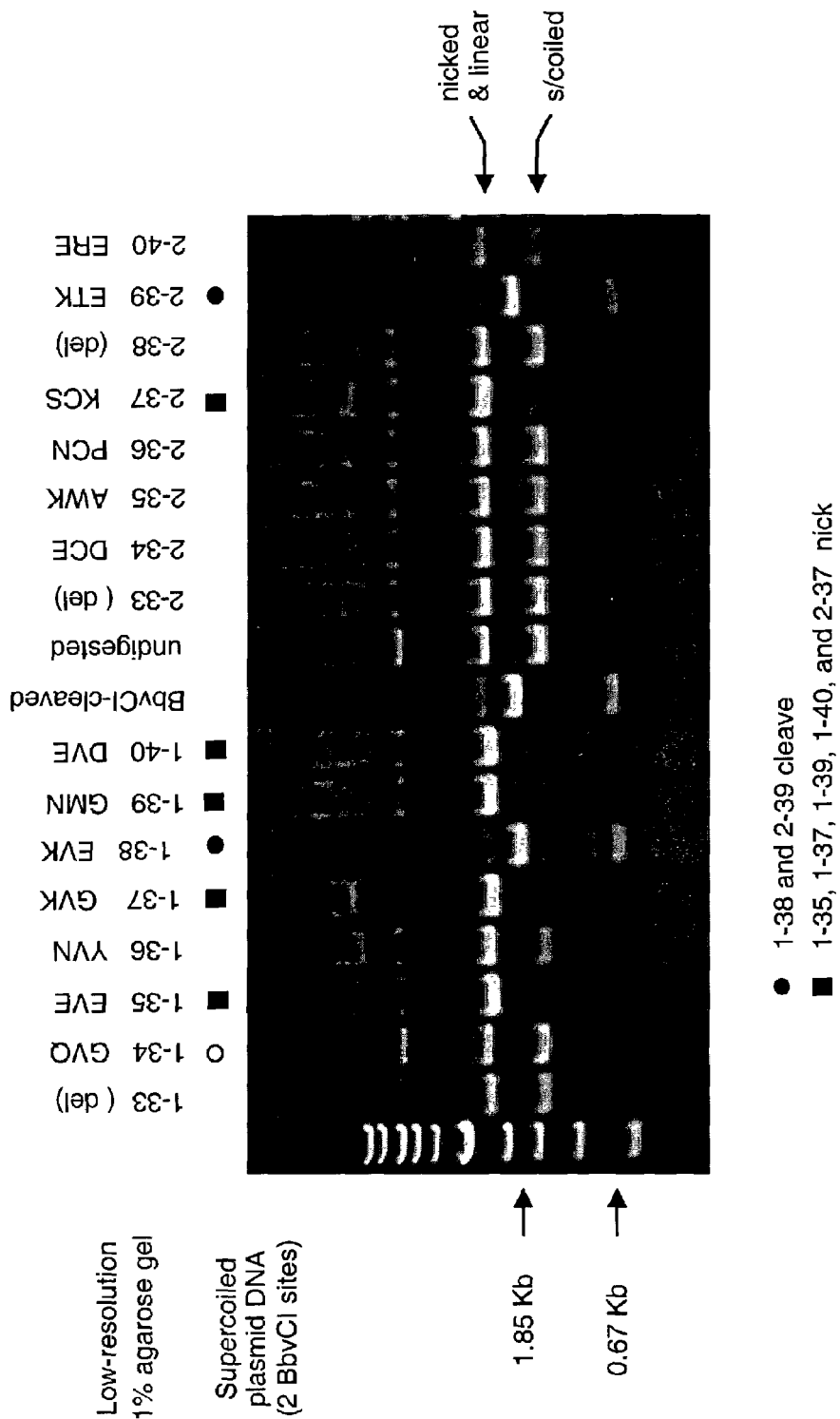
FIG. 8. Endonucleolytic activity assays of mutant enzymes. Crude extracts of the enzymes were incubated with supercoiled pUB DNA, and then electrophoresed through 1% agarose. Lane 1 (far left) contains molecular-weight markers. Lanes 2–9 contain the digestion products of enzymes 1-33 to 1-40. Control lanes 10 and 11 contain wild type R.BbvCI-digested plasmid, and undigested plasmid, respectively. Lanes 12–19 contain the digestion products of enzymes 2-33 to 2-40. Certain enzymes (e.g. 1-38, 2-39; filled black circles) cleave the plasmid. Other enzymes (e.g. 1-35, 2-37; filled black squares) nick it. And yet others (e.g. 1-36, 2-34) appear to be inactive.

Two different DNA substrates were used for characterizations: phage lambda DNA, and supercoiled pUB plasmid DNA. Lambda enabled easy assessment of DNA-cleaving activity, and pUB, easy assessment of DNA-nicking activity. Some isolates produced wild type enzymes that cleaved both DNA substrates (FIG. 8). The mutations in these did not affect the catalytic activities of the subunits. Other isolates produced inactive enzymes that neither cleaved nor nicked the DNA substrates. The mutations in these, we presume, disrupted the subunits so severely that all catalytic activity was abolished. And yet other isolates produced nicking enzymes that converted the supercoiled plasmid DNA to the open circular form, and distinctively changed the mobility of the lambda DNA, but generated no full-length linear plasmid fragments, or BbvCI-cleavage fragments. The mutations in these inactivated the catalytic sites in a localised fashion without affecting the rest of the enzyme. The latter mutants were the nicking endonucleases we sought.

1.5.2 Nicking endonuclease purification: Enzyme mutants 1-37 ($R_1E167G:R_2^+$) and 2-12 ($R_1^+:R_2E177G$) were selected as being representative of nicking mutants with inactive catalytic sites in the $R_1$ subunit, and the $R_2$ subunit, respectively. These endonucleases were purified to homogeneity. 100 liter cell cultures were grown to saturation at 37° C. in L-Broth (10 gm/L Tryptone, 5 gm/L yeast extract, 0.17 M NaCl, 5.6 mM dextrose, 5 mM $MgCl_2$), harvested by centrifugation, and stored frozen at −70° C. 100 gm cell paste was thawed at room temperature and resuspended in 350 ml of column buffer (20 mM Tris-HCl, pH 8.0, 6 mM Beta-mercaptoethanol, 0.25 mM EDTA, 5% glycerol) containing 100 mM NaCl. 500 mg of lysozyme was added, and the suspension was stirred for 30 min at 4° C. The suspension was sonicated for 2×4' intervals using a Branson Sonifier at 70% duty, and a power setting of 8. The sonicated suspension were centrifuged in 2×250 ml bottles at 13,000 rpm for 30 min in a JA-14 (Beckman) rotor. The supernatant was decanted and recentrifuged twice more, until no cell debris remained.

The cleared supernatant was loaded at 4 ml/min onto 100 ml of Heparin Hyper-D resin (BioSepra, Inc.) in a XK26 (Pharmacia) FPLC column. The column was washed with 2 column vol of column buffer containing 100 mM NaCl, and then eluted with column buffer containing an increasing NaCl gradient. 5 ml fractions were collected and selected fractions were assayed for enzyme activity in the following manner. 2 microL of each fraction was diluted in 100 microL of NEBuffer 4, and 2 microL of the dilution was added to 25 microL of NEBuffer 4 containing 0.5 microgram of supercoiled pUB DNA or phage lambda DNA. The reactions were incubated at 37° C. for 2 min, stopped and de-proteinized by the addition of 5 microL of 10× stop dye containing 0.5% SDS, and then electrophoresed on an 0.8% agarose gel and visualized. Peak activity eluted from the Heparin column around 0.5 M NaCl.

Active fractions were pooled to a volume of approximately 100 ml and dialyzed overnight against column buffer containing 50 mM NaCl. The precipitate that formed was removed by centrifugation without loss of enzyme activity. The clarified dialyzate was passed through 24 ml of Source 15S resin (Pharmacia) in a HR16/10 FPLC column. The column was washed with 2 column vols. of column buffer containing 50 mM NaCl. Enzyme activity remained in the flow-through which was brought up to 0.15 M NaCl and passed through 8 ml of Source 15Q resin (Pharmacia) in a HR10/10 FPLC column. The column was washed with 1 column vol of column buffer containing 150 mM NaCl, and enzyme activity again remained in the flow-through. The flow through was loaded directly onto 60 ml of Heparin Hyper-D resin in a XK26 column once more, and eluted with increasing [NaCl] gradient in column buffer. Active fractions peaked at 0.5 M NaCl and were pooled, dialyzed into storage buffer (50 mM NaCl, 20 mM Tris, pH 7.4, 1 mM DTT, 0.1 mM EDTA, 50% glycerol) and stored at −20° C. for short-term storage, or −70° C. for the longer term.

Figure 9:
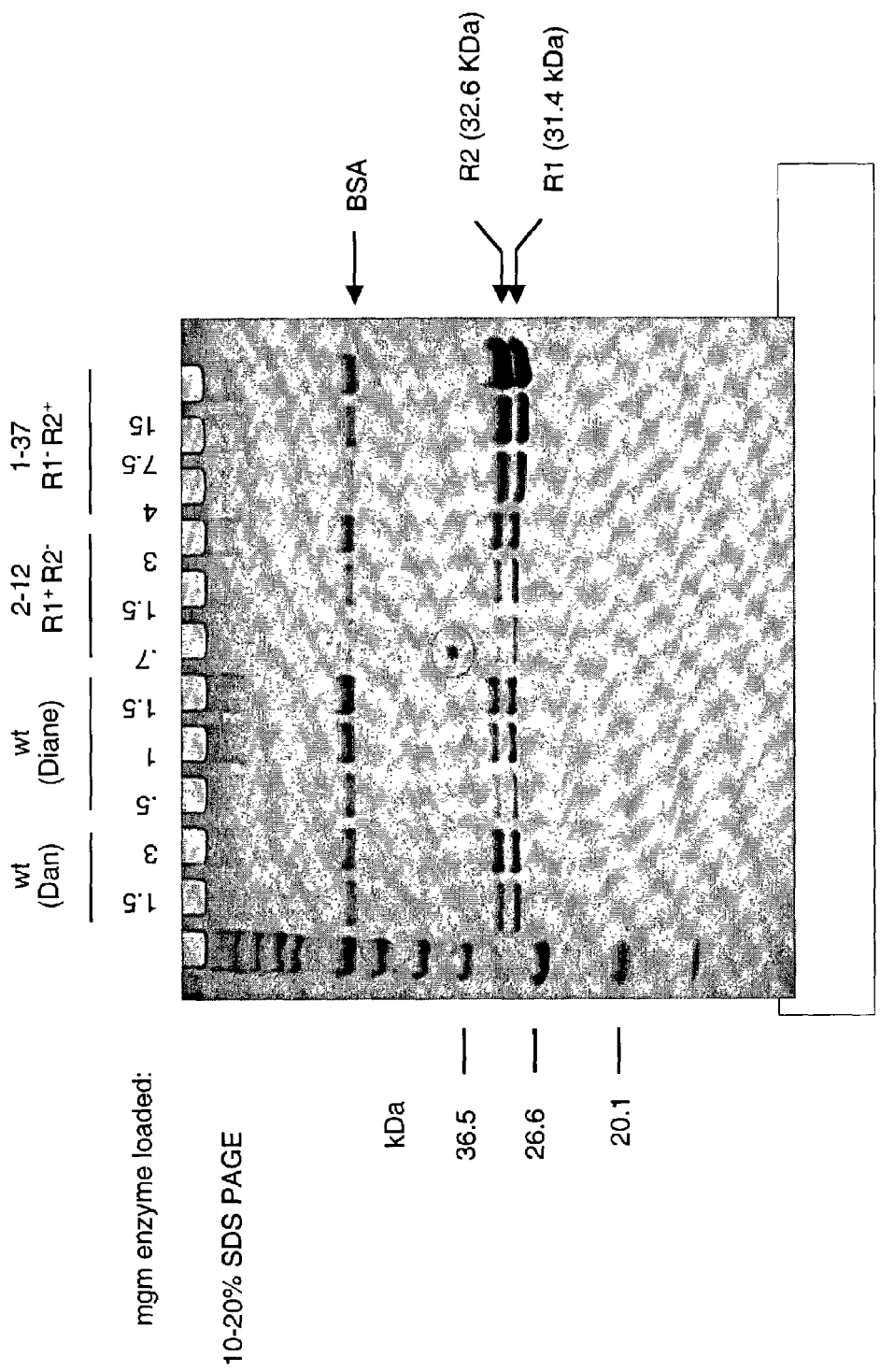
FIG. 9. SDS-PAGE analysis of purified wild type R.BbvCI restriction endonuclease (lanes 2–3: prep. 'Dan'; lanes 4–6: prep. 'Diane'), and of purified N.BbvCI nicking endonucleases 2-12 (lanes 7–9), and 1-37 (lanes 10–12). Lane 1 (far left) contains molecular weight markers. All the enzymes preps migrate as two bands of roughly equal intensity signifying that the enzymes are heterodimers with 1:1 subunit stoichiometry.

Enzymes prepared in this way had a final protein concentration of approximately 40 mg/ml. The yields and activities of these enzyme preps are shown in FIG. 16. Analyzed by SDS-PAGE, the enzymes were found to be homogeneous and to migrate as two bands of the expected sizes, and in the approximate ratio of 1:1 (FIG. 9).

Figure 10:
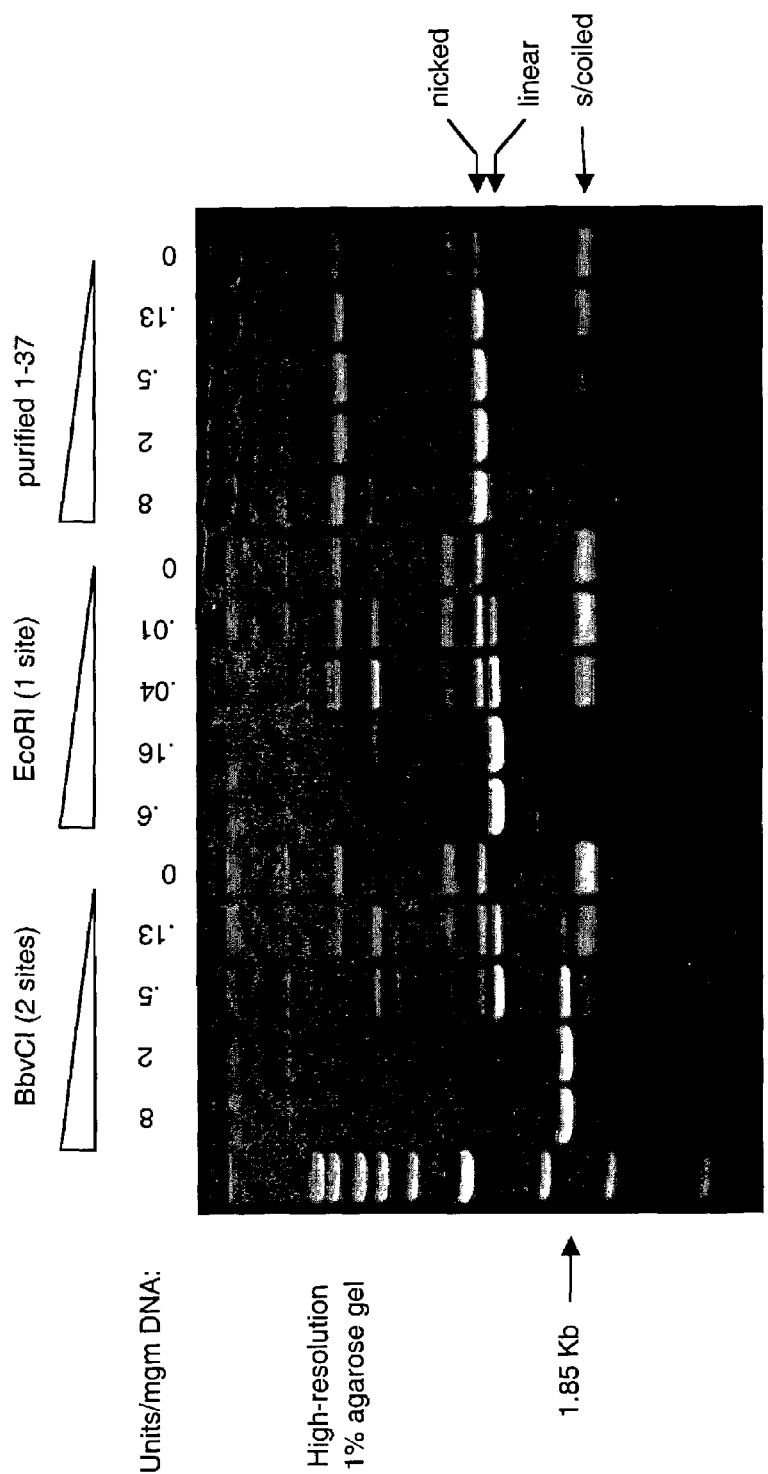
FIG. 10. High-resolution agarose gel electrophoresis of supercoiled pUB DNA titrated with varying amounts of restriction endonucleases R.BbvCI (lanes 2–6) and R.EcoRI (lanes 7–11), and nicking endonuclease N.BbvCI 1-37 (lanes 11–15). Lane 1 (far left) contains molecular weight markers. Lane 16 contains undigested pUB substrate DNA. EcoRI (1 site) cleaves pUB to produce a full-length linear fragment. R.BbvCI (2 sites) produces full-length linear fragment transiently, but this is cleaved further into two fragments. (Only the larger of these two fragments is visible; the smaller fragment migrated beyond the bottom of the gel.) N.BbvCI 1-37 nicks pUB to produce a full length open-circular product that migrates slightly slower than its linear counterpart.

1.5.3 Characterization of nicking endonuclease activity: Aliquots from the nicking enzyme preps were titrated on supercoiled pUB DNA (two BbvCI sites). Control titrations on the same DNA using EcoRI (1 site; NEB Product # R0101, New England Biolabs, Inc., Beverly, Mass.) and the wild type BbvCI cleaving enzyme were run alongside. The digests were analyzed by high-resolution agarose gel electrophoresis. The product of the nicking enzymes migrated at a slightly slower rate than the full-length linear product of the EcoRI-digestion, confirming that it was not linear. No BbvCI-fragments were produced in the nicking enzyme digests confirming that these enzymes were unable to hydrolyze both strands of the DNA (FIG. 10).

(Note: Subsequent digestions with the nicking enzyme 1-37 did on occasion produce BbvCI-cleavage fragments at a very low level. This was traced to the presence of variable amounts of manganese in the water. The altered catalytic site of 1-37 (EVK-→GVK) is inactive in the presence of magnesium but partially active in the presence of manganese. Other mutants in the $R_1$ subunit do not behave in this way, nor does the equivalent mutation in the catalytic site of the $R_2$ subunit: mutant 2-12 (ECK-→GCK) nicks DNA in the presence of either magnesium and manganese.)

The sequence-specificities of the purified 1-37 and 2-12 endonucleases were tested by incubating them with supercoiled pUC19 DNA, a plasmid containing no BbvCI sites. No nicking by either enzyme was observed. In contrast, in control digestions run alongside, the enzymes nicked pUB DNA to completion, and R.EcoRI but not R.BbvCI, digested pUC19 DNA to completion.

Figure 11:
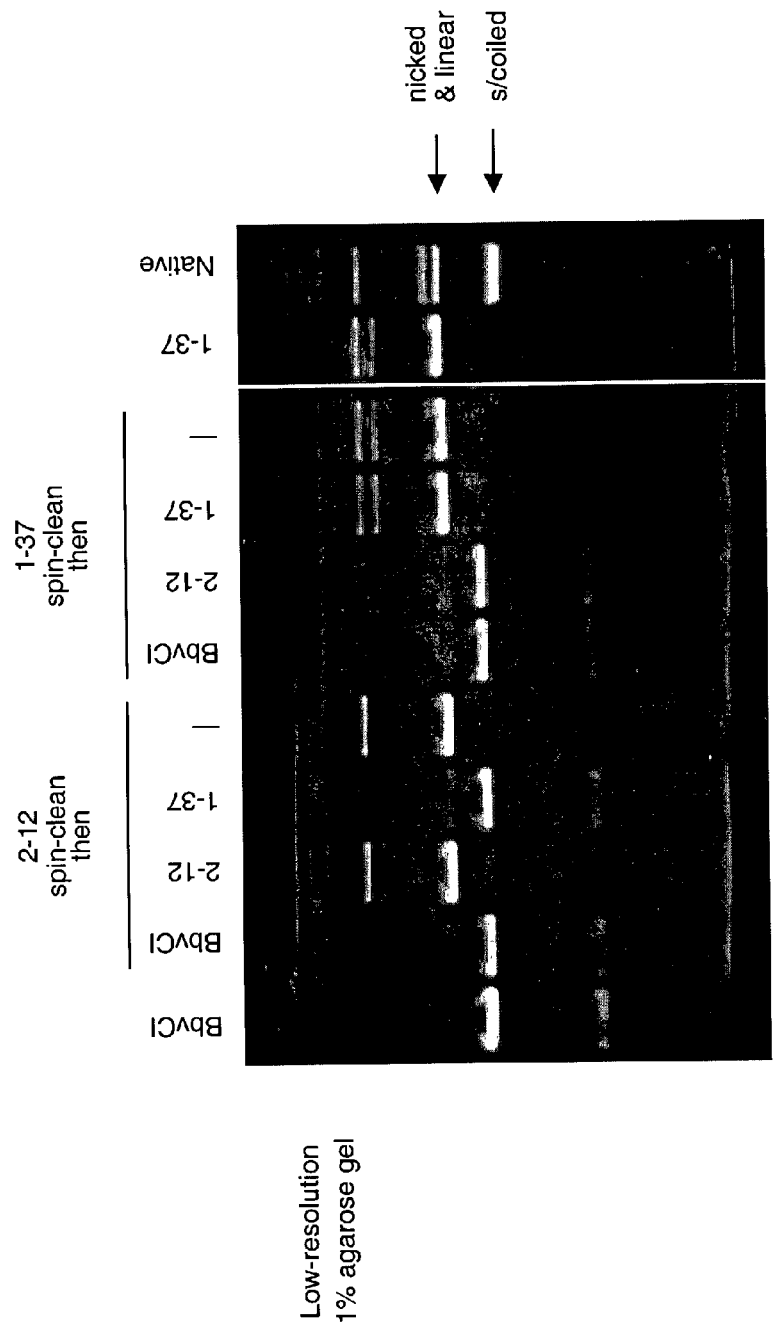
FIG. 11. Agarose gel of supercoiled pUB DNA nicked in sequence with nicking enzymes N.BbvCI 1-37 and 2-12. Lane 1 (far left; R.BbvCI-digested pUB), and lanes 10 (N.BbvCI-nicked pUB) and 11 (undigested pUB) are controls. pUB DNA was nicked first with N.BbvCI 1-37 and then purified by microfiltration (lane 9). This nicked DNA was then redigested with more N.BbvCI 1-37 (lane 8), or with N.BbvCI 2-12 (lane 7) or R.BbvCI (lane 6). Alternately, pUB DNA was first nicked with N.BbvCI 2-12 and purified (lane 5), and then redigested with N.BbvCI 1-37 (lane 4), more N.BbvCI 2-12 (lane 3), or with R.BbvCI. Digesting with either nicking enzyme alone nicks the DNA. Redigesting with the same enzyme has no further affect, but redigesting with the other enzyme results in double-strand cleavage identical to that produced by R.BbvCI.

The strand-specificities of the purified 1-37 and 2-12 endonucleases was tested by incubating supercoiled pUB DNA first with one nicking endonuclease and then with the other. The DNA was cleaned on 'Zymoclean' spin columns to remove the first enzyme prior to addition of the second. Incubating with either enzyme nicked the DNA. Incubating with the same enzyme in the second round as was used in the first had no effect, but incubating with the other enzyme resulted in complete DNA cleavage, and the production of fragments identical to those produced by R.BbvCI. This occurred regardless of the order in which the nicking enzymes were added, and it demonstrated that 1-37 and 2-12 nick DNA on opposite strands (FIG. 11).

The strand-specificities of the purified 1-37 and 2-12 endonucleases was further examined by sequencing in both directions across the nicked BbvCI sites in pUB DNA. pUB DNA was separately nicked with each enzyme. The nicked DNA samples were purified on Zymoclean spin-columns, resuspended in MQ $H_2O$, and then used as substrates for DNA sequencing reactions in both directions across the two BbvCI recognition sites using the following custom-synthesized oligonucleotide primers:

```
Fwd-1 (NEB #254-257)
5'-CACAATTCCACACAACATACGAGC-3'      (SEQ ID NO:79)

Rev-1 (NEB #254-258)
5'-TCGCCACCTCTGACTTGAGCGTCG-3'      (SEQ ID NO:80)

Fwd-2 (NEB #254-259)
5'-TTCCTTTTTCAATATTATTGAAGC-3'      (SEQ ID NO:81)

Rev-2 (NEB #254-260)
5'-CGACACCCGCCAACACCCGCTGAC-3'      (SEQ ID NO:82)
```

Figure 12:
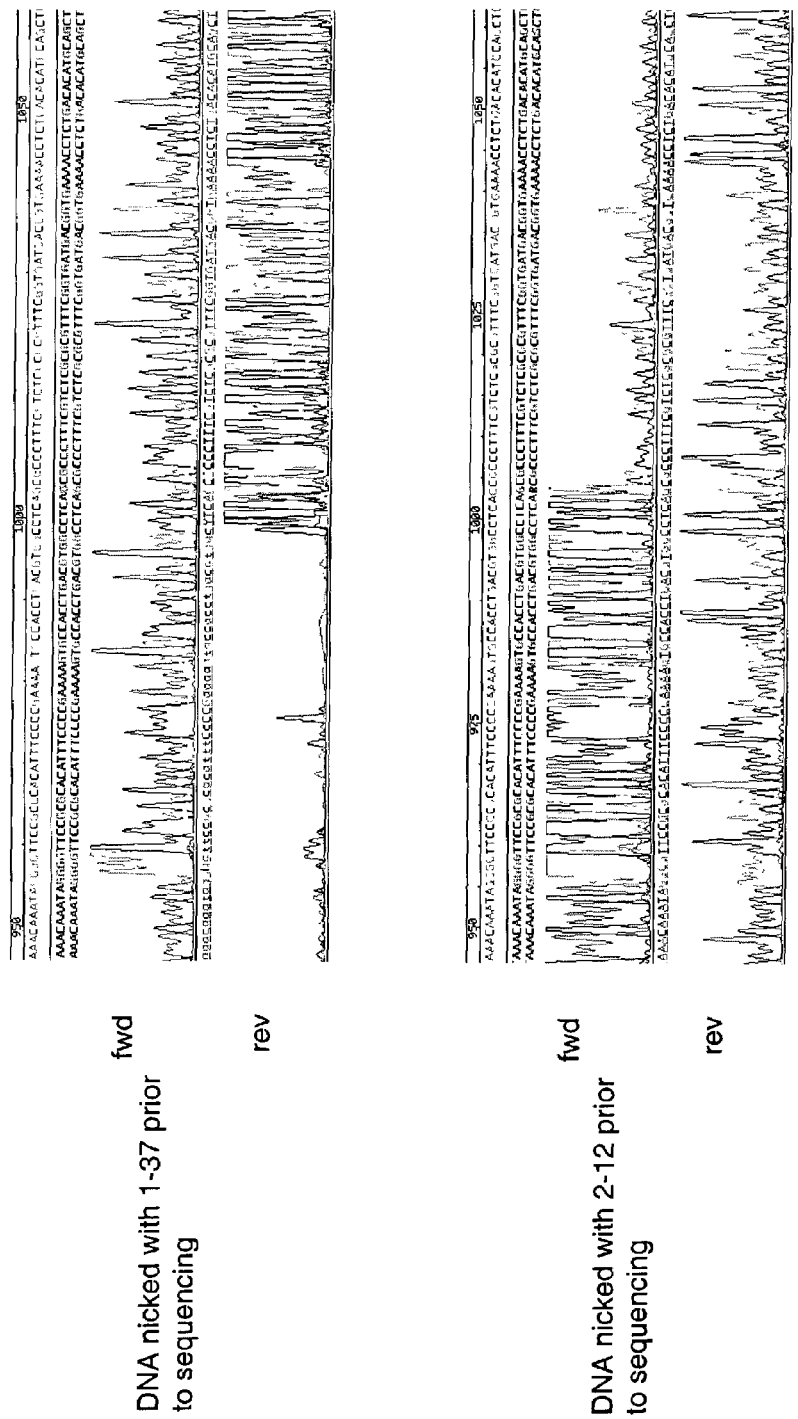
FIG. 12. Automated DNA sequencing traces in both directions through one of the BbvCI sites in pUB DNA digested with nicking enzymes N.BbvCI 1-37 or 2-12. Nicking with N.BbvCI 1-37 (top traces) does not affect the 'forward' sequencing reaction, but it causes the 'reverse' reaction to terminate at the BbvCI site. This demonstrates that enzyme 1-37 (composition: $R_1^-:R_2^+$) nicks the 'top', CCTCAGC, strand of the recognition sequence and not the 'bottom' strand. Nicking with N.BbvCI 2-12 has the opposite effect (bottom traces), demonstrating that this enzyme (composition: $R_1^+:R_2^-$) nicks the bottom, GCTCAGG, strand of the recognition sequence and not the top strand.

On DNA nicked with 1-37, the reactions with primers Fwd-1 and Fwd-2 produced continuous sequencing traces through the BbvCI sites, indicating that the 'bottom' strand in the recognition sequences—the template strand in these reactions—was intact. In contrast, the reactions using primers Rev-1 an Rev-2 produced taces that stopped abruptly at the BbvCI sites, indicating that the 'top' strand in both of the recognition sequences was nicked (FIG. 12). In these latter reactions, the traces ended with . . . GCTGAr, indicting that the template strand was nicked after the second base in the sequence . . . CC^TCAGC . . . , at the position indicated by '^'. (The weak, final mixed a and g signal, 'r', was an artifact caused by the template-independent addition of purines by the Taq DNA polymerase used for sequencing.) This is the same position at which the wild-type BbvCI endonuclease cleaves this strand.

Conversely, on DNA nicked with 2-12, the reactions with Fwd-1 and Fwd-2 primers stopped abruptly at the BbvCI sites, and the reactions using the Rev-1 an Rev-2 primers produced continuous ladders (FIG. 12). The traces in the terminated reactions ended with . . . CCTCAr, indicting that the nick on the template strand also occurred after the second base in the recognition sequence GC^TGAGG, again the same position at which wild-type R.BbvCI hydrolyzes this strand.

These results demonstrate that the $R_1$ subunit of BbvCI hydrolyzes the bottom strand of the recognition sequence, and the $R_2$ subunit hydrolyzes the top strand. The wild-type and nicking endonucleases thus have the following specificities:

```
R.BbvCI (R₁⁺:R₂⁺)                    C C^T C A G C
Wt heterodimer                       G G A G T^C G Nt.BbvCI (e.g. 1-37: R₁⁻:R₂⁺)        C C^T C A G C
Top-strand nicking enzyme            G G A G T C G Nb.BbvCI (e.g. 2-12: R₁⁺:R₂⁻)        C C T C A G C
Bottom-strand nicking enzyme         G G A G T^C G
```

1.5.4 Cation-dependent enzyme activity: The endonucleolytic activities of crude extracts of the nicking mutants were tested in digestion buffer containing (a) only magnesium as the divalent cation; (b) only manganese as the divalent cation; or (c) a mixture of both magnesium and manganese. Most of the mutant enzymes that nicked when only magnesium was present continued to nick, but to lesser extent, when only manganese was present or when both cations were present. However, three enzymes that nicked when only magnesium was present, 1-29 ($R_1E167D:R_2^+$), 1-37 ($R_1E167G:R_2^+$), and 2-56 ($R_1^+:R_2E177D$), displayed substantial cleavage activity in the presence of only manganese, or in the presence of both magnesium and manganese. Evidently, the mutated catalytic sites in these three enzymes are inactive when the cation is magnesium, but partially active when the cation is manganese. The addition of manganese to these three enzymes, then, converts them from DNA-nicking enzymes to DNA-cleaving enzymes.

The endonucleolytic activities of crude extracts of the nicking mutants were further tested in digestion buffer containing both magnesium and calcium. The presence of calcium at a level as low as 4 mM completely inhibited nicking activity in all of the mutants except 2-56. Mutant 2-56 ($R_1^+:R_2E177D$) was fully active in 4 mM calcium, but was completely inhibited by 8–10 mM calcium.

EXAMPLE 2

Potential Nicking Derivatives of BstNBI and BbvI

Type IIs and IIf restriction endonucleases are thought to catalyze DNA cleavage, in general, by transient homodimerization. Just as the occasional Type II endonuclease acts as a heterodimer, however, so too might the occasional Type IIs or IIf endonuclease. This Example is based on just such a prospect. It refers particularly to BbvI and BstNBI, Type IIs endonucleases for which circumstantial evidence of a possible heterodimeric nature exists. If either enzyme indeed acts as a heterodimer, then it is a candidate for conversion to a nicking endonuclease by the present invention. Of the few Type IIf endonucleases discovered to date, none appears likely to be heterodimeric. Such enzymes probably do exist in nature, however, and when they are discovered they will be candidates for conversion to nicking endonucleases by the present invention.

Heterodimeric Type IIs restriction endonucleases are expected to comprise one large subunit and one small subunit. The large subunit, like a normal Type IIs endonuclease, will comprise two domains, one for sequence-specific DNA-binding, the other for catalysis and dimerization. The small subunit will comprise the second catalytic site and dimerization surface. Dimerization will take place, not between two molecules of the large subunit as occurs in enzymes that homodimerize, but between one molecule of the large subunit and one of the small subunit. The dimerization surfaces on the subunits of the heterodimer will be such that each subunit can associate with the other, but not with itself.

If we denote sequence-specific DNA-binding as 'B', DNA-cleavage as 'C', and dimerization as 'D', then the normal Type IIs monomer can be described as $B^+C^+D^+$, and the catalytically active, transient homodimer as $B^+C^+D^+:B^+C^+D^+$, where '+' signifies wild-type functionality, and '−' (see later) signifies non-functionality. Using the same notation for heterodimeric Type IIs endonucleases, the large subunit can be described as $B^+C_1^+D_1^+$, the small subunit as $C_2^+D_2^+$, and the catalytically active heterodimer as $B^+C_1^+D_1^+:C_2^+D_2^+$. The distinction between the homodimeric enzyme and the heterodimeric enzyme is that in the former, the catalytic sites, C, are identical; the dimerization surfaces, D, are identical and self-compatible; and sequence-specific binding by only one of the two DNA-binding domains, B, is sufficient for strand-hydrolysis to proceed. In contrast, in the heterodimer the catalytic sites, $C_1$ and $C_2$, are different; the dimerization surfaces, $D_1$ and $D_2$, are different and are compatible, but not self-compatible; and there exists only one binding domain by which sequence-specific DNA-binding can occur.

Predictable differences distinguish heterodimeric Type IIs endonucleases from their homodimeric counterparts. Whereas homodimeric endonucleases are encoded by single genes, heterodimeric endonucleases will be encoded by two genes, one for each subunit. The two genes are likely to lie side-by-side in the genome, in the same orientation. Amino acid sequence analysis of the subunits might reveal the presence of putative catalytic site residues in each. The two subunits might share amino acid sequence homology with each other, and with other restriction endonucleases, particularly in the catalytic site regions. In vivo, the gene for neither subunit alone would manifest DNA-cleavage activity, but together they would. The gene for the large subunit on its own might manifest DNA-nicking activity, or it might be inactive. The gene for the small subunit on its own might manifest non-specific endonuclease activity, or more likely it would be inactive. Mixing the two subunits together in vitro should produce DNA-cleavage activity. If the large subunit alone displayed DNA-nicking activity in vitro, adding the small subunit should convert this nicking activity to DNA-cleaving activity.

The activity of homodimerizing Type IIs endonucleases is higher on DNA substrates that contain several recognition sites than it is on DNA substrates that contain only one. This should not be true for heterodimeric Type IIs endonucleases;

they should display the same activity regardless of the number of recognition sites in the DNA. The same should apply to 'functionally heterodimeric' endonucleases whose two ancestral subunits have fused to form a single, monomeric, protein. This 'cis-stimulation' effect could be a useful experimental test to rapidly distinguish between homodimeric and heterodimeric/monomeric endonucleases.

Because the subunits of heterodimers will associate and dissociate at some rate, they are liable to become separated during protein purification. A heterodimeric Type IIs endonuclease would begin with a 1:1 subunit stoichiometry, but during purification one subunit—probably the smallest—could gradually be lost, and the other subunit could come to predominate in the active fractions. The DNA-cleavage activity of such fractions would depend upon how much of the minor subunit remained, and so the overall amount of enzyme activity would decline during purification, giving the enzyme the appearance of being unstable. If the large subunit on its own displayed nicking activity, and the small subunit were lost during purification, active fractions of the enzyme would exhibit an increasing specific activity for nicking as opposed to cleaving, and ultimately the enzyme might appear to be natural nicking endonuclease, and not a cleaving endonucleases at all.

A small unidentified open reading frame lies next to the 'endonuclease' genes in the BbvI and the BstNBI restriction-modification systems (Higgins, et al., *Nucleic Acids Res.* 29:2492–2501 (2001)). The BbvI ORF potentially encodes a protein of around 150 aa that displays homology to the C-terminal halves of two Type II endonucleases, gb:U13922, and gb:U43736. The BstNBI ORF potentially encodes a protein of approximately 180 amino acids that displays homology to the C-terminal catalytic domains of several Type IIs endonucleases, including that of the N.BstNBI nicking endonuclease encoded by the adjacent gene. The acidic catalytic site residues present in the nicking endonuclease are also present in the ORF. Both the BbvI and the BstNBI ORFs are preceded by substantial ribosome-binding sites, and both are followed by substantial stem-loop transcription terminators that likely isolate them from the adjacent, opposed, methyltransferase genes. Taken together, these features suggest that the ORFs are expressed, and that their products are important components in the proper biological functioning of the BbvI and BstNBI restriction-modification systems. Plausibly, the ORFs could be the genes for the small catalytic subunits of hitherto unrecognized heterodimeric endonucleases, the large subunits of which are encoded by the adjacent 'endonuclease' genes. Additional, perhaps similar, systems can be found in GenBank, for example genes BH4001-BH4004 of AP001520 from the *Bacillus halodurans* genome (Takami, H., et al. *Nucleic Acids Res.* 28:4317–4331 (2000)). If these endonucleases are indeed heterodimeric, then their two catalytic sites can be independently altered in the ways described in Example 1.

Although natural R.BstNBI has not yet been discovered, we speculate that co-expressing the bstNBIN gene and the adjacent ORF might produce this enzyme in vivo, and that mixing N.BstNBI with the purified product of the BstNBI ORF might produce it in vitro, too. N.BstNBI nicks the top strand of DNA four bases outside the recognition sequence (Higgins, et al. *Nucleic Acids Res.* 29:2492–2501 (2001)). If N.BstNBI is the large subunit of a heterodimer, it should be possible to convert the heterodimer into a nicking enzyme of the opposite strand-specificity by inactivating the catalytic site in just the large subunit. The following enzyme activities is thus predicted as follows:

| | |
|---|---|
| N.BstNBI ($B^+C_1^+D_1^+$): natural monomer | GAGTCNNNN^N . . . CTCAGNNNNNN . . . |
| R.BstNBI ($B^+C_1^+D_1^+:C_2^+D_2^+$) hypothetical heterodimer | GAGTCNNNN^N . . . CTCAGNNNN^N . . . |
| $N_t$.BstNBI ($B^+C_1^+D_1^+:C_2^-D_2^+$) top-strand nicker | GAGTCNNNN^N . . . CTCAGNNNNNN . . . |
| $N_b$.BstNBI ($B^+C_1^-D_1^+:C_2^+D_2^+$) bottom-strand nicker | GAGTCNNNNNN . . . CTCAGNNNN^N . . . |

(In the above sequences the location of the nick on the bottom stand is four bases beyond the recognition sequence.)

We hypothesize that R.BbvI might also be naturally heterodimeric, but that the isolated large subunit of this enzyme, unlike that of BstNBI, does not display nicking activity. Consequently, R.BbvCI may be convertible into a nicking endonuclease of either strand specificity to create the following:

| | |
|---|---|
| R.BbvI ($B^+C_1^+D_1^+:C_2^+D^+$) hypothetical heterodimer | GCAGCNNNNNNNN^NNNNN . . . CGTCGNNNNNNNNNNNN^N . . . |
| $N_t$.BbvI ($B^+C_1^+D_1^+:C_2^-D_2^+$) top-strand nicker | GCAGCNNNNNNNN^NNNNN . . . CGTCGNNNNNNNNNNNNN . . . |
| $N_b$.BbvI ($B^+C_1^-D_1^+:C_2^+D_2^+$) bottom-strand nicker | GCAGCNNNNNNNNNNNNN . . . CGTCGNNNNNNNNNNNN^N . . . |

(In the above sequences, the large subunit is shown to hydrolyze the top strand, and the small subunit, the bottom strand.)

EXAMPLE 3

Potential Nicking Derivatives of FokI

Dimerization of Type IIs and Type IIf restriction endonucleases is thought to occur, in general, between the catalytic domains of identical enzyme molecules, one bound specifically to the recognition site in DNA, the other perhaps free in solution, or bound to DNA non-specifically (Wah et al., *Nature.* 388:97–100 (1997); Wah et al., *Proc. Natl. Acad. Sci. USA* 95:10564–10569 (1998)). Since the catalytic sites in these enzymes are identical, they are unsuitable for conversion to nicking endonucleases by the present invention. However, experiments with the prototypical Type IIs endonuclease, FokI, indicate that under certain circumstances these homodimerizing enzymes can be coaxed into acting as 'combinational' heterodimers (Bitinaite et al., *Proc. Natl. Acad. Sci. USA* 95:10570–10575 (1998)). As the subunits of such heterodimers differ, they are in this form suitable for conversion to nicking enzymes. Compensating deficiencies may be introduced into a Type IIs and IIf endonucleases that would render the enzymes catalytically inactive, individually as homodimers, but catalytically active, in combination, as heterodimers. Such heterodimers would catalyze DNA-nicking rather than DNA-cleavage.

Bitinaite et. al. (*Proc. Natl. Acad. Sci. USA* 95:10570–10575 (1998)) corrupted the dimerization surface of the catalytic domain of R.FokI to prevent homodimer formation, and found that the resulting enzyme, FokI (D483A, R487A), displayed DNA-nicking activity and much reduced DNA-cleaving activity. We can depict such dimerization-defective 'hemidimers' as $B^+C^+D^-$. Kong et al. (U.S. Pat. No. 6,395,523) extended this line of experimentation to other Type IIs endonucleases, and in so-doing created highly active, hemidimeric DNA-nicking enzymes, N.MlyI and N.AlwI that also display much reduced DNA-cleaving activity. When diluted, R.FokI exhibits disproportionately low DNA-cleaving activity due to infrequent homodimer formation. Bitinaite et al. (1998) showed that enzyme activity in these circumstances could be elevated not only by adding more wild-type protein ($B^+C^+D^+$), but also by adding the separated FokI catalytic domain ($C^+D^+$), or a second mutated enzyme, N13Y, that no longer specifically bound to the FokI recognition sequence ($B^-C^+D^+$). Elevated activity in the former instance derived from wild-type FokI homodimers of composition $B^+C^+D^+:B^+C^+D^+$, and in the latter instances from combination heterodimers of composition $B^+C^+D^+:C^+D^+$, and $B^+C^+D^+:B^-C^+D^+$, respectively.

Waugh and Sauer demonstrated that the catalytic site mutants, FokI(D450A), and FokI(D467A), continued to bind to the FokI recognition sequence, but no longer catalyzed DNA strand-hydrolysis (Waugh and Sauer, *Proc. Natl. Acad. Sci. USA* 90:9596–9600 (1993)). Assuming that these catalysis-deficient enzymes dimerize properly, they can be depicted as $B^+C^-D^+$. In a 1:1 mixture of a Waugh-type, catalysis-deficient enzyme (e.g. D450A) and a Bitinaite-type binding-deficient enzyme (e.g. N13Y, or the separated catalytic domain), approximately one-half of the dimers that form will be hybrids between the two proteins. In principle, these combinational heterodimers, of composition $B^+C^-D^+$: $B^-C^+D^+$, or $B^+C^-D^+:C^+D^+$, should bind to DNA through the functional DNA binding-domain of one subunit and catalyze strand-hydrolysis through the functional catalytic domain of the other subunit, under circumstances where neither homodimeric enzyme could. Since the heterodimer in these cases would possess only one catalytic site, it would specifically nick DNA rather than cleave it.

This approach to creating a nicking endonuclease by combinational heterodimerization has considerable generality. It is by no means certain that best combination of mutations, even in the case of FokI, would be those equivalent to D450A, D467A, N13Y, or the separated catalytic domain, however, and so experimentation with various combinations on a case-by-case basis is to be expected in practice. For FokI, and for other Type IIs endonucleases like it, the following enzymatic scenario can be envisaged:

| | |
|---|---|
| R.FokI ($B^+C^+D^+:B^+C^+D^+$) active homodimer | GGATGNNNNNNNNN^NNNNN . . . CCTACNNNNNNNNNNNN^N . . . |
| Mutant 1 ($B^+C^-D^+:B^+C^-D^+$) | Inactive |
| Mutant 2 ($B^-C^+D^+:B^-C^+D^+$ or $C^+D^+:C^+D^+$) | Inactive |
| N.FokI ($B^+C^-D^+:B^-C^+D^+$ or $B^+C^-D^+:C^+D^+$) nicking 'heterodimer' | GGATGNNNNNNNNN^NNNNN . . . CCTACNNNNNNNNNNNN . . . |

(In the above, enzymes of one strand-specificity may be generated.)

Type IIf restriction endonucleases (also referred to as 'Type IV' endonucleases; (Janulaitis et al., *Nucl. Acids Res.* 20:6043–6049 (1992)) are organized somewhat differently to Type IIs enzymes, but they too should be amenable to the kinds of manipulations described in this Example for FokI, and appropriate combinations of defective Type IIf enzymes should also manifest sequence-specific, strand-specific, DNA-nicking activities. Experimental investigation of Type IIf enzymes, and comparative analysis of their amino acid sequences, shows them to be combination endonuclease-methyltransferases of some complexity (Janulaitis et al., *Nucl. Acids Res.* 20:6051–6056 (1992); Kong et al., *J. Biol. Chem.* 269:683–690 (1994); Sears et al., *Nucleic Acids Res.* 24:3590–3592 (1996); Piekarowicz et al., *J. Mol. Biol.* 293:1055–1065 (1999)). The N-terminal 200–250 aa of the proteins comprises a catalytic domain for DNA strand hydrolysis (Rimseliene and Timinskas, *Biologija.* 1:31–33 (1997); Kong, *J. Mol. Biol.* 279:823–832 (1998)). The central 350–400 aa comprises a catalytic domain for DNA methylation, and usually resembles the gamma-variety of N6-adenine methyltransferases (Wilson, *Methods Enzymol.* 216:259–279 (1992)). And the C-terminal 250 aa comprises a sequence-specific DNA-binding domain, and often resembles a single recognition-domain of a Type I endonuclease-methyltransferase specificity-subunit. The complexity of these proteins stems from their combined enzymatic activities; their structural variability (in some enzymes the DNA-binding domain is an integral part of the enzyme, and in others it is separate subunit); and from their organizational variability (some enzymes bind to DNA as monomers, and others bind as dimers or trimers and then form higher-order homodimers between these assemblages in order to catalyze DNA cleavage).

The simplest Type IIf enzyme, such as Eco57I, can be described as $C^+D^+M^+B^+$ in the monomeric, DNA-bound form, and $C^+D^+M^+B^+:C^+D^+M^+B^+$ in the active, dimerized form. Since the catalytic and DNA-binding domains of the Type IIf enzymes are distinct and well separated, discretely inactivating either should present no more of a challenge than would the same for Type IIs enzymes. Combining the resulting two, inactive, enzymes—one deficient in catalysis, the other deficient in DNA-binding—should produce a DNA-nicking activity comparable to that envisaged for FokI:

| | |
|---|---|
| RM.Eco57I active homodimer ($C^+D^+M^+B^+:C^+D^+M^+B^+$) | CTGAAGNNNNNNNNNNNNNNN^N . . . GACTTCNNNNNNNNNNNNNN^NNN . . . |
| N.Eco57I nicking 'heterodimer' ($C^-D^+M^+B^+:C^+D^+M^+B^-$ or $C^-D^+M^+B^+:C^+D^+$) | CTGAAGNNNNNNNNNNNNNNN^N . . . GACTTCNNNNNNNNNNNNNNNNN . . . |

(In the above sequences, the strand-specificity of the hypothetical nicking enzyme is shown to nick the top strand.)

The methyltransferase activity of the BcgI endonuclease-methyltransferase can be abolished without loss of DNA-cleavage activity (Kong and Smith, *Nucleic Acids Res.* 25:3687–3692 (1997); Kong, *J. Mol. Biol.* 279:823–832 (1998)). The same is probably true for other Type IIf enzymes, and so methylation-deficient mutants of Eco57I could likely be constructed that would mimic ordinary Type IIs endonucleases in function. In the Example above, then, the two defective enzymes that in combination create the nicking activity need not be $M^+$, but either could be $M^-$ instead. The binding domain of these enzymes is an extension of the methyltransferase domain, and the two activities are interdependent to such an extent that mutations in either domain would likely abolish both activities. It would probably be rather straightforward, therefore, to make the following combination: $C^-D^+M^+B^+:C^+D^+M^-B^-$ or $C^-D^+M^+B^+:C^+D^+$.

Certain Type IIf enzymes, such as HaeIV, cleave DNA on both sides of their recognition sequences (Piekarowicz et al., *J. Mol. Biol.* 293:1055–1065 (1999)). These enzymes bind to DNA as homodimers, and then in all likelihood accomplish cleavage by dimerization between the catalytic domains of adjacent homodimers. Combinations of defective mutants of these enzymes, too, could produce DNA nicking activity, although in these cases, since the recognition sequences are symmetric, the nicks would occur on both sides of these sequences, albeit on opposite strands. For HaeIV, the following activities are predicted:
RM.HaeIV cleaving homomultimer
  $(C^+D^+M^+B^+:C^+D^+M^+B^+):(C^+D^+M^+B^+:C^+D^+M^+B^+)$
  . . . NNNNNN^NNNNNNNNGAYNNNNNRTCNN-NNNNNNNNNN^N . . .
  .    .    .    N^NNNNNNNNNNNNNC-TRNNNNNYAGNNNNNNNNNANNNNNN . . .
Hypothetical N.HaeIV nicking heteromultimers
  $(C^-D^+M^+B^+:C^-M^+B^+):(C^+D^+M^*B^-:C^+D^+M^*B^-)$ or
  $(C^-D^+M^+B^+:C^-D^+M^+B^+):C^+D^+$
  . . . NNNNNNNNNNNNNNGAYNNNNNRTCNNN-NNNNNNNNNN^N . . .
  .    .    .    N^NNNNNNNNNNNNNC-TRNNNNNYAGNNNNNNNNNNNNNNNN . . .
(In the above sequences the location of the nick sites are shown downstream of the recognition sequence.)

Melting of the DNA between the two nicks created by a HaeIV-like nicking enzyme combination would produce DNA fragments with unusually long—37 base in this Example—single-stranded ends of unique, complimentary sequence. Such ends could be useful markers in complex genomes, and might be used to facilitate the proper assembly of such genomes following engineering.

Type IIs and Type IIf restriction endonucleases that cleave DNA as homodimers can in principle be converted into combinational heterodimers that nick DNA in the following steps:

4.1 The gene for the endonuclease is cloned, its nucleotide sequence is determined, and the amino acid sequence of the endonuclease protein is computed.

4.2 The amino acid sequence is analyzed for catalytic and structural motifs, and it is compared to the sequences of other endonucleases. The likely functional organization of the enzyme is established.

4.3 Mutants are made in the putative DNA-binding domain with the object of discretely abolishing sequence-specific DNA binding, without affecting folding, dimerization, or catalytic ability. The mutations can be targeted or random, and they can include point-mutations, deletions and insertions. Such mutants will likely not harm the host cell in the absence of protective modification. Crude, or partially purified, enzyme is prepared from the mutants, assayed for DNA cleavage activity and shown to be inactive. The desired, $B^-C^+D^+$, or $C^+D^+$ enzyme mutants can be recognized by their ability to enhance the activity of dilute wild-type enzyme preparations.

4.4 Mutants are made in the putative catalytic site with the object of discretely abolishing catalysis without affecting protein-folding, DNA-binding, or dimerization. Such mutants will also likely not harm the host cell in the absence of protective modification. Crude, or partially purified, enzyme is prepared from the mutants, assayed for DNA cleavage activity and also shown to be inactive. These enzyme preparations are then mixed with preparations of $B^-C^+D^+$ or $C^+D^+$ enzymes from the previous step and re-assayed, this time for DNA-nicking activity. The desired, $B^+C^-D^+$ enzymes can be recognized by their ability to nick DNA sequence-specifically in combination with an appropriate $B^-C^+D^+$ or $C^+D^+$ enzyme preparation.

4.5 The mutants can be isolated in reverse order if necessary, $B^+C^-D^+$ enzymes being isolated prior to the isolation of $B^-C^+D^+$ or $C^+D^+0$ enzymes. Once mutants of both types have been isolated, each can be used, in turn, to recover more effective mutants of the other in boot-strap fashion.

What is claimed is:

1. A method for converting into a sequence-specific, strand-specific and location-specific DNA nicking endonuclease, a restriction endonuclease that recognizes an asymmetric duplex DNA sequence, the endonuclease possessing two different catalytic sites, the method comprising:
   inactivating by mutation, one catalytic site, so as to convert the restriction endonuclease into the nicking endonuclease that selectively cleaves one strand of the duplex; and
   expressing the nicking endonuclease in an individual cell clone.

2. A method according to claim 1, wherein the restriction endonuclease is dimeric, comprising a first subunit and a second different subunit wherein the first subunit contains a first catalytic site and the second subunit contains a second catalytic site, the method further comprising inactivating the first catalytic site so as to form a dimeric nicking endonuclease.

3. A method according to claim 1, wherein the restriction endonuclease is dimeric, comprising a first subunit and a second different subunit, wherein the first subunit contains a first catalytic site and the second subunit contains a second catalytic site, the method further comprising inactivating the second catalytic site so as to form a dimeric nicking endonuclease of opposite strand specificity to that produced if the first catalytic site is inactivated.

4. A method according to claim 1, wherein the restriction endonuclease is monomeric, comprising at least a first domain and a second domain wherein the first domain contains a first catalytic site and the second domain contains a second catalytic site, the method further comprising inactivating the first catalytic site so as to form a monomeric nicking endonuclease.

5. A method according to claim 1, wherein the restriction endonuclease is monomeric, comprising at least a first domain and a second domain wherein the first domain contains a first catalytic site and the second domain contains a second catalytic site, the method further comprising inactivating the second catalytic site so as to form a monomeric nicking endonuclease of opposite strand specificity to that produced by inactivating the first catalytic site.

6. A method according to claim 1, wherein the restriction endonuclease is selected from AciI, BbvCI, Bpu10I, BsrBI, BssSI, BtrI GdiII, BsmI, BsrI, SimI, BsrD1, BstF51, BtsI, BstNBI, and BbvI.

7. A method according to claim 1, wherein inactivating one catalytic site further comprises modifying one or more amino acids in a predetermined region of the restriction endonuclease by site specific mutagenesis.

8. A method according to claim 1, wherein inactivating one catalytic site further comprises changing one or more amino acids in a conserved motif in the restriction endonuclease, the conserved motif identified through comparison of the amino acid sequences of similar proteins.

9. A method according to claim 8, wherein the conserved motif is a EXK motif, where E is glutamine, X is a non-polar amino acid and K is lysine.

10. A method for converting into a sequence-specific, strand-specific and location-specific DNA nicking endonuclease, a homodimeric restriction endonuclease that recognizes an asymmetric duplex DNA sequence, the restriction endonuclease possessing two identical catalytic sites, the method comprising:
   (a) creating by mutation, a first inactive homodimeric restriction endonuclease mutant, the mutant being cataiytically active and unable to bind to the recognition sequence;
   (b) creating by mutation, a second inactive homodimeric restriction endonuclease mutant, the mutant being catalytically inactive and binding to the recognition sequence; and
   (c) combining the inactive homodimeric restriction endonuclease of (a) and (b) to form the sequence-specific, strand-specific and location-specific DNA nicking endonuclease.

11. A method of claim 10, wherein the homodimeric restriction endonuclease is a type IIs restriction endonuclease.

12. A method of claim 10, wherein the homodimeric restriction endonuclease is a type IIf restriction endonuclease.

13. A method of claim 11, wherein the homodimeric restriction endonuclease is FokI.

14. A method of claim 12, wherein the homodimeric restriction endonuclease is Eco 57I or Hae IV.

15. A method according to claim 10, wherein the homodimeric restriction endonuclease has a C-terminus, the catalytic site being located at the C-terminus.

16. A method according to claim 10, wherein the homodimeric restriction endonuclease has a N-terminus, the catalytic site being located at the N-terminus.

17. A cell expressing a sequence-specific, strand-specific and location-specific nicking endonuclease made according to the method of claim 1.

18. A cell according to claim 17, wherein the nicking endonuclease is derived from a restriction endonuclease selected from the group consisting of AciI, BbvCI, Bpu 10I, BsrBI, BssSI, BtrI, GdiII, BsmI, BsrI, SimI, BsrD1, BstF51, BtsI, BstNBI, and BbvI.

* * * * *

SEQUENCE LISTING

```
<160> NUMBER OF SEQ ID NOS: 82
<210> SEQ ID NO 1
<211> LENGTH: 4665
<212> TYPE: DNA
<213> ORGANISM: Bacillus brevis

<400> SEQUENCE: 1
atcgattgca aaaagagtcc gcctgattca cttgtggttg atataatatg cagagatttt      60
cagtttcata agaaaggttt gatcaagttg ttaaatatgg aatctgaaac acgtcaaaat     120
atacaaaaac agttgacggc tatagatctt tttgctggtg cgggtgggtt tagtttggga     180
ttctcaatgg cggggtttcg tgtcactcat gccatcgaag tggataagtg ggcagctgaa     240
actttcgaag ttaattttcc tagaacaaaa gtggtcacgc gtgatatcca gcagatctct     300
gacgaagaga taaggatat tattgacgag cgtcctttgg ttgtaattgg aggaccaccg     360
tgtcaagggt tctcacatag taacgttaac aataaagatc ctaaggatcc gagaaattcg     420
ttgttccaag agtacatgcg atttgttgct caactacgac ctaaagtttg tatgattgag     480
aacgttaaag gtttacttac tactaagact gcaaaggag agttggtaat agatattatt     540
ctaagagaat ttgaatcatt aggttacaat gctgattttc gggtattaaa tgcagctaat     600
tttggtgttc ctcaatttcg ggaacggctt attatcgcag ctgtatgcaa atcagaagct     660 aataattct tttggccgga acctactcat gagttgggga attctaacat cacctcacta     720
```

-continued

```
tttgaggagt tgatgccgac acaacctcca ttgactcttt gggaagcaat aggtgatatt        780
cagcaaatca cacatgaatc atatacagga aagaaggat atgaatgttc tccattaaat         840
gaatttcaaa gtataatgcg aaggaatgcc ccagaattc tttttaaatca cgagcctatg        900 aagcacacca agcgagttgt tgaaagatat gcgaccattg gctttggtga atccgaagga        960
gatgtgtcag agaagcatct tcctcgcaaa cgaagtgaat cgtcaactat ttctaaagca       1020
tatgatcaaa atggtcgtcg gcagcgtcct gaccgaccgt gtagtactat tgttgcgtcc       1080
tctcatagta atttcataca tccttttctt catcgtaatt tcacagttcg ggagttagct       1140
cgtattcaat ccttccctga cgattatgaa tttcgaggaa aacgagcggt tttaagtaag       1200
aaactctcga tacgtaaagg tctgctggac gaaatatatt tggatcaaag aatgcaggta       1260
ggtaatgcag tacctcctct attcgcaaaa gctttagcag agtcagtacg ttctactctg       1320
tcattaacaa atagtagagg tggaaaaaat gaaatttgta gcacttgata ttttttgctgg      1380 ttgtggagga ttttcatctg gattgataca agctggccat gaagtgacat cagcccttga       1440
aatagattct tgggctgctg aaacatacca attcaaccac agaaatgtca atctattaac       1500
agaggatatt acgaaggtcg actcgactta ttttaaagtg aatttcaaag accgagttaa       1560
ccttgtggta ggaggaccgc catgtcaggg cttttcggtt tctggtccaa gacagtacgg       1620
agtatacaag aaagaaaatg ctttagttgc agaatacatt cgtgttatta agccgtgga       1680 gccagaatat ttcatattag aaaatgtacg tggctttaca accgcaacga tagagggacg       1740
aataaaagcc ttaaacttct tattggctga gcttcgcgaa atcgggtacc acgtatatca       1800
tgacgtactg caagcagccg attatggtgt gccacagctt cgttctaggt tattcgttgt       1860
cggttctcgt catcctattg ccaatccctt tcctaataaa acacactcgt aaatggtac       1920 acagcatctt agaccttatc tttccattat ggaggctatc ggtgacttgc ccatcattaa       1980
tgcttgcgaa ggtaccgata atttggttca gtactcgctg gagccacaaa acgactttca       2040
acaggcaatg agaaatggtt ctcttggggt gtacaatcat gaagctatga agcactctgc       2100
aaggattgtt gaacggtttg ctactatcca accaggtgga agtggctaca agcttggaac       2160
agtaaaaggg aaagatgctc ccgagaccgt gtataaatca acaatcagc gtcttatatc       2220 agatcaacca gcactatgta ttacggcgaa ttggcagtcg tcttacatcc atccgttact       2280
aaatcgaaat ttaactgttc gagaagctgc tcgtattcaa acatttcctg attcgtatgt       2340
gtttaaaggg aaaagggctg ttccaagtgc ttctttgttg agaaaacttg ggagagatga       2400
tgaaaatttc ctcagtcagt gtcatcaagt aggtaatgca gtaccaccctt tactggcaaa      2460 gcaaattttc gagaggctat ctgttgcagt ggagggagta gatgaggaaa gttcggaaca       2520
actacaatta tgggggtagt aatgattaac gaggactttt ttatttatga gcaattgtct       2580
cacaagaaaa atttagagca aaggggaaa aatgcatttg atgaagagac ggaggaactt       2640
gtaaggcaag ccaaaagtgg ctatcatgcc tttattgaag gaataaatta tgacgaagta       2700
acaaaactgg atctcaatag ttctgtagct gcattagaag attacatctc cattgcgaaa       2760
gaaatagaga aaaacataa aatgtttaac tggcgaagtg actatgctgg aagcattatt       2820
ccagaatttt tgtatagaat tgtgcatgta gcaactgtga agctgggtt aaaacctatt       2880 ttctctacga gaaatacaat tattgagatc agtggagcgg cacatagga aggattacaa       2940 atacgacgta aaaacgaaga ttttgcgttg gttttcatg aggtagacgt taaaattgca       3000
agtgagagtc atagagttat tagtttagcc gtcgcatgtg aagttaaaac aaatatcgat       3060
aaaaacaaac ttaatgggtt agacttttcg gctgagcgga tgaaacgcac atatccaggt       3120
```

-continued

```
tctgcttatt ttttaataac cgagacccta gattttccc cagatgagaa tcattcatct   3180
ggtctcatcg atgaaattta tgttcttcga aaacaagtgc gcaccaaaaa ccgagttcag   3240
aaggcaccgc tatgccctag tgtttttgca gagttgttgg aagacattct gaaatatca    3300 taccgtgcat ctaatgtaaa aggacatgtt tatgatcgtt tggagggagg gaagttaata   3360
cgtgtttaac caatttaatc cgttagtata tacacacggt ggaaaacttg aacggaagtc   3420
taagaaggat aaaacagcaa gtaaggtgtt cgaagaattt ggtgtgatgg aggcttataa   3480
ttgttggaag gaagcttccc tatgtattca caaagagac aaggatagcg ttcttaaact    3540
tgtagcagct ctcaatacgt ataaagacgc agtagaacca attttttgact caagactgaa  3600 tagtgcccaa gaagttctcc aaccgtcgat tttagaagaa ttttttgaat atctgtttag   3660
caggattgac tctattgttg gagtgaatat tccaattcga catccagcga agggttattt   3720
aagtctcagc tttaatccac ataatataga aacgctcatc caatcgccgg agtacactgt   3780
aagggcgaag gatcatgatt ttattattgg tgggtcagcg aaattaacca ttcaaggaca   3840
tggcggggaa ggagaaacaa ccaacattgt ggttcctgct gtagcgattg aatgcaagcg   3900
gtaccttgaa cgaaacatgc tagatgaatg tgctggtact gctgagcgct taaaaagagc   3960
aacaccatat tgtttatact tcgtagttgc ggagtactta aaactagatg atggagcacc   4020
ggaattaacc gagattgatg agatttacat acttcggcac cagcggaact cagagcggaa   4080
taagccagga tttaagccta accccataga tggtgaactg atttgggatt tgtaccaaga   4140
agttatgaat catcttggga agatttggtg ggatccaaac tcagctttac aacgcggtaa   4200
agtgtttaat cgaccataat aaacgtttct aatctagtaa tttcacctaa atgatggagc   4260
gaaatcggaa caactcgaaa cggtgagaat ccttttttgaa caagggtat ttgccgtttt    4320 ttgtttgccc gttcgttatt cataacaaag atgcgggtaa ggaacatgca tttagactgt   4380
atttaggatg tacttggcta tgatgcgcct acaatcaata aaccagatga gctgatcgga   4440
acactattag tccagtatgg aaagatatta tggacgggat tccctacac tcaccaaaac    4500 tttctgcgat gcgagtttag gaagaaattg cttttgctga agtaattttt tacatattaa   4560
gttagccgta atcacggaaa gagcaaagaa taaatgttaa agtgaacacc gctctaagat   4620
ggtggaagtg tcaatgttga ttattccact catgtggagt gtaca                   4665
```

<210> SEQ ID NO 2
<211> LENGTH: 423
<212> TYPE: PRT
<213> ORGANISM: Bacillus brevis

<400> SEQUENCE: 2

```
Met Glu Ser Glu Thr Arg Gln Asn Ile Gln Lys Gln Leu Thr Ala Ile
1               5                   10                  15

Asp Leu Phe Ala Gly Ala Gly Gly Phe Ser Leu Gly Phe Ser Met Ala
            20                  25                  30

Gly Phe Arg Val Thr His Ala Ile Glu Val Asp Lys Trp Ala Ala Glu
        35                  40                  45

Thr Phe Glu Val Asn Phe Pro Arg Thr Lys Val Thr Arg Asp Ile
    50                  55                  60

Gln Gln Ile Ser Asp Glu Ile Lys Asp Ile Asp Glu Arg Pro
65                  70                  75                  80

Leu Val Val Ile Gly Gly Pro Pro Cys Gln Gly Phe Ser His Ser Asn
                85                  90                  95
```

```
Val Asn Asn Lys Asp Pro Lys Asp Pro Arg Asn Ser Leu Phe Gln Glu
        100                 105                 110

Tyr Met Arg Phe Val Ala Gln Leu Arg Pro Lys Val Cys Met Ile Glu
            115                 120                 125

Asn Val Lys Gly Leu Leu Thr Thr Lys Thr Ala Lys Gly Glu Leu Val
        130                 135                 140

Ile Asp Ile Ile Leu Arg Glu Phe Glu Ser Leu Gly Tyr Asn Ala Asp
145                 150                 155                 160

Phe Arg Val Leu Asn Ala Ala Asn Phe Gly Val Pro Gln Phe Arg Glu
            165                 170                 175

Arg Leu Ile Ile Ala Ala Val Cys Lys Ser Glu Ala Asn Asn Phe Phe
            180                 185                 190

Trp Pro Glu Pro Thr His Glu Leu Gly Asn Ser Asn Ile Thr Ser Leu
            195                 200                 205

Phe Glu Glu Leu Met Pro Thr Gln Pro Pro Leu Thr Leu Trp Glu Ala
        210                 215                 220

Ile Gly Asp Ile Gln Gln Ile Thr His Glu Ser Tyr Thr Gly Lys Glu
225                 230                 235                 240

Gly Tyr Glu Cys Ser Pro Leu Asn Glu Phe Gln Ser Ile Met Arg Arg
            245                 250                 255

Asn Ala Pro Glu Phe Leu Leu Asn His Glu Pro Met Lys His Thr Lys
            260                 265                 270

Arg Val Val Glu Arg Tyr Ala Thr Ile Gly Phe Gly Glu Ser Glu Gly
            275                 280                 285

Asp Val Ser Glu Lys His Leu Pro Arg Lys Arg Ser Glu Ser Ser Thr
        290                 295                 300

Ile Ser Lys Ala Tyr Asp Gln Asn Gly Arg Arg Gln Arg Pro Asp Arg
305                 310                 315                 320

Pro Cys Ser Thr Ile Val Ala Ser Ser His Ser Asn Phe Ile His Pro
            325                 330                 335

Phe Leu His Arg Asn Phe Thr Val Arg Glu Leu Ala Arg Ile Gln Ser
            340                 345                 350

Phe Pro Asp Asp Tyr Glu Phe Arg Gly Lys Arg Ala Val Leu Ser Lys
            355                 360                 365

Lys Leu Ser Ile Arg Lys Gly Leu Leu Asp Glu Ile Tyr Leu Asp Gln
        370                 375                 380

Arg Met Gln Val Gly Asn Ala Val Pro Pro Leu Phe Ala Lys Ala Leu
385                 390                 395                 400

Ala Glu Ser Val Arg Ser Thr Leu Ser Leu Thr Asn Ser Arg Gly Gly
            405                 410                 415

Lys Asn Glu Ile Cys Ser Thr
            420

<210> SEQ ID NO 3
<211> LENGTH: 396
<212> TYPE: PRT
<213> ORGANISM: Bacillus brevis

<400> SEQUENCE: 3

Met Lys Phe Val Ala Leu Asp Ile Phe Ala Gly Cys Gly Gly Phe Ser
1               5                   10                  15

Ser Gly Leu Ile Gln Ala Gly His Glu Val Thr Ser Ala Leu Glu Ile
            20                  25                  30

Asp Ser Trp Ala Ala Glu Thr Tyr Gln Phe Asn His Arg Asn Val Asn
        35                  40                  45
```

```
Leu Leu Thr Glu Asp Ile Thr Lys Val Asp Ser Thr Tyr Phe Lys Val
 50                  55                  60

Asn Phe Lys Asp Arg Val Asn Leu Val Val Gly Pro Pro Cys Gln
 65                  70                  75                  80

Gly Phe Ser Val Ser Gly Pro Arg Gln Tyr Gly Val Tyr Lys Lys Glu
                     85                  90                  95

Asn Ala Leu Val Ala Glu Tyr Ile Arg Val Ile Lys Ala Val Glu Pro
                100                 105                 110

Glu Tyr Phe Ile Leu Glu Asn Val Arg Gly Phe Thr Thr Ala Thr Ile
            115                 120                 125

Glu Gly Arg Ile Lys Ala Leu Asn Phe Leu Leu Ala Glu Leu Arg Glu
        130                 135                 140

Ile Gly Tyr His Val Tyr His Asp Val Leu Gln Ala Ala Asp Tyr Gly
145                 150                 155                 160

Val Pro Gln Leu Arg Ser Arg Leu Phe Val Val Gly Ser Arg His Pro
                165                 170                 175

Ile Ala Asn Pro Phe Pro Asn Lys Thr His Ser Leu Asn Gly Thr Gln
            180                 185                 190

His Leu Arg Pro Tyr Leu Ser Ile Met Glu Ala Ile Gly Asp Leu Pro
        195                 200                 205

Ile Ile Asn Ala Cys Glu Gly Thr Asp Asn Leu Val Gln Tyr Ser Leu
210                 215                 220

Glu Pro Gln Asn Asp Phe Gln Gln Ala Met Arg Asn Gly Ser Leu Gly
225                 230                 235                 240

Val Tyr Asn His Glu Ala Met Lys His Ser Ala Arg Ile Val Glu Arg
                245                 250                 255

Phe Ala Thr Ile Gln Pro Gly Gly Ser Gly Tyr Lys Leu Gly Thr Val
            260                 265                 270

Lys Gly Lys Asp Ala Pro Glu Thr Val Tyr Lys Ser Asn Asn Gln Arg
275                 280                 285

Leu Ile Ser Asp Gln Pro Ala Leu Cys Ile Thr Ala Asn Trp Gln Ser
290                 295                 300

Ser Tyr Ile His Pro Leu Leu Asn Arg Asn Leu Thr Val Arg Glu Ala
305                 310                 315                 320

Ala Arg Ile Gln Thr Phe Pro Asp Ser Tyr Val Phe Lys Gly Lys Arg
            325                 330                 335

Ala Val Pro Ser Ala Ser Leu Leu Arg Lys Leu Gly Arg Asp Asp Glu
            340                 345                 350

Asn Phe Leu Ser Gln Cys His Gln Val Gly Asn Ala Val Pro Pro Leu
            355                 360                 365

Leu Ala Lys Gln Ile Phe Glu Arg Leu Ser Val Ala Val Glu Gly Val
        370                 375                 380

Asp Glu Glu Ser Ser Glu Gln Leu Gln Leu Trp Gly
385                 390                 395

<210> SEQ ID NO 4
<211> LENGTH: 275
<212> TYPE: PRT
<213> ORGANISM: Bacillus brevis

<400> SEQUENCE: 4

Met Ile Asn Glu Asp Phe Phe Ile Tyr Glu Gln Leu Ser His Lys Lys
 1               5                  10                  15

Asn Leu Glu Gln Lys Gly Lys Asn Ala Phe Asp Glu Glu Thr Glu Glu
                20                  25                  30
```

```
Leu Val Arg Gln Ala Lys Ser Gly Tyr His Ala Phe Ile Glu Gly Ile
        35                  40                  45

Asn Tyr Asp Glu Val Thr Lys Leu Asp Leu Asn Ser Ser Val Ala Ala
    50                  55                  60

Leu Glu Asp Tyr Ile Ser Ile Ala Lys Glu Ile Glu Lys Lys His Lys
65                  70                  75                  80

Met Phe Asn Trp Arg Ser Asp Tyr Ala Gly Ser Ile Ile Pro Glu Phe
                85                  90                  95

Leu Tyr Arg Ile Val His Val Ala Thr Val Lys Ala Gly Leu Lys Pro
            100                 105                 110

Ile Phe Ser Thr Arg Asn Thr Ile Glu Ile Ser Gly Ala Ala His
            115                 120                 125

Arg Glu Gly Leu Gln Ile Arg Arg Lys Asn Glu Asp Phe Ala Leu Gly
            130                 135                 140

Phe His Glu Val Asp Val Lys Ile Ala Ser Glu Ser His Arg Val Ile
145                 150                 155                 160

Ser Leu Ala Val Ala Cys Glu Val Lys Thr Asn Ile Asp Lys Asn Lys
                165                 170                 175

Leu Asn Gly Leu Asp Phe Ser Ala Glu Arg Met Lys Arg Thr Tyr Pro
            180                 185                 190

Gly Ser Ala Tyr Phe Leu Ile Thr Glu Thr Leu Asp Phe Ser Pro Asp
            195                 200                 205

Glu Asn His Ser Ser Gly Leu Ile Asp Glu Ile Tyr Val Leu Arg Lys
            210                 215                 220

Gln Val Arg Thr Lys Asn Arg Val Gln Lys Ala Pro Leu Cys Pro Ser
225                 230                 235                 240

Val Phe Ala Glu Leu Leu Glu Asp Ile Leu Glu Ile Ser Tyr Arg Ala
                245                 250                 255

Ser Asn Val Lys Gly His Val Tyr Asp Arg Leu Glu Gly Gly Lys Leu
            260                 265                 270

Ile Arg Val
        275

<210> SEQ ID NO 5
<211> LENGTH: 285
<212> TYPE: PRT
<213> ORGANISM: Bacillus brevis

<400> SEQUENCE: 5

Met Phe Asn Gln Phe Asn Pro Leu Val Tyr Thr His Gly Gly Lys Leu
1               5                   10                  15

Glu Arg Lys Ser Lys Lys Asp Lys Thr Ala Ser Lys Val Phe Glu Glu
            20                  25                  30

Phe Gly Val Met Glu Ala Tyr Asn Cys Trp Lys Glu Ala Ser Leu Cys
        35                  40                  45

Ile Gln Gln Arg Asp Lys Asp Ser Val Leu Lys Leu Val Ala Ala Leu
    50                  55                  60

Asn Thr Tyr Lys Asp Ala Val Glu Pro Ile Phe Asp Ser Arg Leu Asn
65                  70                  75                  80

Ser Ala Gln Glu Val Leu Gln Pro Ser Ile Leu Glu Glu Phe Phe Glu
                85                  90                  95

Tyr Leu Phe Ser Arg Ile Asp Ser Ile Val Gly Val Asn Ile Pro Ile
            100                 105                 110

Arg His Pro Ala Lys Gly Tyr Leu Ser Leu Ser Phe Asn Pro His Asn
        115                 120                 125
```

-continued

```
Ile Glu Thr Leu Ile Gln Ser Pro Glu Tyr Thr Val Arg Ala Lys Asp
    130                 135                 140

His Asp Phe Ile Ile Gly Gly Ser Ala Lys Leu Thr Ile Gln Gly His
145                 150                 155                 160

Gly Gly Glu Gly Glu Thr Thr Asn Ile Val Val Pro Ala Val Ala Ile
                165                 170                 175

Glu Cys Lys Arg Tyr Leu Glu Arg Asn Met Leu Asp Glu Cys Ala Gly
            180                 185                 190

Thr Ala Glu Arg Leu Lys Arg Ala Thr Pro Tyr Cys Leu Tyr Phe Val
        195                 200                 205

Val Ala Glu Tyr Leu Lys Leu Asp Asp Gly Ala Pro Glu Leu Thr Glu
    210                 215                 220

Ile Asp Glu Ile Tyr Ile Leu Arg His Gln Arg Asn Ser Glu Arg Asn
225                 230                 235                 240

Lys Pro Gly Phe Lys Pro Asn Pro Ile Asp Gly Glu Leu Ile Trp Asp
                245                 250                 255

Leu Tyr Gln Glu Val Met Asn His Leu Gly Lys Ile Trp Trp Asp Pro
            260                 265                 270

Asn Ser Ala Leu Gln Arg Gly Lys Val Phe Asn Arg Pro
        275                 280                 285
```

```
<210> SEQ ID NO 6
<211> LENGTH: 2400
<212> TYPE: DNA
<213> ORGANISM: Bacillus lentus

<400> SEQUENCE: 6
aagctttgca aagtactatg attagagata gtatagaata atttaatgtt aaagttgtta     60
taaattgaaa ggataaaata ttttccgcta attgagtata taagttataa tatgagaata    120
taagttctgt tttgttggta tgataaaaat gtaagttaat ataaaggagt tatgaaattt    180
gaaagtttta gatttgtttg ctggtgcagg agggtttagc cttggctttg aaatggctga    240
ttatgaagta attggcggtg ttgaaattga caaatgggct ggtgaaacat tagcacacaa    300
tcatcccggg ataattctaa taaacaaaaa tatcacaaat gttacaaatg aagagttact    360
agaaaaattt aaggacaatt tcccagatgt aataattgga gggcctccat gccaagggtt    420
ttctattagt aatagaaaag caggggaccc aaaagaccca aggaattctt tatttaaaga    480
atttattaga attgcttcag tttttaaacc tcaatattta gtaatggaga atgttcctaa    540
tctattaaag gcgaaaacgg agaataaaga attagtaata gatattatac gaaaagaaat    600
ggagaattta ggttataatg tttacgtaga tgttttaagt gctacagatt ttggtgtgcc    660
acaaataaga aaacgattat ttgttattgg ttcaaagact aaactagaca aaccatttcc    720
ttctccgact cattatgttc ttggtgaaaa tgattccctc tttaatgaaa aattagaaat    780
aacacctaca ctttgggatg caatttcaga tttaccaaca atcgaagcac gagagggtgc    840
cgaagaaatg gaatacacga tggaaccaca gactgattat caaagatatt taagagaagg    900
ttctgctaaa gtatataatc ataaagccat gaatcatact aaaagaatgg tagaacgatt    960
tgcctctatg acgtttggaa attctatttc agatgtacct gaacatttaa gaccttataa   1020
acgaaatcag gtcggagtga tttctgataa attatacgac caaaataacc gtcggatgtt   1080
ccctgataga ccatgccata ctattgctgc ctctttctac gcaaattttg ttcatccatt   1140
tttgaataga aactttactg ctagagaagg tgcacgaatt caatcttttc ctgatagtta   1200
tgtctttaag ggtaagccta cagtagtaag taagaagtta cttgcaagtg aaggcagaac   1260
```

-continued

```
tgatgaatct tatctttgcc aatataacca aattggcaat gctgtccccc ctatgttagc   1320
aaaagcaatt gctgacaatt tgaaaaaaaa ctagtgtaaa agagggaaat ttatgttcgt   1380
tcatggagat aatttaacgc aaaaagaaaa tcatcgtaca aaatatacag atggtttgtc   1440
taaacaatat ttaacagaaa taagagaaaa atataatgaa tggaaaaaag ccaacgaaga   1500
attgataggt ccttttgctg aggcaacgcc tgaagatgaa gcaatagtga aaaaaagagt   1560
agaattgctg aatgattata aagattttgt agaccaacaa cactatgcgg aaaaatttga   1620
ttcacgttcg aacctacatt cctcaatttt agaagaattt gtctactacc tgtttaagga   1680
tatagcaaaa agttttaatg atgaagccat tgtaggtaaa tcacatgctt ttaaagattt   1740
gtttataaat cctagtagtt ataaagatat ggtaactcaa ccaaatgtaa aggtagaaat   1800
taaggaccat gattttatta ttggtgtagg aattgaagca aaaatgattg tcaaaggttc   1860
aactgaaatt gaaaatcata ctttagaagt agcggcggtt gcgattgaat gtaaaacata   1920
tttagataaa acaatgctag agggttcatc agttgccgca gaacaattga aaagtaggaa   1980
tcctaacgca aaatatattg tagtatcaga atggttaaag ctatctgaac aagtaaacct   2040
tcagaaatat aaagttgacc aaatttatgt tttgagaaaa caaaaaaata ctgatagaga   2100
atttagatat gctgacacgt acgtgaaaaa tgctattcat gaagatgtag ttttacattt   2160
attccataca ataagattac acttaactac tgaatgggat gggtctatta gccatggtat   2220
tgatagaggt tacctactat agaacctaaa tgaggttatt cctattatct gttaaaaata   2280
tactaagcga attgtaagtg gataaatcac tgtatttaaa aaaaatatcc aacgccttga   2340
attgaaggtg ttggatattt ttttatgcat ttttattttc tatcaaatat taacactact   2400
```

```

<210> SEQ ID NO 7
<211> LENGTH: 391
<212> TYPE: PRT
<213> ORGANISM: Bacillus lentus

<400> SEQUENCE: 7

Met Lys Val Leu Asp Leu Phe Ala Gly Ala Gly Gly Phe Ser Leu Gly
1               5                   10                  15

Phe Glu Met Ala Asp Tyr Glu Val Ile Gly Gly Val Glu Ile Asp Lys
            20                  25                  30

Trp Ala Gly Glu Thr Leu Ala His Asn His Pro Gly Ile Ile Leu Ile
        35                  40                  45

Asn Lys Asn Ile Thr Asn Val Thr Asn Glu Glu Leu Leu Glu Lys Phe
    50                  55                  60

Lys Asp Asn Phe Pro Asp Val Ile Ile Gly Gly Pro Pro Cys Gln Gly
65                  70                  75                  80

Phe Ser Ile Ser Asn Arg Lys Ala Gly Asp Pro Lys Asp Pro Arg Asn
                85                  90                  95

Ser Leu Phe Lys Glu Phe Ile Arg Ile Ala Ser Val Phe Lys Pro Gln
            100                 105                 110

Tyr Leu Val Met Glu Asn Val Pro Asn Leu Leu Lys Ala Lys Thr Glu
        115                 120                 125

Asn Lys Glu Leu Val Ile Asp Ile Ile Arg Lys Glu Met Glu Asn Leu
    130                 135                 140

Gly Tyr Asn Val Tyr Val Asp Val Leu Ser Ala Thr Asp Phe Gly Val
145                 150                 155                 160

Pro Gln Ile Arg Lys Arg Leu Phe Val Ile Gly Ser Lys Thr Lys Leu
                165                 170                 175
```

```
Asp Lys Pro Phe Pro Ser Pro Thr His Tyr Val Leu Gly Glu Asn Asp
            180                 185                 190

Ser Leu Phe Asn Glu Lys Leu Glu Ile Thr Pro Thr Leu Trp Asp Ala
            195                 200                 205

Ile Ser Asp Leu Pro Thr Ile Glu Ala Arg Gly Ala Glu Glu Met
            210                 215                 220

Glu Tyr Thr Met Glu Pro Gln Thr Asp Tyr Gln Arg Tyr Leu Arg Glu
225                 230                 235                 240

Gly Ser Ala Lys Val Tyr Asn His Lys Ala Met Asn His Thr Lys Arg
                245                 250                 255

Met Val Glu Arg Phe Ala Ser Met Thr Phe Gly Asn Ser Ile Ser Asp
            260                 265                 270

Val Pro Glu His Leu Arg Pro Tyr Lys Arg Asn Gln Val Gly Val Ile
            275                 280                 285

Ser Asp Lys Leu Tyr Asp Gln Asn Asn Arg Arg Met Phe Pro Asp Arg
            290                 295                 300

Pro Cys His Thr Ile Ala Ala Ser Phe Tyr Ala Asn Phe Val His Pro
305                 310                 315                 320

Phe Leu Asn Arg Asn Phe Thr Ala Arg Glu Gly Ala Arg Ile Gln Ser
                325                 330                 335

Phe Pro Asp Ser Tyr Val Phe Lys Gly Lys Pro Thr Val Val Ser Lys
            340                 345                 350

Lys Leu Leu Ala Ser Glu Gly Arg Thr Asp Glu Ser Tyr Leu Cys Gln
            355                 360                 365

Tyr Asn Gln Ile Gly Asn Ala Val Pro Pro Met Leu Ala Lys Ala Ile
            370                 375                 380

Ala Asp Asn Leu Lys Lys Asn
385                 390

<210> SEQ ID NO 8
<211> LENGTH: 289
<212> TYPE: PRT
<213> ORGANISM: Bacillus lentus

<400> SEQUENCE: 8

Met Phe Val His Gly Asp Asn Leu Thr Gln Lys Glu Asn His Arg Thr
1               5                   10                  15

Lys Tyr Thr Asp Gly Leu Ser Lys Gln Tyr Leu Thr Glu Ile Arg Glu
            20                  25                  30

Lys Tyr Asn Glu Trp Lys Lys Ala Asn Glu Glu Leu Ile Gly Pro Phe
        35                  40                  45

Ala Glu Ala Thr Pro Glu Asp Glu Ala Ile Val Lys Lys Arg Val Glu
    50                  55                  60

Leu Leu Asn Asp Tyr Lys Asp Phe Val Asp Gln Gln His Tyr Ala Glu
65                  70                  75                  80

Lys Phe Asp Ser Arg Ser Asn Leu His Ser Ser Ile Leu Glu Glu Phe
                85                  90                  95

Val Tyr Tyr Leu Phe Lys Asp Ile Ala Lys Ser Phe Asn Asp Glu Ala
            100                 105                 110

Ile Val Gly Lys Ser His Ala Phe Lys Asp Leu Phe Ile Asn Pro Ser
        115                 120                 125

Ser Tyr Lys Asp Met Val Thr Gln Pro Asn Val Lys Val Glu Ile Lys
    130                 135                 140

Asp His Asp Phe Ile Ile Gly Val Gly Ile Glu Ala Lys Met Ile Val
145                 150                 155                 160
```

```
Lys Gly Ser Thr Glu Ile Glu Asn His Thr Leu Glu Val Ala Ala Val
                165                 170                 175
Ala Ile Glu Cys Lys Thr Tyr Leu Asp Lys Thr Met Leu Glu Gly Ser
            180                 185                 190
Ser Val Ala Ala Glu Gln Leu Lys Ser Arg Asn Pro Asn Ala Lys Tyr
        195                 200                 205
Ile Val Val Ser Glu Trp Leu Lys Leu Ser Glu Gln Val Asn Leu Gln
    210                 215                 220
Lys Tyr Lys Val Asp Gln Ile Tyr Val Leu Arg Lys Gln Lys Asn Thr
225                 230                 235                 240
Asp Arg Glu Phe Arg Tyr Ala Asp Thr Tyr Val Lys Asn Ala Ile His
                245                 250                 255
Glu Asp Val Val Leu His Leu Phe His Thr Ile Arg Leu His Leu Thr
            260                 265                 270
Thr Glu Trp Asp Gly Ser Ile Ser His Gly Ile Asp Arg Gly Tyr Leu
        275                 280                 285
Leu

<210> SEQ ID NO 9
<211> LENGTH: 2808
<212> TYPE: DNA
<213> ORGANISM: Bacillus subtilis 36

<400> SEQUENCE: 9
taaatagagg aaagagaata cttaaaaaaa catagaaaga aggtgatccc atgcccacta      60
acaataaacc caatagatta atcgctgaga agtccccata tttactccaa cacgcccaca    120
accctgtgga ctggttcccg tggggagatg aagccttcga aaaagcaaaa cgcgaaaaca    180
agccggttct ggtcagcatc ggttattcga cttgccattg gtgccatgtt tactactacg    240
attaaatctt tggggtagat tgattccttt agaaagagta aaatgaactc gtattatgaa    300
ggagctgttt ataatgaagt atactcccca aaagattttt aaaacaatag atgattttcc    360
ttatgataga acatcagtat ctcaaagtga actagattta gatattaagg aaagaaaaag    420
tttattccca tggagagggc agttctctcc ttgtttaata gaattatttt tagatagata    480
ttcaaaacca gacgatgtta tatttgatcc atttgcaggt agtggtacca cacttttttga    540
gtctgctagg aaaaacctta aatgttatgg cgccgaaatt aatccctctg ctattacaat    600
gtcaaaaaca gttgaattca taaatatgtc aactgaagat agagaaaaac tatgtaatgc    660
agcacttctt cttctaaaaa aatatattag agaaagtaat tatgatttat ttaatatgga    720
tctttatgaa gaaaaaagtg caccattcga aattgcattc aaaaaaatgt taaacgaatc    780
gccaaacagt caagtgataa acatccttac taatgctcta attagattca aaagctatag    840
aggaaaaaaa gctctcgagg attactataa ggctttacat gaacatatta aaattattaa    900
aaatttgccg tactccgaaa atatatgtga ggttttccac accgatgcaa gatctatacc    960
tttagctaac gacagtgtag atttaatcat aacatctcca ccttatatta atgttttttaa   1020
ttatcatcaa aacaacaggg aggcaatgga gtttgttggt tggaatgtac tagaagtggc   1080
taaatctgaa atgggttcaa atcgaaaaca tagacagaat agatttttaa cagttattca   1140
atatagcatg gatatcttag aagcgctaat tgaaatgaga aggcttctaa ccccatcagg   1200
tagggtaatt attgtggtgg aagggaatc aaaaattaga ggtgttccct aaaaaacgg    1260
taggctagtg gctgctttag cttatggagg agctggattt aaaatcgaga atatgcaaga   1320
aagaaaattc acaaataaat ttggtgagtt aatttatgag gatattatac atctcacacc   1380
```

```
ctcaaataca tcagttttag atgagagcta cgcaaagaat atggccaatg aattattaaa    1440
agaagcgctg ataatggaaa aagacgaaaa tatcaggata gaaatcctta atgcaataaa    1500
caaatcagat agtgttaaaa aatcaccaat tttcgaaatg gattttaat ttcatatcta     1560 aggaggaatt taatgacaac ctatatatat cctaccccac ataaagataa attagttgcc    1620
ctattactaa acgataaatt accagtagaa gataaaccaa gagttgaaga ggcaattgtg    1680
gtttatacaa attggataaa aaacttaaac attattacaa gtgccggtct tcctccccaa    1740
cagactttaa ataaaatgat tgagcttcta aatgaatata aattctatat agatttaaat    1800
ttggtatttg atagcccaag agatttcctt tatagacaaa aagggcaatt aaaaattgac    1860
aatactatta ttgaagaatt tttaccccgt ttagctcatc cgtctgttat tcctgaaata    1920
atcgatatgg atgtaacggt tggaccaaaa aagtgttttt cttcagttta ctttgaatct    1980
agtcttgatg cgccagcaat tggaggagga ctaagagtaa gaagcaaaga ccaagacttt    2040
gcaataagca aaaattatt cttaaaagcg tcacacacac aagattataa agagagtttg     2100
gaaacagaaa cattcttatc ttatgtgtct gctgagtgta aaacaaatct tgataagaca    2160
atgtttcaag aaggatgtgc tacagctcat gatacgaagg tagctgtacc aggttctaaa    2220
tatttcttgc tatgtgaatg gttagatatg acaccattaa gtacagctcc tacagatatt    2280
gatgaaattc tacttctccg taaagccaaa agattaaatt ctaatataag aaaaaagttt    2340
tcttcttata gtgggagaca agaaaaacgg gattatttca tcaattatct caaatcacat    2400
ccatttagag tagaggtttt tgaaagattt attgaacaca ttagaaaact tatccaaaat    2460
gaagttccgg ttgaacataa tgttatggaa ttaggttatt tttaaaatag atcttatcta    2520
ttattagatg tttatatata aataagaacg ttaatactta ttttatactg tccgttatta    2580
ttactcataa aagaagaaag aaggtgatcc catgcccact aacaataaac ccaatagatt    2640
aatcgctgag aagtccccat atttactcca acacgcccac aaccctgtgg actggttccc    2700 gtgggggat gaagccttcg aaaaagcaaa acgcgaaaac aagccggttc tggtcagcat     2760
cggttattcg acttgccatt ggtgccatgt tatggcccac gaaagctt                 2808
```

<210> SEQ ID NO 10
<211> LENGTH: 417
<212> TYPE: PRT
<213> ORGANISM: Bacillus lentus

<400> SEQUENCE: 10

```
Met Lys Glu Leu Phe Ile Met Lys Tyr Thr Pro Gln Lys Ile Phe Lys
1               5                   10                  15

Thr Ile Asp Asp Phe Pro Tyr Asp Arg Thr Ser Val Ser Gln Ser Glu
            20                  25                  30

Leu Asp Leu Asp Ile Lys Glu Arg Lys Ser Leu Phe Pro Trp Arg Gly
        35                  40                  45

Gln Phe Ser Pro Cys Leu Ile Glu Leu Phe Leu Asp Arg Tyr Ser Lys
    50                  55                  60

Pro Asp Asp Val Ile Phe Asp Pro Phe Ala Gly Ser Gly Thr Thr Leu
65                  70                  75                  80

Phe Glu Ser Ala Arg Lys Asn Leu Lys Cys Tyr Gly Ala Glu Ile Asn
                85                  90                  95

Pro Ser Ala Ile Thr Met Ser Lys Thr Val Glu Phe Ile Asn Met Ser
            100                 105                 110

Thr Glu Asp Arg Glu Lys Leu Cys Asn Ala Ala Leu Leu Leu Leu Lys
        115                 120                 125
```

Lys Tyr Ile Arg Glu Ser Asn Tyr Asp Leu Phe Asn Met Asp Leu Tyr
130                 135                 140

Glu Glu Lys Ser Ala Pro Phe Glu Ile Ala Phe Lys Lys Met Leu Asn
145                 150                 155                 160

Glu Ser Pro Asn Ser Gln Val Ile Asn Ile Leu Thr Asn Ala Leu Ile
                165                 170                 175

Arg Phe Lys Ser Tyr Arg Gly Lys Lys Ala Leu Glu Asp Tyr Tyr Lys
            180                 185                 190

Ala Leu His Glu His Ile Lys Ile Lys Asn Leu Pro Tyr Ser Glu
        195                 200                 205

Asn Ile Cys Glu Val Phe His Thr Asp Ala Arg Ser Ile Pro Leu Ala
210                 215                 220

Asn Asp Ser Val Asp Leu Ile Thr Ser Pro Pro Tyr Ile Asn Val
225                 230                 235                 240

Phe Asn Tyr His Gln Asn Asn Arg Glu Ala Met Glu Phe Val Gly Trp
                245                 250                 255

Asn Val Leu Glu Val Ala Lys Ser Glu Met Gly Ser Asn Arg Lys His
            260                 265                 270

Arg Gln Asn Arg Phe Leu Thr Val Ile Gln Tyr Ser Met Asp Ile Leu
        275                 280                 285

Glu Ala Leu Ile Glu Met Arg Arg Leu Leu Thr Pro Ser Gly Arg Val
290                 295                 300

Ile Ile Val Val Gly Arg Glu Ser Lys Ile Arg Gly Val Pro Leu Lys
305                 310                 315                 320

Asn Gly Arg Leu Val Ala Ala Leu Ala Tyr Gly Gly Ala Gly Phe Lys
                325                 330                 335

Ile Glu Asn Met Gln Glu Arg Lys Phe Thr Asn Lys Phe Gly Glu Leu
            340                 345                 350

Ile Tyr Glu Asp Ile Ile His Leu Thr Pro Ser Asn Thr Ser Val Leu
        355                 360                 365

Asp Glu Ser Tyr Ala Lys Asn Met Ala Asn Glu Leu Leu Lys Glu Ala
370                 375                 380

Leu Ile Met Glu Lys Asp Glu Asn Ile Arg Ile Glu Ile Leu Asn Ala
385                 390                 395                 400

Ile Asn Lys Ser Asp Ser Val Lys Lys Ser Pro Ile Phe Glu Met Asp
                405                 410                 415

Phe

<210> SEQ ID NO 11
<211> LENGTH: 310
<212> TYPE: PRT
<213> ORGANISM: Bacillus subtilis 36

<400> SEQUENCE: 11

Met Thr Thr Tyr Ile Tyr Pro Thr Pro His Lys Asp Lys Leu Val Ala
1               5                   10                  15

Leu Leu Leu Asn Asp Lys Leu Pro Val Glu Asp Lys Pro Arg Val Glu
                20                  25                  30

Glu Ala Ile Val Val Tyr Thr Asn Trp Ile Lys Asn Leu Asn Ile Ile
            35                  40                  45

Thr Ser Ala Gly Leu Pro Pro Gln Gln Thr Leu Asn Lys Met Ile Glu
        50                  55                  60

Leu Leu Asn Glu Tyr Lys Phe Tyr Ile Asp Leu Asn Leu Val Phe Asp
65                  70                  75                  80

```
Ser Pro Arg Asp Phe Leu Tyr Arg Gln Lys Gly Gln Leu Lys Ile Asp
            85                  90                  95

Asn Thr Ile Ile Glu Glu Phe Leu Pro Arg Leu Ala His Pro Ser Val
        100                 105                 110

Ile Pro Glu Ile Ile Asp Met Asp Val Thr Val Gly Pro Lys Lys Cys
                115                 120                 125

Phe Ser Ser Val Tyr Phe Glu Ser Ser Leu Asp Ala Pro Ala Ile Gly
        130                 135                 140

Gly Gly Leu Arg Val Arg Ser Lys Asp Gln Asp Phe Ala Ile Ser Lys
145                 150                 155                 160

Lys Leu Phe Leu Lys Ala Ser His Thr Gln Asp Tyr Lys Glu Ser Leu
                165                 170                 175

Glu Thr Glu Thr Phe Leu Ser Tyr Val Ser Ala Glu Cys Lys Thr Asn
                180                 185                 190

Leu Asp Lys Thr Met Phe Gln Glu Gly Cys Ala Thr Ala His Asp Thr
                195                 200                 205

Lys Val Ala Val Pro Gly Ser Lys Tyr Phe Leu Leu Cys Glu Trp Leu
        210                 215                 220

Asp Met Thr Pro Leu Ser Thr Ala Pro Thr Asp Ile Asp Glu Ile Leu
225                 230                 235                 240

Leu Leu Arg Lys Ala Lys Arg Leu Asn Ser Asn Ile Arg Lys Lys Phe
                245                 250                 255

Ser Ser Tyr Ser Gly Arg Gln Glu Lys Arg Asp Tyr Phe Ile Asn Tyr
                260                 265                 270

Leu Lys Ser His Pro Phe Arg Val Glu Val Phe Glu Arg Phe Ile Glu
                275                 280                 285

His Ile Arg Lys Leu Ile Gln Asn Glu Val Pro Val Glu His Asn Val
                290                 295                 300

Met Glu Leu Gly Tyr Phe
305                 310

<210> SEQ ID NO 12
<211> LENGTH: 240
<212> TYPE: PRT
<213> ORGANISM: Desulfovibrio desulfuricans

<400> SEQUENCE: 12

Met Lys Ala Ala Thr Asp Gln Glu Leu Arg Lys Leu Ile Val Leu Tyr
1                5                  10                  15

Asn Asn Val Met Glu Val Met Glu His Asp Ala Ala Lys Ser Met Arg
            20                  25                  30

Asp Asp Asn Arg Ala Tyr Gly Gly Phe Val Arg Ala Ala Lys Gly Lys
        35                  40                  45

Ile Gln Glu Leu Ile Thr Glu Arg Leu Val Arg Thr Val Trp Asp Val
    50                  55                  60

Glu Met Gly Glu Asn Pro Glu Arg Leu Ser Ile Asn Ser Lys Lys Ile
65                  70                  75                  80

Lys Ile Pro Ile Leu Arg Ser Tyr Val Asp Ser Ile Asn Asp Glu Asn
                85                  90                  95

Leu Lys Lys Tyr Ile Ser Ser Asn Ile Leu Lys Tyr Ser Tyr Gly Leu
                100                 105                 110

Ser Val Asp Lys His Val Phe Ile Asp Asn Lys Phe Val Leu Gly Ile
            115                 120                 125

Glu Cys Lys Ala Tyr Thr Glu Asn Ala Met Leu Lys Arg Ile Leu Val
        130                 135                 140
```

```
Asp Phe Tyr Leu Leu Lys Thr Lys Phe Pro Lys Leu Asn Cys Phe Leu
145                 150                 155                 160

Phe Gln Leu Glu Ser Gln Leu Gly Gly Asp Tyr Ser Glu Cys Asn Lys
            165                 170                 175

Phe Pro Ile Gly Ser Tyr Pro Thr Arg Thr Ile Met Ser Tyr Phe Lys
            180                 185                 190

Asn Val Asp Leu Asn Ile Val Thr Leu Leu Glu Gly Glu Arg Lys Val
            195                 200                 205

Asp Arg Pro Ile Asn Lys Pro Gln Phe Phe Lys Pro Leu Lys Val Glu
        210                 215                 220

His Leu Glu Val Ala Ile Gly Tyr Leu Gln Glu Ser Leu Ser Glu Ile
225                 230                 235                 240

<210> SEQ ID NO 13
<211> LENGTH: 15
<212> TYPE: DNA
<213> ORGANISM: Unknown
<220> FEATURE:
<223> OTHER INFORMATION: enzyme with wild-type R1 subunit catalytic site

<400> SEQUENCE: 13
tgtgaagtta aaaca                                                    15

<210> SEQ ID NO 14
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 14
tgtgagatca cgaca                                                    15

<210> SEQ ID NO 15
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 15
tgtgagttga agaca                                                    15

<210> SEQ ID NO 16
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 16
tgtgagggca agaca                                                    15

<210> SEQ ID NO 17
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 17
tgtgtggaca agaca                                                    15
```

```
<210> SEQ ID NO 18
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 18
tgtggggtcc agaca                                                    15

<210> SEQ ID NO 19
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 19
tgtgacgtca agaca                                                    15

<210> SEQ ID NO 20
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 20
tgttaggtca agaca                                                    15

<210> SEQ ID NO 21
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 21
tgtggcgtgc agaca                                                    15

<210> SEQ ID NO 22
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 22
tgtgaggtgg agaca                                                    15

<210> SEQ ID NO 23
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 23
tgttacgtca acaca                                                    15

<210> SEQ ID NO 24
<211> LENGTH: 15
<212> TYPE: DNA
<213> ORGANISM: unknown
<220> FEATURE:
<223> OTHER INFORMATION: enzyme with mutated R1 subunit catalytic site
```

```
<400> SEQUENCE: 24
tgtggggtga agaca                                                      15

<210> SEQ ID NO 25
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 25
tgtgggatga acaca                                                      15

<210> SEQ ID NO 26
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 26
tgtgacgtcg agaca                                                      15

<210> SEQ ID NO 27
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 27
tgtgtggaga agaca                                                      15

<210> SEQ ID NO 28
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 28
tgtgacttca tgaca                                                      15

<210> SEQ ID NO 29
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 29
tgtgagctca acaca                                                      15

<210> SEQ ID NO 30
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 30
tgtgaggtca ggaca                                                      15
```

```
<210> SEQ ID NO 31
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 31
tgtgacgtct acaca                                                        15

<210> SEQ ID NO 32
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 32
tgtgacgtcg acaca                                                        15

<210> SEQ ID NO 33
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 33
tgtgagatca ggaca                                                        15

<210> SEQ ID NO 34
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 34
tgtgtgggct agaca                                                        15

<210> SEQ ID NO 35
<211> LENGTH: 15
<212> TYPE: DNA
<213> ORGANISM: unknown
<220> FEATURE:
<223> OTHER INFORMATION: enzyme with mutated R1 subunit catalytic site

<400> SEQUENCE: 35
tgtggcacgg acaca                                                        15

<210> SEQ ID NO 36
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 36
attgaatgca agcgg                                                        15

<210> SEQ ID NO 37
<211> LENGTH: 15
<212> TYPE: DNA
<213> ORGANISM: unknown
<220> FEATURE:
<223> OTHER INFORMATION: enzyme with mutated R2 subunit catalytic site
```

```
<400> SEQUENCE: 37
attgagggcc agcgg                                                15

<210> SEQ ID NO 38
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 38
attttgtgga agcgg                                                15

<210> SEQ ID NO 39
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 39
attgagtgga agcgg                                                15

<210> SEQ ID NO 40
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 40
attggctgca agcgg                                                15

<210> SEQ ID NO 41
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 41
attgggtgca agcgg                                                15

<210> SEQ ID NO 42
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 42
attgagaggc agcgg                                                15

<210> SEQ ID NO 43
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 43
attgagtgca tgcgg                                                15
```

<210> SEQ ID NO 44
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 44
attgggtgcg agcgg                                                    15

<210> SEQ ID NO 45
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 45
attcagtaca agcgg                                                    15

<210> SEQ ID NO 46
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 46
attgggtgga agcgg                                                    15

<210> SEQ ID NO 47
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 47
attgagtggg agcgg                                                    15

<210> SEQ ID NO 48
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 48
attgacgaca agcgg                                                    15

<210> SEQ ID NO 49
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 49
attgagttca accgg                                                    15

<210> SEQ ID NO 50
<211> LENGTH: 15
<212> TYPE: DNA
<213> ORGANISM: unknown
<220> FEATURE:
<223> OTHER INFORMATION: enzyme with mutated R2 subunit catalytic site

```
<400> SEQUENCE: 50
attgactgcg agcgg                                                    15

<210> SEQ ID NO 51
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 51
attgcctgga agcgg                                                    15

<210> SEQ ID NO 52
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 52
attccgtgca accgg                                                    15

<210> SEQ ID NO 53
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 53
attaagtgca gccgg                                                    15

<210> SEQ ID NO 54
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 54
attgagacca agcgg                                                    15

<210> SEQ ID NO 55
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 55
attgagaggg agcgg                                                    15

<210> SEQ ID NO 56
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 56
attgtctgca agcgg                                                    15
```

<210> SEQ ID NO 57
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 57
attgagtaca ggcgg                                                15

<210> SEQ ID NO 58
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 58
attgactacg agcgg                                                15

<210> SEQ ID NO 59
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 59
attgacggct ggcgg                                                15

<210> SEQ ID NO 60
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 60
attttgtgca agcgg                                                15

<210> SEQ ID NO 61
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 61
atttagtgca agcgg                                                15

<210> SEQ ID NO 62
<211> LENGTH: 15
<212> TYPE: DNA
<213> ORGANISM: unknown
<220> FEATURE:
<223> OTHER INFORMATION: enzyme with mutated R2 subunit catalytic site

<400> SEQUENCE: 62
attgactgca agcgg                                                15

<210> SEQ ID NO 63
<211> LENGTH: 15
<212> TYPE: DNA
<213> ORGANISM: Unknown
<220> FEATURE:
<223> OTHER INFORMATION: enzyme with mutated R2 subunit catalytic site

<400> SEQUENCE: 63
attgagagca agcgg                                                    15

<210> SEQ ID NO 64
<211> LENGTH: 16
<212> TYPE: DNA
<213> ORGANISM: unknown
<220> FEATURE:
<223> OTHER INFORMATION: oligonucleotide linker

<400> SEQUENCE: 64
ggcgctgagg ccacgt                                                   16

<210> SEQ ID NO 65
<211> LENGTH: 14
<212> TYPE: DNA
<213> ORGANISM: Unknown
<220> FEATURE:
<223> OTHER INFORMATION: oligonucleotide linker

<400> SEQUENCE: 65
aatggccctc agcc                                                     14

<210> SEQ ID NO 66
<211> LENGTH: 14
<212> TYPE: DNA
<213> ORGANISM: Unknown
<220> FEATURE:
<223> OTHER INFORMATION: oligonucleotide linker

<400> SEQUENCE: 66
attggctgag ggcc                                                     14

<210> SEQ ID NO 67
<211> LENGTH: 51
<212> TYPE: DNA
<213> ORGANISM: unknown
<220> FEATURE:
<223> OTHER INFORMATION: oligonucleotide linker

<400> SEQUENCE: 67
ggggcgagct caggaggtta aaatatggaa tctgaaacac gtcaaaatat a            51

<210> SEQ ID NO 68
<211> LENGTH: 40
<212> TYPE: DNA
<213> ORGANISM: unknown
<220> FEATURE:
<223> OTHER INFORMATION: oligonucleotide linker

<400> SEQUENCE: 68
gcaatagcat gcttactacc cccataattg tagttgttcc                         40

<210> SEQ ID NO 69
<211> LENGTH: 53
<212> TYPE: DNA
<213> ORGANISM: unknown
<220> FEATURE:
<223> OTHER INFORMATION: primer

<400> SEQUENCE: 69
gggggcatgc taaggaggtt taaaatatga ttaacgagga cttttttatt tat          53

```
<210> SEQ ID NO 70
<211> LENGTH: 42
<212> TYPE: DNA
<213> ORGANISM: unknown
<220> FEATURE:
<223> OTHER INFORMATION: primer

<400> SEQUENCE: 70
gcaatagagc tcttattatg gtcgattaaa cactttaccg cg                          42

<210> SEQ ID NO 71
<211> LENGTH: 68
<212> TYPE: DNA
<213> ORGANISM: unknown
<220> FEATURE:
<223> OTHER INFORMATION: oligonucleotide linker

<400> SEQUENCE: 71
ttattagttt agccgtcgca tgtgaggtca agacaaatat cgataaaaac aaacttaatg       60
ggttagac                                                               68

<210> SEQ ID NO 72
<211> LENGTH: 35
<212> TYPE: DNA
<213> ORGANISM: unknown
<220> FEATURE:
<223> OTHER INFORMATION: oligonucleotide primer

<400> SEQUENCE: 72
ctctatgact ctcacttgca attttaacgt ctacc                                 35

<210> SEQ ID NO 73
<211> LENGTH: 67
<212> TYPE: DNA
<213> ORGANISM: unknown
<220> FEATURE:
<223> OTHER INFORMATION: oligonucleotide primer

<400> SEQUENCE: 73
tggttcctgc tgtagcgatt gagtgcaagc ggtaccttga acgaaacatg ctagatgaat      60
gtgctgg                                                                67

<210> SEQ ID NO 74
<211> LENGTH: 34
<212> TYPE: DNA
<213> ORGANISM: unknown
<220> FEATURE:
<223> OTHER INFORMATION: oligonucleotide primer

<400> SEQUENCE: 74
caatgttggt tgtttctcct tccccgccat gtcc                                  34

<210> SEQ ID NO 75
<211> LENGTH: 25
<212> TYPE: DNA
<213> ORGANISM: Bacillus brevis

<400> SEQUENCE: 75
ggttaaaacc tattttctct acgag                                            25

<210> SEQ ID NO 76
<211> LENGTH: 25
<212> TYPE: DNA
<213> ORGANISM: Bacillus brevis
```

```
<400> SEQUENCE: 76
cttgttttcg aagaacataa atttc                                              25

<210> SEQ ID NO 77
<211> LENGTH: 24
<212> TYPE: DNA
<213> ORGANISM: Bacillus brevis

<400> SEQUENCE: 77
atttaagtct cagctttaat ccac                                               24

<210> SEQ ID NO 78
<211> LENGTH: 24
<212> TYPE: DNA
<213> ORGANISM: Bacillus brevis

<400> SEQUENCE: 78
gagttccgct ggtgccgaag tatg                                               24

<210> SEQ ID NO 79
<211> LENGTH: 24
<212> TYPE: DNA
<213> ORGANISM: unknown
<220> FEATURE:
<223> OTHER INFORMATION: custom-synthesized oligonucleotide primers

<400> SEQUENCE: 79
cacaattcca cacaacatac gagc                                               24

<210> SEQ ID NO 80
<211> LENGTH: 24
<212> TYPE: DNA
<213> ORGANISM: unknown
<220> FEATURE:
<223> OTHER INFORMATION: custom-synthesized oligonucleotide primers

<400> SEQUENCE: 80
tcgccacctc tgacttgagc gtcg                                               24

<210> SEQ ID NO 81
<211> LENGTH: 24
<212> TYPE: DNA
<213> ORGANISM: unknown
<220> FEATURE:
<223> OTHER INFORMATION: custom-synthesized oligonucleotide primers

<400> SEQUENCE: 81
ttcctttttc aatattattg aagc                                               24

<210> SEQ ID NO 82
<211> LENGTH: 24
<212> TYPE: DNA
<213> ORGANISM: unknown
<220> FEATURE:
<223> OTHER INFORMATION: custom-synthesized oligonucleotide primers

<400> SEQUENCE: 82
cgacacccgc caacacccgc tgac                                               24
```